US011603407B2

(12) United States Patent
Hu et al.

(10) Patent No.: US 11,603,407 B2
(45) Date of Patent: Mar. 14, 2023

(54) STABLE ANTIBODY FORMULATION

(71) Applicant: Regeneron Pharmaceuticals, Inc., Tarrytown, NY (US)

(72) Inventors: Qingyan Hu, Millwood, NY (US); Dingjiang Liu, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 15/927,783

(22) Filed: Mar. 21, 2018

(65) Prior Publication Data

US 2019/0040137 A1     Feb. 7, 2019

Related U.S. Application Data

(60) Provisional application No. 62/482,270, filed on Apr. 6, 2017.

(51) Int. Cl.
*A61K 39/395*     (2006.01)
*C07K 16/28*     (2006.01)
*A61K 47/18*     (2017.01)
*A61K 47/26*     (2006.01)
*A61K 9/00*     (2006.01)

(52) U.S. Cl.
CPC ........ *C07K 16/2818* (2013.01); *A61K 9/0019* (2013.01); *A61K 47/183* (2013.01); *A61K 47/26* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 4,997,423 A | 3/1991 | Okuda et al. |
| 5,629,204 A | 5/1997 | Honjo et al. |
| 5,698,520 A | 12/1997 | Honjo et al. |
| 5,908,686 A | 6/1999 | Sudo et al. |
| 6,286,699 B1 | 9/2001 | Sudo |
| 6,596,541 B2 | 7/2003 | Murphy et al. |
| 6,629,949 B1 | 10/2003 | Douglas |
| 6,645,635 B2 | 11/2003 | Muraki |
| 6,659,982 B2 | 12/2003 | Douglas et al. |
| 6,803,792 B2 | 10/2004 | Yasuda et al. |
| 6,808,710 B1 | 10/2004 | Wood et al. |
| 6,936,704 B1 | 8/2005 | Freeman et al. |
| 7,029,674 B2 | 4/2006 | Carreno et al. |
| 7,038,013 B2 | 5/2006 | Freeman et al. |
| 7,087,411 B2 | 8/2006 | Daly et al. |
| 7,101,550 B2 | 9/2006 | Wood et al. |
| 7,226,554 B2 | 6/2007 | Sudo et al. |
| 7,488,802 B2 | 2/2009 | Collins et al. |
| 7,521,051 B2 | 4/2009 | Collins et al. |
| 7,563,869 B2 | 7/2009 | Honjo et al. |
| 7,595,048 B2 | 9/2009 | Honjo et al. |
| 7,635,757 B2 | 12/2009 | Freeman et al. |
| 7,638,492 B2 | 12/2009 | Wood et al. |
| 7,709,214 B2 | 5/2010 | Freeman et al. |
| 7,722,868 B2 | 5/2010 | Freeman et al. |
| 7,794,710 B2 | 9/2010 | Chen et al. |
| 7,943,742 B2 | 5/2011 | Violette et al. |
| 7,943,743 B2 | 5/2011 | Korman et al. |
| 7,998,479 B2 | 8/2011 | Honjo et al. |
| 8,008,449 B2 | 8/2011 | Korman et al. |
| 8,088,905 B2 | 1/2012 | Collins et al. |
| 8,168,179 B2 | 5/2012 | Honjo et al. |
| 8,168,757 B2 | 5/2012 | Finnefrock et al. |
| 8,216,996 B2 | 7/2012 | Minato et al. |
| 8,217,149 B2 | 7/2012 | Irving et al. |
| 8,246,955 B2 | 8/2012 | Honjo et al. |
| 8,246,995 B2 | 8/2012 | Dai et al. |
| 8,257,740 B1 | 9/2012 | Sung et al. |
| 8,287,856 B2 | 10/2012 | Li et al. |
| 8,354,509 B2 | 1/2013 | Carven et al. |
| 8,383,796 B2 | 2/2013 | Korman et al. |
| 8,460,927 B2 | 6/2013 | Chen |
| 8,552,154 B2 | 10/2013 | Freeman et al. |
| 8,574,872 B2 | 11/2013 | Minato et al. |
| 8,580,247 B2 | 11/2013 | Li et al. |
| 8,617,546 B2 | 12/2013 | Kang et al. |
| 8,709,416 B2 | 4/2014 | Langermann et al. |
| 8,728,474 B2 | 5/2014 | Honjo et al. |
| 8,741,295 B2 | 6/2014 | Olive |

(Continued)

FOREIGN PATENT DOCUMENTS

EP     0670369 A2     9/1995
EP     1591527 A1     11/2005

(Continued)

OTHER PUBLICATIONS

Rudikoff et al. Proc Natl Acad Sci USA, 1982, vol. 79, p. 1979.*
Office Action for Chilean Patent Application No. 1871-2016 (dated Feb. 5, 2018).
Demaria et al., "Ionizing Radiation Inhibition of Distant Untreated Tumors (Abscopal Effect) is Immune Mediated," Int. J. Radiation Oncology Biol. Phys., 58(3):862-870 (2004).
Demaria et al., "Immune-Mediated Inhibition of Metastases sfter Treatment with Local Radiation and CTLA-4 Blockade in a Mouse Model of Breast Cancer," Clinical Cancer Research, 11:728-734 (2005).

(Continued)

*Primary Examiner* — Yunsoo Kim
(74) *Attorney, Agent, or Firm* — Fox Rothschild LLP; Aparna G. Patankar

(57) ABSTRACT

The present invention provides stable pharmaceutical formulations comprising a human antibody that specifically binds to human programmed death-1 protein (PD-1). In certain embodiments, the formulations contain, in addition to an anti-PD-1 antibody, a buffer, an amino acid, a nonionic surfactant, and a sugar. The pharmaceutical formulations of the present invention exhibit a substantial degree of antibody stability upon stress and storage.

24 Claims, 9 Drawing Sheets

Specification includes a Sequence Listing.

(56) References Cited

U.S. PATENT DOCUMENTS

| | | | |
|---|---|---|---|
| 8,779,105 B2 | 7/2014 | Korman et al. | |
| 8,779,108 B2 | 7/2014 | Queva et al. | |
| 8,911,726 B2 | 12/2014 | Takahashi et al. | |
| 9,359,437 B2 | 6/2016 | Davis et al. | |
| 2004/0101920 A1 | 5/2004 | Radziejewski et al. | |
| 2005/0226876 A1 | 10/2005 | Graus et al. | |
| 2005/0244403 A1 | 11/2005 | Lazar et al. | |
| 2007/0280945 A1 | 12/2007 | Stevens et al. | |
| 2009/0055944 A1 | 2/2009 | Korman et al. | |
| 2009/0217401 A1 | 8/2009 | Korman et al. | |
| 2009/0232795 A1* | 9/2009 | Condra | C12N 9/6424 424/130.1 |
| 2009/0274666 A1 | 11/2009 | Chen | |
| 2009/0317368 A1 | 12/2009 | Chen | |
| 2010/0203056 A1 | 8/2010 | Irving et al. | |
| 2010/0331527 A1 | 12/2010 | Davis et al. | |
| 2011/0008369 A1 | 1/2011 | Finnefrock et al. | |
| 2011/0171215 A1 | 7/2011 | Davis et al. | |
| 2011/0171220 A1 | 7/2011 | Davis | |
| 2011/0177088 A1 | 7/2011 | Olive et al. | |
| 2011/0195454 A1 | 8/2011 | McWhirter et al. | |
| 2012/0027759 A1 | 2/2012 | Chen et al. | |
| 2012/0121634 A1 | 5/2012 | Chen et al. | |
| 2013/0017199 A1 | 1/2013 | Langermann | |
| 2013/0022595 A1 | 1/2013 | Rotem-Yehudar et al. | |
| 2013/0034559 A1 | 2/2013 | Queva et al. | |
| 2013/0045200 A1 | 2/2013 | Irving et al. | |
| 2013/0045201 A1 | 2/2013 | Irving et al. | |
| 2013/0045202 A1 | 2/2013 | Irving et al. | |
| 2013/0095098 A1 | 4/2013 | Tyson | |
| 2013/0108651 A1 | 5/2013 | Carven et al. | |
| 2013/0109843 A1 | 5/2013 | Carven et al. | |
| 2013/0122014 A1 | 5/2013 | Korman et al. | |
| 2013/0164294 A1 | 6/2013 | Honjo et al. | |
| 2013/0291136 A1 | 10/2013 | Freeman et al. | |
| 2013/0303250 A1 | 11/2013 | Moore | |
| 2014/0088295 A1 | 3/2014 | Smith et al. | |
| 2014/0212422 A1 | 7/2014 | Korman et al. | |
| 2014/0234296 A1 | 8/2014 | Sharma et al. | |
| 2014/0243504 A1 | 8/2014 | Davis et al. | |
| 2014/0271684 A1 | 9/2014 | Li et al. | |
| 2014/0308299 A1 | 10/2014 | Allison et al. | |
| 2015/0166661 A1 | 6/2015 | Chen et al. | |
| 2015/0203579 A1 | 7/2015 | Papadopoulos et al. | |
| 2015/0203580 A1 | 7/2015 | Papadopoulos et al. | |
| 2015/0266966 A1 | 9/2015 | Smith et al. | |
| 2016/0075777 A1 | 3/2016 | Carayon et al. | |
| 2016/0311903 A1 | 10/2016 | West et al. | |
| 2017/0008951 A1 | 1/2017 | Block et al. | |
| 2017/0174779 A1 | 6/2017 | Varghese et al. | |

FOREIGN PATENT DOCUMENTS

| | | |
|---|---|---|
| EP | 1210424 B1 | 2/2007 |
| EP | 2161336 A1 | 3/2010 |
| EP | 2172219 A1 | 4/2010 |
| EP | 2206517 A1 | 7/2010 |
| EP | 1537878 B1 | 9/2010 |
| EP | 2262837 A2 | 12/2010 |
| EP | 1576014 B1 | 6/2011 |
| EP | 2418278 A2 | 2/2012 |
| EP | 2468765 A1 | 6/2012 |
| EP | 2504028 A2 | 10/2012 |
| EP | 2535354 A1 | 12/2012 |
| EP | 1297135 B1 | 1/2013 |
| JP | 2006-340714 A | 12/2006 |
| WO | 99/058572 A1 | 11/1999 |
| WO | 01/39722 A2 | 6/2001 |
| WO | 02/078731 A1 | 10/2002 |
| WO | 03/042402 A2 | 5/2003 |
| WO | 2004/056875 A1 | 7/2004 |
| WO | 2005/103081 A2 | 11/2005 |
| WO | 2006/121168 A1 | 11/2006 |
| WO | 2007/002223 A2 | 1/2007 |
| WO | 2007/005874 A2 | 1/2007 |
| WO | 2007/093630 A1 | 8/2007 |
| WO | 2008/156712 A1 | 12/2008 |
| WO | 2009/024531 A1 | 2/2009 |
| WO | 2009/101611 A1 | 8/2009 |
| WO | 2009/114335 A2 | 9/2009 |
| WO | 2010/029434 A1 | 3/2010 |
| WO | 2010/029435 A1 | 3/2010 |
| WO | 2010027423 A2 | 3/2010 |
| WO | 2010/036959 A2 | 4/2010 |
| WO | 2010/077634 A1 | 7/2010 |
| WO | 2010/089411 A2 | 8/2010 |
| WO | 2011/066342 A2 | 6/2011 |
| WO | 2011/066389 A1 | 6/2011 |
| WO | 2011/110604 A1 | 9/2011 |
| WO | 2011/110621 A1 | 9/2011 |
| WO | 2012/145493 A1 | 10/2012 |
| WO | 2012135408 A1 | 10/2012 |
| WO | 2013/014668 A1 | 1/2013 |
| WO | 2013/019906 A1 | 2/2013 |
| WO | 2013063510 A1 | 5/2013 |
| WO | 2013/079174 A1 | 6/2013 |
| WO | 2013/079945 A1 | 6/2013 |
| WO | 2013/166500 A1 | 11/2013 |
| WO | 2013/169693 A1 | 11/2013 |
| WO | 2013/173223 A1 | 11/2013 |
| WO | 2013/181452 A1 | 12/2013 |
| WO | 2014/055648 A1 | 4/2014 |
| WO | 2014/066834 A1 | 5/2014 |
| WO | 2014/127917 A1 | 8/2014 |
| WO | 2014/151006 A2 | 9/2014 |
| WO | 2014/159562 A1 | 10/2014 |
| WO | 2014/179664 A2 | 11/2014 |
| WO | 2014177568 A1 | 11/2014 |
| WO | 2014/194293 A1 | 12/2014 |
| WO | 2014/209804 A1 | 12/2014 |
| WO | 2015/009856 A2 | 1/2015 |
| WO | 2015/016718 A1 | 2/2015 |
| WO | 2015/026634 A1 | 2/2015 |
| WO | 2015/026684 A1 | 2/2015 |
| WO | 2015/042246 A1 | 3/2015 |
| WO | 2015/048312 A1 | 4/2015 |
| WO | 2015048520 A1 | 4/2015 |
| WO | 2015080513 A1 | 6/2015 |
| WO | 2015/112800 A1 | 7/2015 |
| WO | 2015112900 A1 | 7/2015 |
| WO | 2015/193352 A1 | 12/2015 |
| WO | 2015200119 A1 | 12/2015 |
| WO | 2016061142 A1 | 4/2016 |
| WO | 2016168716 A1 | 10/2016 |

OTHER PUBLICATIONS

Lugade et al., "Local Radiation Therapy of B16 Melanoma Tumors Increases the Generation of Tumor Antigen-Specific Effector Cells That Traffic to the Tumor," J. Immunol, 174:7516-7523 (2005).

Dewan et al., "Fractionated but Not Single-Dose Radiotherapy Induces an Immune-Mediated Abscopal Effect when Combined with Anti-CTLA-4 Antibody," Clin. Cancer Res., 15(17):5379-5388 (2009).

Kachikwu et al., "Radiation Enhances Regulatory T Cell Representation," Int. J. Radiation Oncology Biol. Phys., 81(4): 1128-1135 (2011).

Postow et al., "Immunologic Correlates of the Abscopal Effect in a Patient with Melanoma," The New England Journal of Medicine, 366:925-931 (2012).

Kalbasi, "Radiation and immunotherapy: a synergistic combination," The Journal of Clinical Investigation, 123(7):2756-2763 (2013).

Deng et al., "Irradiation and anti-PD-L1 treatment synergistically promote antitumor immunity in mice," The Journal of Clinical Investigation, 124(2):687-695 (2014).

Sharabi et al., "Stereotactic Radiation Therapy Augments Antigen-Specific PD-1 Mediated Anti-Tumor Immune Responsess via Cross-Presentation of Tumor Antigen," Cancer Immunol Res, 3:345-355 (2014).

(56) References Cited

OTHER PUBLICATIONS

Crittenden et al., "Current Clinical Trials Testing Combinations of Immunotherapy and Radiation," Seminars in Radiation Oncology, 25:54-64 (2015).
Park et al., "PD-1 Restrains Radiotherapy-Induced Abscopal Effect", Cancer Immunol Res, 3(6):610-619 (2015).
Victor et al., "Radiation and dual checkpoint blockade activate non-redundant immune mechanisms in cancer," Nature, 520(7547):373-377 (2015).
Golden et al, "Local radiotherapy and granulocyte-macrophage colony-stimulating factor to generate abscopal responses in patients with metastatic solid tumours: a proof-of-principle trial", Lancet Oncl., 16:795-803 (2015).
Schoenhals et al., "Preclinical Rationale and Clinical Considerations for Radiotherapy Plus Immunotherapy: Going Beyond Local Control", The Cancer Journal, 22:130-137 (2016).
Bernstein et al., "Immunotherapy and stereotactic ablative radiotherapy (ISABR): a curative approach?", Nature Reviews, Clinical Oncology, 3:516-524 (2016).
Rodriguez-Ruiz et al., "Abscopal Effects of Radiotherapy Are Enhanced by Combined Immunostimulatory mAbs and Are Dependent on CD8 T Cells and Crosspriming", Cancer Res., 76:5994-6005 (2016).
Wang et al., "Suppression of type I IFN signaling in tumors mediates resistance to anti-PD-1 treatment that can be overcome by radiotherapy", Cancer Res., 77(4):839-850 (2016).
Vanpouille-Box, "Towards precision radiotherapy for use with immune checkpoint blockers", Clin. Cancer Res., clincanres.0037.2017 (2017).
Weichselbaum et al., "Radiotherapy and immunotherapy: a beneficial liaison?", Nat Rev Clin Oncol, 14(6):365-379 (2017).
Pearson, "Flexible Sequence Similarity Searching with the FASTA3 Program Package," Methods Mol Biol, 132:185-219 (2000).
Shields et al., "Lack of Fucose on Human IgG1 N-Linked Oligosaccharide Improves Binding to Human FcγRIII and Antibody-dependent Cellular Toxicity," J. Biol. Chem., 277(30):26733-26740 (Jul. 26, 2002).
Borradori et al., "Rescue therapy with anti-programmed cell death protein 1 inhibitors (PD-1) of advanced cutaneous squamous cell carcinoma and basosquamous carcinoma: preliminary experience in 5 cases," Br J Dermatol., 175(6): 1382-1386 (2016).
Change et al., "A Case Report of Unresectable Cutaneous Squamous Cell Carcinoma Responsive to Pembrolizumab, a Programmed Cell Death Protein 1 Inhibitor," JAMA Dermatology, Letters: E1-E3 (2015).
Crammer et al., "Treatment of Unresectable and Metastatic Cutaneous Squamous Cell Carcinoma," The Oncologist 15:1320-1328 (2010).
Degache et al., "Major response to pembrolizumab in two patients with locally advanced cutaneous squamous cell carcinoma," JEADV, Letter to the Editor: 1-2 (2017).
Falchook et al., "Responses of melastatic basal cell and cutaneous squamous cell carcinomas to anti-PD1 monoclonal antibody REGN2810," J Immunother Cancer, 4(70):1-5 (2016).
Papadopoulos et al., "REGN2810, A Human Anti-PD-1 Monoclonal Antibody, for Patients with Unresectable Locally Advanced or Metastatic Cutaneous Squamous Cell Carcinoma (CSCC): Initial Safety and Efficacy," ASCO Annual Meeting (2017).
Fisher et al., "Suppressor T Lymphocytes Control the Development of Primary Skin Cancers in Ultraviolet-Irradiated Mice," Science, 216(4):1133-1134 (1982).
Freeman et al., "Comparative Immune Phenotypic Analysis of Cutaneous Squamous Cell Carcinoma and Intraepidermal Carcinoma in Immune-Competent Individuals: Proportional Representation of CD8+ T-Cells but Not FoxP3+ Regulatory T-Cells Is Associated with Disease Stage," PLOS One 9(10), e110928:1-9 (2014).
Mavropoulos et al., "Prospects for personalized targeted therapies for cutaneous squamous cell carcinoma," Seminars in Cutaneous Medicine and Surgery, 33:72-75 (2014).

Muhleisen et al., "Progression of cutaneous squamous cell carcinoma in immunosuppressed patients is associated with reduced CD123+ and FOXP3+ cells in the perineoplastic inflammatory infiltrate," Histopathology, 55:67-76 (2009).
Pickering et al., "Mutational landscape of aggressive cutaneous squamous cell carcinoma," Clin Cancer Res., 20(24): 6582-6592 (2014).
Schaper et al., "The Pattern and Clinicopathological Correlates of PD-L1 Expression in Cutaneous Squamous Cell Carcinoma," Running head: PD-L1 expression in cutaneous squamous cell carcinoma, Research Letter (2016).
Slater et al., "PD-L1 expression in cutaneous squamous cell carcinoma correlates with risk of metastasis," Knoxville Dermatopathology Laboratory, J Cutan Path, 43(8):663-70 (2016).
Soura et al., "Programmed cell death protein-1 inhibitors for immunotherapy of advanced nonmelanoma skin cancer: showing eariy promise," British Journal of Dermatology 175(6):1150-1151 (2016).
Stevenson et al., "Expression of Programmed Cell Death Ligand in Cutaneous Squamous Cell Carcinoma and Treatment of Locally Advanced Disease With Pembrolizumab," JAMA Dermatol., 153(4):299-303 (2017).
Tran et al., "Follow-up on Programmed Cell Death 1 Inhibitor for Cutaneous Squamous Cell Carcinoma," JAMA Dermatology, Letters: E1-E3 (2016).
Anonymous, "Clinical Trails Register: A Phase I Study to Assess Safety and Tolerability of REGN 1979, an anti-CD20 x anti-CD3 bispecific monoclonal antibody, and REGN2810, and anti-programmed death-1 (PD-1) monoclonal antibody, in Patients with B-cell Malignancies," p. 1, section A.3: p. 3, section E.1 [Retrieved from the Internet Mar. 14, 2017: <URL: https://www.clinicaltrailsregister.eu/ctr-search/trial/2015-001697-17/ES>].
Anonymous, "Study of REGN2810 and REGN 1979 in Patients with Lymphoma or Acute Lymphoblastic Leukemia." [Retrieved from the Internet Mar. 15, 2017: <URL: https://www.api.liveclinicaltrials.com/trialpage?state=Maryland&conditions=lymphoma&id=207048402254>].
International Search Report and Written Opinion for PCT/US2016/068030 (dated May 26, 2017).
Study of REGN2810 and REGN1979 in Patients with Lymphoma or Acute Lymphoblastic Leukemia, retrieved from the internet: https://api.liveclinicaltrials.com/trialpage?dcn=10963&city=Baltimore&country=UnitedStates&start=20&state=Maryland&conditions=lymphoma&id=207048402254, 1 page (last updated Nov. 16, 2016).
A Phase 1 Study ot Access Safety and Tolerability of REGN1979, an anti-CD20 x anti-CD3 bispecific monoclonal antibody, and REGN2810, an anti-programmed death-1 (PD-1) monoclonal antibody, EU Clinical Trials Register, https://www.clinicaltrialsregister.eu/ctr-search/search?query=2015-001697-17, 3 pages (Start Date: Dec. 1, 2015).
Study of REGN2810 and REGN1979 in Patients with Lymphoma or Acute Lymphoblastic Leukemia, Smart Patients, https://www.smartpatients.com/trials/NCT02651662, 3 pages (Start Date: Nov. 2015).
Opposition for Colombian Patent Application No. NC2016/0000106 (mailed May 2017).
Topalian et al., Safety, activity, and immune correlates of anti-PD-1 antibody in cancer, The New England Journal of medicine: 366, 26: 2443-2454 (2012).
Anonymous, Safety, activity, and immune correlates of anti-PD-1 antibody in cancer, https://clinicaltrials.gov/archive/NCT02383212/2016_05_02 (2016).
Ahmed et al., Clinical outcomes of melanoma brain metastases treated with stereotactic radiation and anti-PD-1 therapy, Annals of Oncology 27, 3: 434-441 (2015).
Mohiuddin et al., High-Dose Radiation as a Dramatic, Immunological Primer in Locally Advanced Melanoma, CUREUS (2015).
Park et al., PD-1 Restrains Radiotherapy-Induced Abscopal Effect, Cancer Immunology research, 3, 6: 610-619 (2015).
Liniker et al., Safety and Activity of Combined Radiation Therapy (RT) and Anti-PD-1 Antibodies (PD-1) in Patients (pts) With Metastatic Melanoma, International Journal of Radiation: Oncology biology Phsics, 93, 3: E635 (2015).

(56) References Cited

OTHER PUBLICATIONS

Ramesh Rengan et al., Radiation Therapy Contraindications and Safety Panel: Re-irradiation, Novel Combination Therapies, and Hypofractionation, https://www.astro.org/uploadedFiles/_MAIN_SITE_Meeting_and_Education/Events_(ASTRO)/2016/Sample_ASTRO_Meeting/Content_Pieces/RTPatnelCombined.pdf:31-32 (2016).
International Search Report for PCT/US2017/032397, dated Jul. 11, 2017.
International Search Report for PCT/US2017/032408, dated Jul. 6, 2017.
Anonymous, NCT02760498: A Ogase 2 Study of REGN2810, a Fully Human Monoclonal Antibody to Programmed Death-1 (PD-1), in Patients With Advanced Cutaneous Squamous Celli Carcinoma, ClinicalTrials.gov archive, https://clinicaltrials.gov/archive/NCT02760498/2016_05_02 (2016).
Mahoney et al, The Next Immune-Checkpoint Inhibitors: PD-1/PD-L1 Blockade in Melanoma, Clinical Therapeutics, 37, 4: 764-782 (2015).
ESMO 2014: Results of a Phase III Randomised Study of Nivolumab in Patients with Advanced Melanoma After Prior Anti-CTLA4 Therapy, European Society for Medical Oncology (2014).
Reddy, M. et al., "Elimination of Fc Receptor-Dependent Effector Functions of a Modified IgG4 Monoclonal Antibody to Human CD4," J. Immunol, vol. 164, pp. 1925-1933 (2000).
Reineke, U., "Antibody Epitope Mapping Using Arrays of Synthetic Peptides," Methods in Molecular Biology, vol. 248: Antibody Engineering: Methods and Protocols, pp. 443-463 (2004).
Rennert, P., "Last Week's Immune Checkpoint Papers in Nature are Complicated!," SugarCone Biotech, htt://www.sugarconebiotech.com/?p=814, pp. 1-4 (Dec. 4, 2014).
Ribas, A., "Tumor Immunotherapy Directed at PD-1," The New England Journal of Medicine, vol. 366, No. 26, pp. 2517-2519 (Jun. 28, 2012).
Riley, J., "PD-1 signaling in Primary T cells," Immunol. Rev., vol. 229, No. 1, pp. 114-125 (May 2009).
Schalper, K. et al., "In situ Tumor PD-L1 mRNA expression is associated with increased TILs and better outcome in breast carcinomas," Clinical Cancer Research, Author Manuscript Published OnlineFirst on Mar. 19, 2014; DOI: 10.1158/1078-0432.CCR-13-2702.
Sheridan, C., "Cautious optimism surrounds early clinical data for PD-1 blocker," Nature Biotechnology, vol. 30, No. 8, pp. 729-730 (Aug. 2012).
Shetty, R. et al., "PD-1 blockade during chronic SIV infection reduces hyperimmune activation and microbial translocation in rhesus macaques," The Journal of Clinical Investigation, vol. 122, No. 5, pp. 1712-1716 (May 2012).
Shields, R. et al., "Lack of Fucose on Human IgG1N-Linked Oligosaccharide Improves Binding to Human FcyRIII and Antibody-dependent Cellular Toxicity," J. Biol. Chem., vol. 277, No. 30, pp. 26733-26740 (Jul. 26, 2002).
Sznol, M. et al., "Antagonist Antibodies to PD-1 and B7-H1 (PD-L1) in the Treatment of Advanced Human Cancer," Clinical Cancer Research, vol. 19, No. 5, pp. 1021-1034 (Mar. 1, 2013).
Topalian S., slides presented at MMS Annual Education Program May 9-11, 2013 in Boston MA.
Topalian, S. et al., "Targeting the PD-1/B7-H1(PD-L1) pathway to activate anti-tumor immunity," Current Opinion in Immunology, vol. 24, pp. 207-212 (2012).
Tumeh, P. et al., "PD-1 blockade induces responses by inhibiting adaptive immune resistance," Nature, vol. 515, pp. 568-571 (Nov. 27, 2014).
Tutt, A. et al., "Trispecific F(ab')3 derivatives that use cooperative signaling via the TCR/CD3 complex and CD2 to activate and redirect resling cytotoxic T cells," J. Immunol, vol. 147, No. 1, pp. 60-69 (Jul. 1, 1991).
Vajdos, F. et al., "Comprehensive Functional Maps of the Antigen-binding Site of an Anti-ErbB2 Antibody Obtained with Shotgun Scanning Mutagenesis," J. Mol. Biol., vol. 320, pp. 415-428 (2002).

Wang, X.F. et al., "PD-1/PDL1 and CD28/CD80 pathways modulate natural killer T cell function to inhibit hepatitis B virus replication," Journal of Viral Hepatitis, vol. 20 (Suppl. 1), pp. 27-39 (2013).
Watanabe, N. et al., "Coinhibitory Molecules in Autoimmune Diseases," Clinical and Developmental Immunology, vol. 2012, Article ID 269756, 7 pages, doi: 10.1155/2012/269756.
Weder, J., "Immune Checkpoint Proteins: A New Therapeutic Paradigm for Cancer-Preclinical Background: CTLA-4 and PD-1 Blockade," Semin Oncol. vol. 37, pp. 430-439 (2010).
Wu, G. et al., "Receptor-mediated in Vitro Gene Transformation by a Soluble DNA Carrier System," J. Biol. Chem., vol. 262, No. 10, pp. 4429-4432 (Apr. 5, 1987).
Zeng, J. et al., "Anti-PD-1 Blockade and Stereotactic Radiation Produce Long-Term Survival in Mice with Intractranial Cliomas," International Journal of Radiation Oncology, vol. 86, No. 2, pp. 1-7 (2013).
Zielinski, C. et al., "Rationale for targeting the immune system through checkpoint molecule blockade in the treatment of non-small-cell lung cancer," Annals of Oncology, vol. 24, No. 5, pp. 1170-1179 (May 2013).
Zou, W. et al., "Inhibitory B7-family molecules in teh tumour microenvironment," Nature Reviews Immunology, vol. 8, pp. 467-477 (Jun. 2008).
Da Silva, "Anti-PD-1 monoclonal antibody Cancer immunotheraphy", Drugs of the future; 39(1):15-24 (Jan. 1, 2014).
International Search Report and Written Opinion dated Jul. 10, 2015, for corresponding International Patent Application Serial No. PCT/US2015/012589.
Keir et al., "Programmed Death-1 (PD-1): PD-Ligand 1 Interactions Inhibit TCR-Mediated Positive Selection of Thymocyles"; The Journal of Immunology; 175(11):7372-7379 (Dec. 1, 2005).
Riella et al., "Role of the PD-1 Pathway in the Immune Response"; American Journal of Transplantation, 12(10):2575-2587 (Oct. 2012).
Zoran et al., "Programmed death (PD-1) lymphocytes and ligand (PD-L1) in colorectal cancer and their relationship to microsatellite instability status"; J Clin Oncol; 32(5s)(abstr 3625), 2 pgs (May 30, 2014), downloaded from the web on Feb. 7, 2015 http://meetinglibrary.asco.org/content/133958-144.
Al-Lazikani, B. et al., "Standard Conformations for the Canonical Structures of Immunoglobulins," J. Mol. Biol., vol. 273, pp. 927-948 (1997).
Altschul, S. et al., "Basic Local Alignment Search Tool," J. Mol. BioL, vol. 215, po. 403-410 (1990).
Altschul, S. et al., "Gapped BLAST and PSI-BLAST: a new generation of protein database search programs," Nucleic Acids Research, vol. 25, No. 17, pp. 3389-3402 (1997).
Arruebo, M. et al., "Antibody-Conjugated Nanoparticles for Biomedical Applications," Journal of Nanomaterials, vol. 2009, Article ID 439389, 24 pages, doi: 10.1155/2009/439389 (2009).
Badoual, C. et al., "PD-1-Expressing Tumor-Infiltrating T Cells are a Favorable Prognostic Biomarker in HPV-Associated Head and Neck Cancer," Cancer Research, vol. 73, No. 1, pp. 128-138 (Jan. 1, 2013).
Brahmer, J. et al., "Safety and Activity of Ati-PD-L1 Antibody in Patients with Advanced Cancer," The New England Journal of Medicine, vol. 366, No. 26, pp. 2455-2465 (Jun. 28, 2012).
Brusa, D. et al., "The PD-1/PD-L1 axis contributes to T cell dysfunction in chronic lymphocytic leukemia," Haematologica 2012 [Epub ahead of print], 48 pages (2012).
Chattopadhyay, K., "Sequence, structure, funclion, immunity: structural genomics of costimulation," Immunol. Rev., vol. 229, No. 1, pp. 356-386 (May 2009).
Chen, D. et al., "Molecular Pathways: Next-Generation Immunotherapy-Inhibiting Programmed Death-Ligand 1 and Programmed Death-1," Clinical Cancer Research, vol. 18, No. 24, pp. 6580-6587 (Dec. 15, 2012).
Chen, L. et al., "Molecular mechanisms of T cell co-stimulation and co-inhibilion," Nature Rev Immunol., vol. 13, pp. 227-242 (Apr. 2013) NIH Public Access Author Manuscript; available in PMC Apr. 1, 2014.

(56) References Cited

OTHER PUBLICATIONS

Dong, H. et al., "B7-H1, a third member of the B7 family, co-stimulates T-cell proliferation and interleukin-10 secretion," Nature Medicine, vol. 5, No. 12, pp. 1365-1369 (Dec. 1999).
Eggermont, A. et al., "Smart therapeutic strategies in immune-oncology," Nat. Rev. Clin. Oncol., Advance Online Publication, pp. 1-2 (Mar. 4, 2014).
Ehring, H., "Hydrogen Exchange/Electrospray Ionization Mass Spectrometry Studies of Structural Features of Proteins and Protein/Protein Interactions," Analytical Biochemistry, vol. 267, pp. 252-259 (1999).
Eisenhauer, E.A. et al., "New response evaluation criteria in solid tumours: Revised RECIST guideline (version 1.1)," European Journal of Cancer, vol. 45, pp. 228-247 (2009).
Engen, J. et al., "Investigation protein structure and dynamics by hydrogen exchange MS," Analytical Chemistry, vol. 73, No. 9, pp. 256A-265A (May 1, 2001).
Fife, B. et al., "The role of the PD-1 pathway in autoimmunity and peripheral tolerance," Ann. N.Y. Acad. Sci., vol. 1217, pp. 45-59 (2011).
Files, D. et al., "Blockade of the B7-H1/PD-1 Pathway for Cancer Immunotherapy," Yale Journal of Biology and Medicine, vol. 84, pp. 409-421 (2011).
Francisco, L. et al., "The PD-1 Pathway in Tolerance and Autoimmunity," Immunol. Rev. vol. 236, pp. 219-242 (Jul. 2010).
Freeman, G., "Structures of PD-1 with its ligands: Sideways and dancing cheek to cheek," PNAS, vol. 105, No. 30, pp. 10275-10276 (Jul. 29, 2008).
GenBank Accession No. NP_005009 Mar. 15, 2015.
GenBank Accession No. NP_005182 Mar. 15, 2015.
GenBank Accession No. NP_009192 Mar. 15, 2015.
GenBank Accession No. NP_054862 Sep. 25, 2015.
Gonnet, G. et al., "Exhaustive Matching of the Entire Protein Sequence Database," Science, vol. 256, pp. 1443-1445 (Jun. 5, 1992).
Hamid, O. et al., "Anti-programmed death-1 and anti-prgrammed death-ligand 1 antibodies in cancer therapy," Expert Opin. Biol. Ther. [Early Online), pp. 1-15 (Copyright 2013).
Herbst, R. et al., "Predictive correlates of response to the anti-PD-L1 antibody MPDL3280A in cancer patients," Nature, vol. 515, pp. 563-567 (Nov. 27, 2014).
Hochleitner, E. et al., "Characterization of a discontinuous epitope of the human immunodeficiency virus (HIV) core protein p24 by epitope excision and differential chemical modification followed by mass spectrometric peptide mapping analysis," Protein Science, vol. 9, pp. 487-496 (2000).
Hofmeyer, K. et al., "The PD-1/PD-L1 (B7-H1) Pathway in Chronic Infection-Induced Cytotoxic T Lymphocyte Exhaustion," Journal of Biomedicine and Biotechnology, vol. 2011, Article ID 451694, 9 pages, doi:10.1155/2011/451694 (Copyright 2011).
International Search Report and Written Opinion for Application No. PCT/US2015/012595 dated Apr. 14, 2015.
Junghans, R.P. et al., "Anti-Tac-H, a Humanized Antibody to the Interleukin 2 Receptor with New Features for Immunotherapy in Malignant and Immune Disorders," Cancer Research, vol. 50, pp. 1495-1502 (1990).
Kabat, "Sequences of Proteins of Immunological Interest," National Institutes of Health, vol. 1, Bethesda, Md. (1991).
Kasagi, S. et al., "PD-1 and Autoimmunity," Critical Reviews™ in Immunology, vol. 31, No. 4, pp. 265-295 (2011).
Kazane, S. et al., "Self-Assembled Antibody Multimers through Peptide Nucleic Acid Conjugation," J. Am. Chem. Soc., vol. 135, pp. 340-346 (2013) published Dec. 4, 2012.
Klein, C. et al., "Progress in overcoming the chain association issue in bispecific heterodimeric IgG antibodies," mAbs, vol. 4, No. 6, pp. 653-663 (Nov./Dec. 2012).
Kufer, P. et al., "A revival of bispecific antibodies," Trends in Biotechnology, vol. 22, No. 5, pp. 238-244 (May 2004).
Langer, R., "New Methods of Drug Delivery," Science, vol. 249, pp. 1527-1533 (Sep. 28, 1990).
Lin, D. et al., "The PD-1/PD-L1 complex resembles the antigen-binding Fv domains of antibodies and T cell receptors," PNAS, vol. 105, No. 8, pp. 3011-3016 (Feb. 26, 2008).
Lipson, E. et al., "Durable Cancer Regression Off-Treatment and Effective Reinduction Therapy with an Anti-PD-1 Antibody," Clinical Cancer Research, vol. 19, No. 2, pp. 462-468 (Jan. 15, 2013).
Martin, A. et al., "Modeling antibody hypervariable loops: A combined algorithm," Proc. Natl. Acad. Sci. USA, vol. 86, pp. 9268-9272 (Dec. 1989).
Nishino, M. et al., "Developing a Common Language for Tumor Response to Immunotherapy: Immune-Related Response Criteria Using Unidimensional Measurements," Clinical Cancer Research, vol. 19, No. 14, pp. 3936—(Jul. 15, 2013).
Padlan, E. et al., "Identification of specificity-determining residues in antibodies," FASEB J, vol. 9, pp. 133-139 (Jan. 1995).
Pardoll, D., "The blockade of immune checkpoints in cancer immunotherapy," Nature Reviews Cancer, vol. 12, pp. 252-264 (Apr. 2012).
Pearson, W., "Chapter 26. Using the FASTA Program to Search Protein and DNA Sequence Databases," Methods in Molecular Biology, vol. 24: Computer Analysis of Sequence Data, Part 1, pp. 307-331 (1994).
Peggs, K. et al., "PD-1 blockade: promotion endogenous anti-tumor immunity," Expert Rev. Anticancer Ther., vol. 12, No. 10, pp. 1279-1282 (2012).
Peng, W., "PD-1 Blockade Enhances T-clell Migration to Tumors by Elevating IFN-y Inducible Chemokines," Cancer Res., vol. 72, No. 20, pp. 5209-5218 (Published OnlineFirst Aug. 20, 2012).
Postow, M. et al., "Targeting Immune Checkpoints: Releasing the Restraints on Anti-tumore Immunity for Patients with Melanoma," Cancer J., vol. 18, No. 2, pp. 153-159 (2012).
Powell, M. et al., "Compendium of Excipients for Parenteral Formulations" PDA Journal of Pharmaceutical & Technology, vol. 52, No. 5, pp. 238-311 (Sep.-Oct. 1998).
Powles, T. et al., "MPDL3280A (anti-PD-L1) treatment leads to clinical activity in metastatic bladder cancer," Nature, vol. 515, pp. 558-562 (Nov. 27, 2014).
Raghuraman, S. et al., "Spontaneous Clearance of Chronic Hepatitis C Virus Infection is Associated with Appearance of Neutralizing Antibodies and Reversal of T-Cell Exhaustion," The Journal of Infectious Diseases, vol. 205, pp. 736-771 (Mar. 1, 2012).
McDermott DF, et al. "PD-1 as a potential target in cancer therapy", Cancer Med., 2013, vol. 2, No. 5, pp. 662-673.
Tsai et al., Human Vaccines & Immunotherapeutics 10: 3111-3116 (2014).
Momtaz et al., Pharmacogenomics and Personalized Medicine 7: 357-365 (2014).
Clinical Trials Register: A Phase 1 Study to Access Safety and Tolerability of REGN1979, and anti-CD20 x anti-CD3 bispecific monoclonal antibody, and REGN2810, an anti-programmed death-1 (PD-1) monoclonal antibody, in Patients with B-cell Malignancies, EU Clinical Trials Register, https://www.clinical trialsregister.eu/ctr-search/trial/2015-001697-17/ES, 8 pages (Oct. 15, 2015).
Third Party Submission Under 37 CFR 1.290 Concise Description of Relevance filed in U.S. Appl. No. 14/603,776 dated Jul. 4, 2016.
Feuchtinger et al., "leukemia Related Co-Stimulation/Co-Inhibition Predict T-Cell Attack of Acute Lymphoblastic Leukemia Mediated by Blinatumomab," Blood, 126:3764 (2015) (Abstract).
Peters et al., "Engineering an Improved IgG4 Molecule with Reduced Disulfide Bond Heterogeneity and Increased Fab Domain Thermal Stability", J Biol Chem (2012), 287(29):24525-24533.
Rouet et al., "Stability engineering of the human antibody repertoire", FEBS Lett (2013), 588(2):269-277.

* cited by examiner

| Formulation | 150 mg/mL mAb1, 10 mM Histidine | | | | | | | | | |
|---|---|---|---|---|---|---|---|---|---|---|
| Fill Volume | 0.4 mL | | | | | | | | | |
| Container/Closure | 2 mL Type 1 borosilicate glass vial with a FluroTec® coated 4432/50 butyl rubber stopper | | | | | | | | | |
| Excipients | pH | Color and Appearance | Turbidity (Increase in OD at 405 nm) | pH | % mAb1 Recovered by RP-UPLC | Purity by SE-UPLC | | | Charged Variants by CEX-UPLC | | |
| | | | | | | % HMW | % Native | % LMW | % Acidic | % Main | % Basic |
| Starting Material[a1] | - | Pass | 0.00 | - | 100 | 3.4 | 96.1 | 0.5 | 26.2 | 48.9 | 24.9 |
| - | 5.3 | Fail | | | | Sample Gelled | | | | | |
| | 5.6 | Fail | | | | Sample Gelled | | | | | |
| | 5.9 | Fail | 0.40 | 5.8 | 95 | 49.3 | 49.9 | 0.8 | 32.5 | 39.1 | 28.4 |
| | 6.0 | Fail | 0.51 | 6.0 | 99 | 44.1 | 55.0 | 0.9 | 36.9 | 41.9 | 21.3 |
| | 6.4 | Fail | 0.65 | 6.3 | 98 | 38.1 | 61.0 | 0.9 | 45.9 | 34.8 | 19.4 |
| 9% Sucrose | 5.3 | Pass | 0.14 | 5.3 | 95 | 46.9 | 52.4 | 0.7 | 33.7 | 37.6 | 28.6 |
| | 5.5 | Pass | 0.16 | 5.5 | 99 | 34.9 | 64.2 | 0.9 | 35.7 | 36.3 | 28.0 |
| | 5.9 | Pass | 0.13 | 5.8 | 100 | 25.5 | 73.6 | 1.0 | 36.0 | 37.2 | 26.8 |
| | 6.0 | Pass | 0.14 | 6.0 | 99 | 21.9 | 77.1 | 1.0 | 40.0 | 34.5 | 25.5 |
| | 6.4 | Pass | 0.15 | 6.3 | 98 | 19.6 | 79.4 | 1.0 | 48.9 | 26.7 | 24.4 |
| 5% Sucrose 70 mM Arginine | 5.4 | Fail | | | | Sample Gelled | | | | | |
| | 5.6 | Fail | | | | Sample Gelled | | | | | |
| | 5.9 | Fail | | | | Sample Gelled | | | | | |
| | 6.0 | Fail | | | 100 | 45.8 | 53.1 | | | | |
| | 6.4 | Fail | 0.46 | 6.3 | 100 | | | 1.0 | 46.6 | 31.1 | 22.3 |

Figure 1

| Formulation | Formulation Components | | | | | | | | Viscosity (20C) |
|---|---|---|---|---|---|---|---|---|---|
| | RG2810 (mg/mL) | Histidine (mM) | pH | Sucrose (%) | Proline (%) | NaCl (mM) | Mg(OAc)₂ (mM) | Arg-HCl (mM) | PS-80 (%) | |
| 1 | 150 | 10 | 6.0 | 9.0 | | | | | | 10.6 |
| 2 | 150 | 10 | 6.0 | 5.0 | | | | 70.0 | | 8.0 |
| 3 | 150 | 10 | 6.0 | 5.0 | | 70.0 | | | | 7.4 |
| 4 | 150 | 10 | 6.0 | 5.0 | | | 25.0 | | | 7.9 |
| 5 | 150 | 10 | 6.0 | 5.0 | 2.0 | | | | | 9.6 |
| 6 | 150 | 10 | 6.0 | | 3.5 | | | | | 8.3 |
| 7 | 150 | 10 | 6.0 | | 2.0 | | | 70.0 | | 7.1 |
| 8 | 150 | 10 | 6.0 | | 2.0 | 70.0 | | | | 7.2 |
| 9 | 150 | 10 | 6.0 | | 2.0 | | 25.0 | | | 7.2 |
| 10 | 150 | 10 | 6.0 | 9 | | 0 | 0 | 0 | 0.1 | 11.0 |
| 11 | 150 | 10 | 6.0 | 9 | | 25 | | | 0.1 | 10.0 |
| 12 | 150 | 10 | 6.0 | 9 | | 50 | | | 0.1 | 10.2 |
| 13 | 150 | 10 | 6.0 | 9 | | 75 | | | 0.1 | 9.4 |
| 14 | 150 | 10 | 6.0 | 9 | | 100 | | | 0.1 | 9.7 |
| 15 | 150 | 25 | 6.0 | 9 | | | | | 0.1 | 10.6 |
| 16 | 150 | 50 | 6.0 | 9 | | | | | 0.1 | 10.3 |
| 17 | 150 | 75 | 6.0 | 9 | | | | | 0.1 | 10.1 |
| 18 | 150 | 100 | 6.0 | 9 | | | | | 0.1 | 9.8 |
| 19 | 150 | 10 | 6.0 | 9 | | | | | 0.1 | 10.8 |
| 20 | 150 | 10 | 6.0 | 9 | | | 10 | | 0.1 | 10.3 |
| 21 | 150 | 10 | 6.0 | 9 | | | 25 | | 0.1 | 9.9 |
| 22 | 150 | 10 | 6.0 | 9 | | | 50 | 25 | 0.1 | 10.0 |
| 23 | 150 | 10 | 6.0 | 9 | | | | 50 | 0.1 | 9.9 |
| 24 | 150 | 10 | 6.0 | 9 | | | | 70 | 0.1 | 10.0 |

Figure 4

| Formulation | | 175 mg/mL mAb1, 10 mM Histidine (except F9 with 25 mM), 0.1% polysorbate 80 | | | | | | | | |
|---|---|---|---|---|---|---|---|---|---|---|
| Fill Volume | | 0.4 mL | | | | | | | | |
| Container/Closure | | 2 mL Type 1 borosilicate glass vial with a FluroTec® coated 4432/50 butyl rubber stopper | | | | | | | | |
| Excipients | Formulation No. | Color and Appearance | Turbidity (Increase in OD at 405 nm) | pH | % mAb1 Recovered by RP-UPLC | Purity by SE-UPLC | | | Charged Variants by CEX-UPLC | | |
| | | | | | | % HMW | % Native | % LMW | % Acidic | % Main | % Basic |
| Starting Material[a1] | - | Pass | 0.00 | 6.1 | 100 | 2.3 | 97.1 | 0.6 | 26.1 | 46.8 | 27.1 |
| 9% sucrose | F1 | Pass | 0.20 | 6.1 | 72 | 51.4 | 48.0 | 0.6 | 28.1 | 44.9 | 27.0 |
| 5% sucrose, 1.5% Proline | F2 | Pass | 0.08 | 6.1 | 94 | 26.6 | 72.6 | 0.8 | 30.0 | 42.9 | 27.1 |
| 5% sucrose, 3.0% Proline | F3 | Pass | 0.06 | 6.1 | 93 | 31.1 | 68.1 | 0.7 | 30.2 | 43.5 | 26.3 |
| 3.0% Proline | F4 | Pass | 0.07 | 6.1 | 93 | 28.9 | 70.3 | 0.8 | 30.4 | 43.3 | 26.3 |
| 5% sucrose, 1.5% Proline 25 mM Argine | F5 | Pass | 0.16 | 6.1 | 88 | 45.5 | 53.9 | 0.6 | 28.7 | 41.9 | 29.4 |
| 5% sucrose, 1.5% Proline 25 mM Mg(OAc)$_2$ | F6 | Pass | 0.13 | 6.1 | 94 | 39.5 | 59.8 | 0.7 | 28.2 | 41.5 | 30.3 |
| 5% sucrose, 1.5% Proline 25 mM NaCl | F7 | Pass | 0.15 | 6.2 | 91 | 41.1 | 58.1 | 0.8 | 32.7 | 35.5 | 31.8 |
| 5% sucrose, 1.5% Proline | F8 | Pass | 0.16 | 6.1 | 84 | 40.4 | 58.9 | 0.7 | 28.7 | 42.0 | 29.3 |
| 5% sucrose, 1.5% Proline 25 mM Histidine | F9 | Pass | 0.13 | 6.1 | 90 | 40.0 | 59.2 | 0.7 | 28.9 | 43.8 | 27.3 |

Figure 5

STABLE ANTIBODY FORMULATION

CROSS-REFERENCE TO RELATED APPLICATIONS

This application claims the benefit under 35 U.S.C. § 119(e) of U.S. provisional application No. 62/482,270, filed on Apr. 6, 2017; the disclosure of which is herein incorporated by reference in its entirety.

FIELD OF THE INVENTION

The present invention relates to the field of therapeutic antibody formulations. More specifically, the present invention relates to the field of pharmaceutical formulations comprising a human antibody that specifically binds to human programmed death-1 (PD-1) protein.

BACKGROUND OF THE INVENTION

Therapeutic macromolecules (e.g., antibodies) must be formulated in a manner that not only makes the molecules suitable for administration to patients, but also maintains their stability during storage and subsequent use. For example, therapeutic antibodies in liquid solution are prone to degradation, aggregation or undesired chemical modifications unless the solution is formulated properly. The stability of an antibody in liquid formulation depends not only on the kinds of excipients used in the formulation, but also on the amounts and proportions of the excipients relative to one another. Furthermore, other considerations aside from stability must be taken into account when preparing a liquid antibody formulation. Examples of such additional considerations include the viscosity of the solution and the concentration of antibody that can be accommodated by a given formulation, and the visual quality or appeal of the formulation. Thus, when formulating a therapeutic antibody, great care must be taken to arrive at a formulation that remains stable, contains an adequate concentration of antibody, and possesses a suitable viscosity as well as other properties which enable the formulation to be conveniently administered to patients.

Antibodies to the human programmed death-1 protein (PD-1) are one example of a therapeutically relevant macromolecule that requires proper formulation. Anti-PD-1 antibodies are clinically useful for the treatment of cancer (e.g., lung cancer, melanoma, and brain cancer) and viral infections and autoimmune diseases. Exemplary anti-PD-1 antibodies are described, inter alia, in U.S. Pat. Nos. 7,101,550, 7,595,048, 7,488,802, 7,563,869, 8,008,449, 8,168,757, and 8,216,996, 20110008369, 20130017199, 20130022595, and in WO2006121168, WO20091154335, WO2012145493, WO2013014668, WO2009101611, EP2262837, and EP2504028. US20140234296 describes lyophilized formulations of an anti-PD-1 antibody.

Although anti-PD-1 antibodies are known, there remains a need in the art for novel pharmaceutical formulations comprising anti-PD-1 antibodies that are sufficiently stable and suitable for administration to patients.

BRIEF SUMMARY OF THE INVENTION

The present invention satisfies the aforementioned need by providing stable pharmaceutical formulations comprising a human antibody that specifically binds to human programmed death-1 protein (PD-1).

In one aspect, a stable liquid pharmaceutical formulation of low viscosity is provided, comprising: (i) a human antibody that specifically binds to human programmed death protein (PD-1); (ii) a buffer; (iii) an organic cosolvent; (iv) a stabilizer; and (v) a viscosity modifier.

In various embodiments, the antibody is provided at a concentration from about 5±0.75 mg/mL to about 250±37.5 mg/mL. In one embodiment, the antibody is provided at a concentration of 12.5 mg/mL±1.85 mg/mL, or about 12.5 mg/mL. In one embodiment, the antibody is provided at a concentration of 25 mg/mL±3.75 mg/mL, or about 25 mg/mL. In another embodiment, the antibody is provided at a concentration of 50 mg/mL±7.5 mg/mL, or about 50 mg/mL. In another embodiment, the antibody is provided at a concentration of 100 mg/mL±15 mg/mL, or about 100 mg/mL. In one embodiment, the antibody is provided at a concentration of 150 mg/mL±22.5 mg/mL, or about 150 mg/mL. In another embodiment, the antibody is provided at a concentration of 175 mg/mL±26.25 mg/mL, or about 175 mg/mL. In another embodiment, the antibody is provided at a concentration of 200 mg/mL±30 mg/mL, or about 200 mg/mL.

In certain embodiments, the formulation comprises any one of the anti-PD-1 antibodies disclosed in US Patent Application Publication No: 20150203579, incorporated herein in its entirety. In certain embodiments, the anti-PD-1 antibody comprises (a) a heavy chain variable region (HCVR) comprising heavy chain complementarity determining regions 1, 2 and 3 (HCDR1-HCDR2-HCDR3) each comprising a sequence of SEQ ID NO: 3, SEQ ID NO: 4 and SEQ ID NO: 5, respectively; and (b) a light chain variable region (LCVR) comprising light chain complementarity determining regions 1, 2 and 3 (LCDR1-LCDR2-LCDR3) each comprising a sequence of SEQ ID NO: 6, SEQ ID NO: 7 and SEQ ID NO: 8, respectively. In one embodiment, the antibody comprises a HCVR comprising the amino acid sequence of SEQ ID NO: 1 and a LCVR comprising the amino acid sequence of SEQ ID NO: 2. In one embodiment, the antibody comprises a heavy chain comprising the amino acid sequence of SEQ ID NO: 9 and a light chain comprising the amino acid sequence of SEQ ID NO: 10. In one embodiment, the antibody comprises a heavy chain comprising the amino acid sequence of SEQ ID NO: 11 and a light chain comprising the amino acid sequence of SEQ ID NO: 10. In one embodiment, the antibody comprises a heavy chain comprising the amino acid sequence selected from the group consisting of SEQ ID NOs: 9 and 11; and a light chain comprising the amino acid sequence of SEQ ID NO: 10. In one embodiment, the antibody comprises a HCVR having 90% sequence identity to SEQ ID NO: 1. In one embodiment, the antibody comprises a LCVR having 90% sequence identity to SEQ ID NO: 2. In one embodiment, the antibody comprises a HCVR having 90% sequence identity to SEQ ID NO: 1 and a LCVR having 90% sequence identity to SEQ ID NO: 2.

In one embodiment, the pH of the liquid formulation is pH 6.0±0.5, pH 6.0±0.4, pH 6.0±0.3, pH 6.0±0.2, pH 6.0±0.1, pH 6.0±0.05, pH 6.0±0.01, or pH 6.0. In one embodiment, the pH of the liquid formulation is about pH 6.0±0.3.

In one embodiment, the buffer comprises histidine. In certain embodiments, the histidine buffer is at a concentration of from 5 mM±1 mM to 50 mM±10 mM, preferably from 5 mM±1 mM to 25 mM±5 mM. In one embodiment, the histidine buffer is at a concentration of 10 mM±2 mM or about 10 mM. In one embodiment, the histidine buffer is at a concentration of 20 mM±4 mM or about 20 mM. In one embodiment, the histidine buffer is at a concentration of 40 nM±8 mM or about 40 nM. In certain embodiments, the histidine buffer comprises L-histidine and L-histidine monohydrochloride monohydrate. In one embodiment, L-histidine is at a concentration of from 2 mM±0.4 mM to 25 mM±5 mM, preferably from 4 mM±0.8 mM to 20 mM±4 mM. In one embodiment, L-histidine monohydrochloride monohydrate is at a concentration of from 2 mM±0.4 mM to 25 mM±5 mM, preferably from 4 mM±0.8 mM to 20 mM±4 mM. In one embodiment, the buffer comprises L-histidine at a concentration of 4.8 mM±0.96 mM and L-histidine monohydrochloride monohydrate at a concentration of 5.2 mM±1.04 mM. In one embodiment, the buffer comprises histidine at a concentration of 10 mM±2 mM, wherein the histidine comprises L-histidine at a concentration of 4.8 mM±0.96 mM and L-histidine monohydrochloride monohydrate at a concentration of 5.2 mM±1.04 mM.

In certain embodiments, the organic cosolvent is a non-ionic polymer containing a polyoxyethylene moiety. In one embodiment, the organic solvent is a surfactant. In some embodiments, the organic cosolvent is any one or more of polysorbate, poloxamer 188 and polyethylene glycol 3350. In one embodiment, the organic cosolvent is polysorbate 80. In one embodiment, the organic cosolvent is polysorbate 20.

In one embodiment, the organic solvent is at a concentration of from about 0.01%±0.005% to about 1%±0.5% "weight to volume" or "w/v", wherein, e.g., 0.1 g/ml=10% and 0.01 g/ml=1%. In certain embodiments, the organic solvent is polysorbate at a concentration of from 0.05%±0.025% to 0.5%±0.25% (w/v). In one embodiment, the organic cosolvent is polysorbate 80, which is at a concentration of 0.2%±0.1% w/v, or about 0.2%. In another embodiment, the organic cosolvent is polysorbate 80, which is at a concentration of 0.1%±0.05% w/v or about 0.1% w/v. In one embodiment, the organic cosolvent is polysorbate 20, which is at a concentration of 0.2%±0.1% w/v, or about 0.2%. In another embodiment, the organic cosolvent is polysorbate 20, which is at a concentration of 0.1%±0.05% w/v or about 0.1% w/v.

In certain embodiments, the stabilizer is a sugar. In one embodiment, the sugar is sucrose. In various embodiments, the stabilizer is at a concentration of from 1%±0.2% w/v to 20%±4% w/v, from 5%±1% w/v to 15%±3% w/v, or from 1%±0.2% to 10%±2% w/v. In one embodiment, the stabilizer is sucrose at a concentration of 5%±1% w/v or about 5% w/v. In another embodiment, the stabilizer is sucrose at a concentration of 9%±1.8% w/v or about 9% w/v. In another embodiment, the stabilizer is sucrose at a concentration of 10%±2% w/v or about 10% w/v.

In one embodiment, the viscosity modifier is an amino acid. In one embodiment, the viscosity modifier is L-proline. In certain embodiments, the viscosity modifier is at a concentration of from 1%±0.2% to 5%±1% w/v. In one embodiment, the viscosity modifier is proline at a concentration of 1.5%±0.3% or about 1.5%. In one embodiment, the viscosity modifier is proline at a concentration of 3%±0.6%, or about 3%.

In certain embodiments, the viscosity of the liquid pharmaceutical formulation at 25° C. is less than or equal to about 15 cPoise±10%. In certain embodiments, the viscosity at 25° C. is between 1.0 cPoise±10% and 20 cPoise±10%. In certain embodiments, the viscosity of the liquid pharmaceutical formulation is ≤15 cPoise. In certain embodiments, the viscosity of the liquid pharmaceutical formulation is ≤20 cPoise. In certain embodiments, the viscosity of the liquid pharmaceutical formulation is ≤10 cPoise. In certain embodiments, the viscosity at 25° C. is 5 cPoise±10%, 6.0 cPoise±10%, 7.0 cPoise±10%, 7.1 cPoise±10%, 7.2 cPoise±10%, 7.9 cPoise±10%, 8.3 cPoise±10%, 9.0 cPoise±10%, 9.6 cPoise±10%, 10.0 cPoise±10%, 10.6 cPoise±10%, 11.4 cPoise±10%, 11.6 cPoise±10%, 11.8 cPoise±10%, 12.0 cPoise±10%, 13.0 cPoise±10%, 14.0 cPoise±10%, 15.0 cPoise±10%, or 16 cPoise±10%.

In one aspect, a stable liquid pharmaceutical formulation of low-viscosity is provided, comprising: (i) from 5±0.75 mg/ml to 250±37.5 mg/ml of a human antibody that specifically binds to human PD-1; (ii) from 0 mM to 40±8 mM histidine buffer; (iii) from 0% to 0.5%±0.25% (w/v) polysorbate 80; (iv) from 0% to 15%±3% (w/v) sucrose; and (v) from 0 to 5%±1% proline, at a pH of from about 5.3 to about 6.7; wherein the anti-PD-1 antibody comprises a heavy chain variable region (HCVR) and a light chain variable region (LCVR) such that the HCVR/LCVR combination comprises heavy and light chain complementarity determining regions (HCDR1-HCDR2-HCDR3/LCDR1-LCDR2-LCDR3), which comprise the amino acid sequences of SEQ ID NOs: 3-4-5/SEQ ID NOs: 6-7-8, respectively. In one embodiment, the anti-PD-1 antibody comprises a heavy chain variable region (HCVR) and light chain variable region (LCVR) comprising an amino acid sequence of SEQ ID NO: 1 and SEQ ID NO: 2, respectively. In certain embodiments, the anti-PD1 antibody comprises a Fc region elected from the group consisting of human IgG1, IgG2, IgG3, and IgG4 isotypes. In one embodiment, the antibody comprises a human IgG4 isotype. In one embodiment, the antibody comprises a heavy chain comprising the amino acid sequence selected from the group consisting of SEQ ID NOs: 9 and 11; and a light chain comprising the amino acid sequence of SEQ ID NO: 10. In one embodiment, the antibody comprises a heavy chain comprising the amino acid sequence of SEQ ID NO: 9 and a light chain comprising the amino acid sequence of SEQ ID NO: 10. In one embodiment, the antibody comprises a heavy chain comprising the amino acid sequence of SEQ ID NO: 11 and a light chain comprising the amino acid sequence of SEQ ID NO: 10. In one embodiment, the antibody has a molecular weight of 143 kDa±5 kDa.

In certain embodiments, a stable, low-viscosity liquid pharmaceutical formulation is provided, comprising: (i) from 5±0.75 mg/ml to 250±37.5 mg/ml of a human antibody that specifically binds to human PD-1; (ii) from 0 mM to 40±8 mM histidine buffer; (iii) from 0% to 0.5%±0.25% (w/v) polysorbate 80; (iv) from 0% to 15%±3% (w/v) sucrose; and (v) from 0 to 5%±1% proline, at a pH of from about 5.3 to about 6.7; wherein the anti-PD-1 antibody comprises a HCVR and a LCVR, wherein the HCVR has 90% sequence identity to SEQ ID NO: 1 and/or the LCVR has 90% sequence identity to SEQ ID NO: 2. In one embodiment, the anti-PD-1 antibody comprises a HCVR comprising the amino acid sequence of SEQ ID NO: 1 and a LCVR comprising the amino acid sequence of SEQ ID NO: 2. In one embodiment, the anti-PD-1 antibody comprises a heavy chain comprising the amino acid sequence selected from the group consisting of SEQ ID NOs: 9 and 11; and a light chain comprising the amino acid sequence of SEQ ID NO: 10.

In certain embodiments, a stable, low-viscosity liquid pharmaceutical formulation is provided, comprising: (i) from 5±0.75 mg/ml to 250±37.5 mg/ml of a human antibody that specifically binds to human PD-1; (ii) from 0 mM to 40±8 mM histidine buffer; (iii) from 0% to 0.5%±0.25% (w/v) polysorbate 80; (iv) from 0% to 15%±3% (w/v) sucrose; and (v) from 0 to 5%±1% proline, at a pH of from about 5.3 to about 6.7; wherein the anti-PD-1 antibody comprises a HCVR and a LCVR, wherein the HCVR comprises an amino acid sequence of SEQ ID NO: 1 having no more than five amino acid substitutions, and wherein the LCVR comprises an amino acid sequence of SEQ ID NO: 2 having no more than two amino acid substitutions. In one embodiment, the anti-PD-1 antibody comprises a HCVR comprising the amino acid sequence of SEQ ID NO: 1 and a LCVR comprising the amino acid sequence of SEQ ID NO: 2. In one embodiment, the anti-PD-1 antibody comprises a heavy chain comprising the amino acid sequence selected from the group consisting of SEQ ID NOs: 9 and 11; and a light chain comprising the amino acid sequence of SEQ ID NO: 10.

In certain embodiments, the formulation of any of the preceding aspects has an attribute selected from the group consisting of: (i) the formulation is stable to long-term storage at 25° C., 5° C., −20° C., −30° C. and −80° C., as described herein; (ii) the formulation is stable to agitation stress as described herein; (iii) the formulation is low-viscosity (viscosity less than 20 cPoise, preferably less than 15 cPoise); (iii) the formulation is stable even with up to ±50% variation in the formulation excipient concentrations, as described herein; (iv) the formulation is iso-osmolar to physiologic conditions; (v) the formulation is stable to and compatible with intravenous delivery devices and procedures; and (vi) the formulation is stable to long-term storage in a glass vial or in a prefilled syringe.

In certain embodiments of this aspect, a stable liquid formulation is provided, comprising: (i) from 5±0.75 mg/ml to 250±37.5 mg/ml of a human antibody that specifically binds to human PD-1; (ii) from 5 mM±1 mM to 20±4 mM histidine buffer; (iii) from 0.05%±0.025% to 0.3%±0.15% (w/v) polysorbate 80; (iv) from 1%±0.2% to 10%±2% (w/v) sucrose; and (v) from 1%±0.2% to 5%±1% proline, at a pH of about 6.0, wherein the antibody comprises a HCVR/LCVR comprising an amino acid sequence pair of SEQ ID NOs: 1/2. In one embodiment, the stable liquid formulation of this aspect has a viscosity less than 15 cP. In one embodiment, z 90% of the antibodies have a molecular weight of 143 kDa±1 kDa. In one embodiment, the pharmaceutical formulation has a viscosity of less than 20 cP, less than 15 cP, or less than 10 cP. In one embodiment, more than 96% of the antibodies have native conformation upon storage for 12 months at 5° C. In one embodiment, at least 97% or more of the antibodies have native conformation upon storage at −80° C., −30° C. &/or −20° C. for 6 months.

In one embodiment of this aspect, the stable liquid formulation comprises (i) 25±3.75 mg/mL of an anti-PD-1 antibody; (ii) 10±2 mM histidine buffer; (iii) 0.2%±0.1% (w/v) polysorbate 80; (iv) 1.5%±0.3% (w/v) proline; and (v) 5%±1% (w/v) sucrose, at a pH of 6.0±0.3, wherein the antibody comprises a HCVR/LCVR comprising an amino acid sequence pair of SEQ ID NOs: 1/2.

In one embodiment of this aspect, the stable liquid formulation comprises (i) 25±3.75 mg/mL of an anti-PD-1 antibody; (ii) 4.8 mM±0.96 mM L-histidine; (iii) 5.2 mM±1.04 mM L-histidine monohydrochloride monohydrate; (iv) 0.2%±0.1% (w/v) polysorbate 80; (v) 1.5%±0.3% (w/v) proline; and (vi) 5%±1% (w/v) sucrose, at a pH of 6.0±0.3, wherein the antibody comprises a HCVR/LCVR comprising an amino acid sequence pair of SEQ ID NOs: 1/2.

In one embodiment of this aspect, the stable liquid formulation comprises (i) 50±7.5 mg/mL of an anti-PD-1 antibody; (ii) 10±2 mM histidine buffer; (iii) 0.2%±0.1% (w/v) polysorbate 80; (iv) 1.5%±0.3% (w/v) proline; and (v) 5%±1% (w/v) sucrose, at a pH of 6.0±0.3, wherein the antibody comprises a HCVR/LCVR comprising an amino acid sequence pair of SEQ ID NOs: 1/2. In one embodiment of this particular formulation, the viscosity is less than 10 cPoise.

In one embodiment of this aspect, the stable liquid formulation comprises (i) 50±7.5 mg/mL of an anti-PD-1 antibody; (ii) 4.8 mM±0.96 mM L-histidine; (iii) 5.2 mM±1.04 mM L-histidine monohydrochloride monohydrate; (iv) 0.2%±0.1% (w/v) polysorbate 80; (v) 1.5%±0.3% (w/v) proline; and (vi) 5%±1% (w/v) sucrose, at a pH of 6.0±0.3, wherein the antibody comprises a HCVR/LCVR comprising an amino acid sequence pair of SEQ ID NOs: 1/2.

In one embodiment, the stable liquid formulation comprises (i) 100±15 mg/mL of an anti-PD-1 antibody; (ii) 10±2 mM histidine buffer; (iii) 0.2%±0.1% (w/v) (w/v) polysorbate 80; (iv) 1.5%±0.3% (w/v) proline; and (v) 5%±1% (w/v) sucrose, at a pH of 6.0±0.3, wherein the antibody comprises a HCVR/LCVR comprising an amino acid sequence pair of SEQ ID NOs: 1/2. In one embodiment of this particular formulation, the viscosity is less than 10 cPoise.

In one embodiment of this aspect, the stable liquid formulation comprises (i) 100±15 mg/mL of an anti-PD-1 antibody; (ii) 4.8 mM±0.96 mM L-histidine; (iii) 5.2 mM±1.04 mM L-histidine monohydrochloride monohydrate; (iv) 0.2%±0.1% (w/v) polysorbate 80; (v) 1.5%±0.3% (w/v) proline; and (vi) 5%±1% (w/v) sucrose, at a pH of 6.0±0.3, wherein the antibody comprises a HCVR/LCVR comprising an amino acid sequence pair of SEQ ID NOs: 1/2.

In one embodiment, the stable liquid formulation comprises (i) 150±22.5 mg/mL of an anti-PD-1 antibody; (ii) 10±2 mM histidine buffer; (iii) 0.2%±0.1% (w/v) polysorbate 80; (iv) 10%±2% (w/v) sucrose; and (v) 1.5%±0.3% (w/v) proline, at a pH of 6.0±0.3, wherein the antibody comprises a HCVR/LCVR comprising an amino acid sequence pair of SEQ ID NOs: 1/2. In one embodiment of this particular formulation, the viscosity is less than 20 cPoise, preferably less than 15 cPoise.

In one embodiment of this aspect, the stable liquid formulation comprises (i) 150±22.5 mg/mL of an anti-PD-1 antibody; (ii) 4.8 mM±0.96 mM L-histidine; (iii) 5.2 mM±1.04 mM L-histidine monohydrochloride monohydrate; (iv) 0.2%±0.1% (w/v) polysorbate 80; (v) 1.5%±0.3% (w/v) proline; and (vi) 5%±1% (w/v) sucrose, at a pH of 6.0±0.3, wherein the antibody comprises a HCVR/LCVR comprising an amino acid sequence pair of SEQ ID NOs: 1/2.

In one embodiment of this aspect, the stable liquid formulation comprises (i) 175±26.25 mg/mL of an anti-PD-1 antibody; (ii) 10±2 mM histidine buffer; (iii) 0.2%±0.1% (w/v) polysorbate 80; (iv) 5%±1% (w/v) sucrose; and (v) 1.5%±0.3% (w/v) proline, at a pH of 6.0±0.3, wherein the antibody comprises a HCVR/LCVR comprising an amino acid sequence pair of SEQ ID NOs: 1/2. In one embodiment of this particular formulation, the viscosity is less than 20 cPoise, preferably less than 15 cPoise.

In one embodiment of this aspect, the stable liquid formulation comprises (i) 175±26.25 mg/mL of an anti-PD-1 antibody; (ii) 4.8 mM±0.96 mM L-histidine; (iii) 5.2 mM±1.04 mM L-histidine monohydrochloride monohydrate; (iv) 0.2%±0.1% (w/v) polysorbate 80; (v) 1.5%±0.3% (w/v) proline; and (vi) 5%±1% (w/v) sucrose, at a pH of 6.0±0.3, wherein the antibody comprises a HCVR/LCVR comprising an amino acid sequence pair of SEQ ID NOs: 1/2.

In one embodiment of this aspect, the stable liquid formulation comprises (i) 200±30.00 mg/mL of an anti-PD-1 antibody; (ii) 10±2 mM histidine buffer; (iii) 0.2%±0.1% (w/v) polysorbate 80; (iv) 5%±1% (w/v) sucrose; and (v) 1.5%±0.3% (w/v) proline, at a pH of 6.0±0.3, wherein the antibody comprises a HCVR/LCVR comprising an amino acid sequence pair of SEQ ID NOs: 1/2. In one embodiment of this particular formulation, the viscosity is less than 20 cPoise.

In one embodiment of this aspect, the stable liquid formulation comprises (i) 200±30.00 mg/mL of an anti-PD-1 antibody; (ii) 4.8 mM±0.96 mM L-histidine; (iii) 5.2 mM±1.04 mM L-histidine monohydrochloride monohydrate; (iv) 0.2%±0.1% (w/v) polysorbate 80; (v) 1.5%±0.3% (w/v) proline; and (vi) 5%±1% (w/v) sucrose, at a pH of 6.0±0.3, wherein the antibody comprises a HCVR/LCVR comprising an amino acid sequence pair of SEQ ID NOs: 1/2.

In one embodiment, after storage of the formulation at 45° for 28 days, z 90% of the antibody is native and z 35% of the antibody is of the main charge form. In one embodiment, after storage of the formulation at 25° for three months, >94% of the antibody is native and z 44% of the antibody is of the main charge form. In one embodiment, after storage of the formulation at 5° for 12 months, >96% of the antibody is native and >50% of the antibody is of the main charge form. In one embodiment, after storage of the formulation at −20° for 12 months, >96% of the antibody is native and >40% of the antibody is of the main charge form. In one embodiment, after storage of the formulation at −30° for 12 months, >96% of the antibody is native and >40% of the antibody is of the main charge form. In one embodiment, after storage of the formulation at −80° for 12 months, >96% of the antibody is native and >40% of the antibody is of the main charge form. In one embodiment, more than 96% of the antibodies have native conformation upon storage for 12 months at 5° C. In one embodiment, at least 97% or more of the antibodies have native conformation upon storage at −80° C., −30° C. &/or −20° C. for 6 months.

In one aspect, the present invention provides a stable liquid formulation comprising: (i) up to 100 mg/mL of an anti-PD-1 antibody; (ii) from 2 mM±0.4 mM to 20 mM±4 mM histidine buffer; (iii) up to 20%±4% (w/v) sucrose; and (iv) up to 0.2%±0.1% w/v polysorbate, at pH 6.0±0.3. In one embodiment, the stable liquid formulation comprises 25 mg/mL of anti-PD-1 antibody. In one embodiment, the stable liquid formulation comprises 50 mg/mL of anti-PD-1 antibody. In one embodiment, the stable liquid formulation comprises 75 mg/mL of anti-PD-1 antibody. In one embodiment, the stable liquid formulation comprises 10 mM±2 mM histidine buffer. In one embodiment, the stable liquid formulation comprises 5% sucrose. In one embodiment, the stable liquid formulation comprises 6% sucrose. In one embodiment, the stable liquid formulation comprises 9% sucrose. In one embodiment, the stable liquid formulation comprises 10% sucrose. In one embodiment, the stable liquid formulation comprises 0.1% polysorbate. In one embodiment, the polysorbate is polysorbate 80 or polysorbate 20. In one embodiment, the anti-PD-1 antibody comprises a HCVR/LCVR of SEQ ID NOs: 1/2.

In one aspect, a stable liquid pharmaceutical formulation of any of the preceding aspects is provided in a container. In one embodiment, the container is a polycarbonate vial. In one embodiment, the container is a glass vial. In one embodiment, the glass vial is a type 1 borosilicate glass vial with a fluorocarbon-coated butyl rubber stopper. In one embodiment, the container is a microinfuser. In one embodiment, the container is a syringe. In one embodiment, the container is a prefilled syringe. In one embodiment, the syringe comprises a fluorocarbon-coated plunger. In certain embodiments, the syringe is a 1 mL or 2.25 mL long glass syringe containing less than about 500 parts per billion of tungsten equipped with a 27-G needle, a fluorocarbon-coated butyl rubber stopper, and a latex-free, non-cytotoxic rubber tip cap. In one embodiment, the syringe is a 1 mL long glass syringe equipped with a 27-G thin wall needle, a FLUROTEC-coated 4023/50 rubber stopper, and a FM 27 rubber tip cap. In one embodiment, the syringe is a 1 mL, 2 mL, 3 mL, 5 mL or 10 mL plastic syringe fitted with a needle.

In one aspect, a kit comprising a stable pharmaceutical composition of any one of the preceding aspects, a container, and instructions is provided. In one embodiment, the container is a glass vial. In one embodiment, the container is a prefilled syringe. In one embodiment, the syringe is a 1 mL or 2.25 mL long glass syringe equipped with a 27-G thin wall needle, a FLUROTEC-coated 4023/50 rubber stopper, and a FM 27 rubber tip cap. In one embodiment, the syringe is a 1 mL, 2 mL, 3 mL, 5 mL or 10 mL plastic syringe fitted with a needle.

In certain embodiments, the present invention provides a prefilled syringe comprising a stable liquid pharmaceutical formulation comprising: (i) from 5±0.75 mg/ml to 250±37.5 mg/ml of a human antibody that specifically binds to human PD-1; (ii) from 5 mM±1 mM to 20±4 mM histidine buffer; (iii) from 0.05%±0.025% to 0.3%±0.15% (w/v) polysorbate 80; (iv) from 1%±0.2% to 10%±2% (w/v) sucrose; and (v) from 1%±0.2% to 5%±1% proline, at a pH of 6.0±0.3, wherein the antibody comprises a HCVR/LCVR comprising an amino acid sequence pair of SEQ ID NOs: 1/2; wherein the formulation has an attribute selected from the group consisting of: (i) z 98% of the antibody is in native form after storage at 5° C. for 12 months; (ii) z 53% of the antibody is the main charge variant after storage at 5° C. for 12 months; (iii) z 97% of the antibody is in native form after storage at 25° C. for 6 months; (iv) the formulation is stable to agitation stress wherein z 98% of the antibody is in native form after 120 minutes of agitation stress in the prefilled syringe; (v) over 90% of the antibodies have a molecular weight of 143 kDa±1 kDa; (vi) the pharmaceutical formulation has a viscosity of less than 20 cP, less than 15 cP, or less than 10 cP; (vii) more than 96% of the antibodies have native conformation upon storage for 12 months at 5° C.; and (viii) at least 97% or more of the antibodies have native conformation upon storage at −80° C., −30° C. &/or −20° C. for 6 months.

In certain embodiments the present invention provides a glass vial comprising a stable liquid pharmaceutical formulation comprising: (i) from 5±0.75 mg/ml to 250±37.5 mg/ml of a human antibody that specifically binds to human PD-1; (ii) from 5 mM±1 mM to 20±4 mM histidine buffer; (iii) from 0.05%±0.025% to 0.3%±0.15% (w/v) polysorbate 80; (iv) from 1%±0.2% to 10%±2% (w/v) sucrose; and (v) from 1%±0.2% to 5%±1% proline, at a pH of 6.0±0.3, wherein the antibody comprises a HCVR/LCVR comprising an amino acid sequence pair of SEQ ID NOs: 1/2; wherein the formulation has an attribute selected from the group consisting of: (i) the formulation is stable to storage and stress in a glass vial; (ii) the formulation is stable to and compatible for use in IV delivery devices; (iii) the formulation is chemically and physically stable to dilution with standard diluents known in the art (e.g., 0.9% sodium chloride or 5% dextrose); (iv) the formulation is stable to IV bags made of glass or polymer plastics (e.g., polyvinyl chloride, phthalates, polyolefins or polypropylene); (v) the formulation is compatible with standard infusion pumps (e.g., peristaltic pump, fluid displacement pump); (vi) ≥ 90% of the antibodies have a molecular weight of 143 kDa±1 kDa; (vii) the pharmaceutical formulation has a viscosity of less than 20 cP, less than 15 cP, or less than 10 cP; (viii) more than 96% of the antibodies have native conformation upon storage for 12 months at 5° C.; and (ix) at least 97% or more of the antibodies have native conformation upon storage at −80° C., −30° C. &/or −20° C. for 6 months.

Other embodiments will become apparent from a review of the ensuing detailed description.

BRIEF DESCRIPTION OF FIGURES

FIG. 1 is a table showing the effect of pH on the stability of 150 mg/mL mAb1 incubated at 45° C. for 28 days. $^a$SE-UPLC and CEX-UPLC 'Starting Material' results are the average values of the starting material for all formulations.

(FIG. 2A), −30° C. (FIG. 2B) and −20° C. (FIG. 2C) for up to 9 months and analyzed by size-exclusion chromatography (SEC).

(FIG. 3A), −30° C. (FIG. 3B) and −20° C. (FIG. 3C) for up to 6 months and analyzed by size-exclusion chromatography (SEC).

FIG. 4 is a table showing viscosity of 150 mg/mL mAb1 with the addition of excipients and viscosity modifiers.

FIG. 5 is a table that shows effect of viscosity modifiers on the stability of 175 mg/mL mAb1 incubated at 45° C. for 14 days. $^a$pH, SE-UPLC and CEX-UPLC 'Starting Material' results are the average values of the starting material for all formulations.

DETAILED DESCRIPTION

Figure 2A:
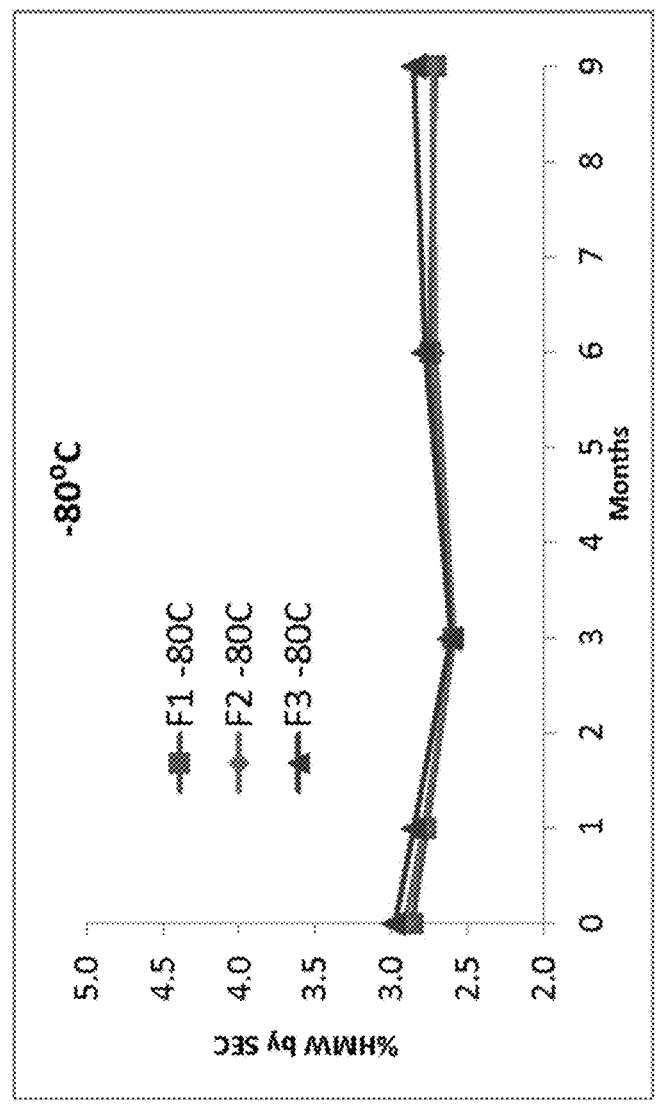
FIGS. 2A, 2B, and 2C show storage stability of three formulations F1, F2 and F3, wherein F1 comprises 210 mg/mL mAb1, 10 mM histidine and 3% proline, at pH 6.0; F2 comprises 210 mg/mL mAb1, 10 mM histidine and 3% sucrose, at pH 6.0; and F3 comprises 210 mg/mL mAb1, 10 mM histidine and 5% sucrose, at pH 6.0. Storage stability is measured by % high molecular weight species (HMW) generated upon storage at −80° C.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about", when used in reference to a particular recited numerical value or range of values, means that the value may vary from the recited value by no more than 1%. For example, as used herein, the expression "about 100" includes 99 and 101 and all values in between (e.g., 99.1, 99.2, 99.3, 99.4, etc.). Although any methods and materials similar or equivalent to those described herein can be used in the practice or testing of the present invention, preferred methods and materials are now described. All publications mentioned herein are incorporated herein by reference in their entirety.

As used herein, the expression "pharmaceutical formulation" means a combination of at least one active ingredient (e.g., a small molecule, macromolecule, compound, etc. which is capable of exerting a biological effect in a human or non-human animal), and at least one inactive ingredient which, when combined with the active ingredient or one or more additional inactive ingredients, is suitable for therapeutic administration to a human or non-human animal. The term "formulation", as used herein, means "pharmaceutical formulation" unless specifically indicated otherwise. The present invention provides pharmaceutical formulations comprising at least one therapeutic polypeptide. According to certain embodiments of the present invention, the therapeutic polypeptide is an antibody, or an antigen-binding fragment thereof, which binds specifically to human programmed death-1 (PD-1) protein. More specifically, the present invention includes pharmaceutical formulations that comprise: (i) a human antibody that specifically binds to human PD-1 (ii) a histidine buffer; (iii) an organic cosolvent that is a non-ionic surfactant; (iv) a stabilizer that is a carbohydrate; and, optionally, (v) a viscosity modifier that is an amino acid. Specific exemplary components and formulations included within the present invention are described in detail below.

Antibodies that Bind Specifically to PD-1

The pharmaceutical formulations of the present invention may comprise a human antibody, or an antigen-binding fragment thereof, that binds specifically to human PD-1. As used herein, the term "PD-1" means human programmed death-1 protein. Antibodies to human PD-1 are described in, for example, U.S. Pat. Nos. 8,008,449, and 8,168,757, 20110008369, 20130017199, 20130022595, 20150203579, and in WO2006121168, WO20091154335, WO2012145493, WO2013014668, WO2009101611, WO2015112800, EP2262837, and EP2504028.

The term "antibody", as used herein, is generally intended to refer to immunoglobulin molecules comprising four polypeptide chains, two heavy (H) chains and two light (L) chains inter-connected by disulfide bonds, as well as multimers thereof (e.g., IgM); however, immunoglobulin molecules consisting of only heavy chains (i.e., lacking light chains) are also encompassed within the definition of the term "antibody". Each heavy chain comprises a heavy chain variable region (abbreviated herein as HCVR or $V_H$) and a heavy chain constant region. The heavy chain constant region comprises three domains, CH1, CH2 and CH3. Each light chain comprises a light chain variable region (abbreviated herein as LCVR or $V_L$) and a light chain constant region. The light chain constant region comprises one domain (CL1). The $V_H$ and $V_L$ regions can be further subdivided into regions of hypervariability, termed complementary determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4.

Unless specifically indicated otherwise, the term "antibody", as used herein, shall be understood to encompass complete antibody molecules as well as antigen-binding fragments thereof. The term "antigen-binding portion" or "antigen-binding fragment" of an antibody (or simply "antibody portion" or "antibody fragment"), as used herein, refers to one or more fragments of an antibody that retain the ability to specifically bind to human PD-1 or an epitope thereof.

An "isolated antibody", as used herein, is intended to refer to an antibody that is substantially free of other antibodies having different antigenic specificities (e.g., an isolated antibody that specifically binds human PD-1 is substantially free of antibodies that specifically bind antigens other than human PD-1).

The term "specifically binds", or the like, means that an antibody or antigen-binding fragment thereof forms a complex with an antigen that is relatively stable under physiologic conditions. Specific binding can be characterized by a dissociation constant of at least about $1\times10^{-8}$M or greater. Methods for determining whether two molecules specifically bind are well known in the art and include, for example, equilibrium dialysis, surface plasmon resonance, and the like. An isolated antibody that specifically binds human PD-1 may, however, have cross-reactivity to other antigens, such as PD-1 molecules from other species (orthologs). In the context of the present invention, multispecific (e.g., bispecific) antibodies that bind to human PD-1 as well as one or more additional antigens are deemed to "specifically bind" human PD-1. Moreover, an isolated antibody may be substantially free of other cellular material or chemicals.

Exemplary anti-human PD-1 antibodies that may be included in the pharmaceutical formulations of the present invention are set forth in patent application publications US20150203579, and WO2015112800, the disclosures of which are incorporated by reference in their entirety.

According to certain embodiments of the present invention, the anti-human PD-1 antibody, or antigen-binding fragment thereof, comprises a heavy chain complementary determining region (HCDR) 1 of SEQ ID NO: 3, an HCDR2 of SEQ ID NO: 4, and an HCDR3 of SEQ ID NO: 5. In certain embodiments, the anti-human PD-1 antibody, or antigen-binding fragment thereof, comprises an HCVR of SEQ ID NO: 1.

According to certain embodiments of the present invention, the anti-human PD-1, or antigen-binding fragment thereof, comprises a light chain complementary determining region (LCDR) 1 of SEQ ID NO: 6, an LCDR2 of SEQ ID NO: 7, and an LCDR3 of SEQ ID NO: 8. In certain embodiments, the anti-human PD-1 antibody, or antigen-binding fragment thereof, comprises an LCVR of SEQ ID NO: 2.

According to certain embodiments of the present invention, the anti-human PD-1, or antigen-binding fragment thereof, comprises a HCVR having 90%, 95%, 98% or 99% sequence identity to SEQ ID NO: 1.

According to certain embodiments of the present invention, the anti-human PD-1, or antigen-binding fragment thereof, comprises a LCVR having 90%, 95%, 98% or 99% sequence identity to SEQ ID NO: 2.

According to certain embodiments of the present invention, the anti-human PD-1, or antigen-binding fragment thereof, comprises a HCVR comprising an amino acid sequence of SEQ ID NO: 1 having no more than 5 amino acid substitutions.

According to certain embodiments of the present invention, the anti-human PD-1, or antigen-binding fragment thereof, comprises a LCVR comprising an amino acid sequence of SEQ ID NO: 2 having no more than 2 amino acid substitutions.

Sequence identity may be measured by any method known in the art (e.g., GAP, BESTFIT, and BLAST).

The present invention also includes formulations comprising anti-PD-1 antibodies, wherein the anti-PD-1 antibodies comprise variants of any of the HCVR, LCVR and/or CDR amino acid sequences disclosed herein having one or more conservative amino acid substitutions. For example, the present invention includes formulations comprising anti-PD-1 antibodies having HCVR, LCVR and/or CDR amino acid sequences with, e.g., 10 or fewer, 8 or fewer, 6 or fewer, 4 or fewer, etc. conservative amino acid substitutions relative to any of the HCVR, LCVR and/or CDR amino acid sequences disclosed herein.

In certain embodiments, the anti-PD1 antibody comprises a Fc region elected from the group consisting of human IgG1, IgG2, IgG3, and IgG4 isotypes.

The non-limiting, exemplary antibody used in the Examples herein is referred to as "mAb1". This antibody is also referred to in US 20150203579 as H2M7798N or H4H7798N, and is also known as "REGN2810" or "cemiplimab". mAb1 (H4H7798N) comprises an HCVR/LCVR amino acid sequence pair having SEQ ID NOs: 1/2, and HCDR1-HCDR2-HCDR3/LCDR1-LCDR2-LCDR3 domains represented by SEQ ID NOs: 3-4-5/SEQ ID NOs: 6-7-8.

According to certain embodiments of the present invention, the anti-human PD-1, or antigen-binding fragment thereof, comprises a heavy chain of SEQ ID NO: 9 and a light chain of SEQ ID NO: 10.

It is well known in the art that terminal cleavage of amino acids can occur during production of antibodies (see, for example, Wang et al 2007, J. Pharma. Sci. 96: 1-26). Accordingly, in certain embodiments, the anti-PD-1 antibody comprises a heavy chain and a light chain, wherein the heavy chain comprises the amino acid sequence of SEQ ID NO: 11. SEQ ID NO: 11 comprises the heavy chain amino acid sequence wherein the C-terminal lysine is absent from the amino acid sequence of SEQ ID NO: 9. In certain embodiments, formulations of the present disclosure contain about 50%, about 60%, about 70%, about 80%, about 90%, about 95%, about 98% or more of the anti-PD-1 antibody wherein the C-terminal lysine is absent.

The amount of antibody, or antigen-binding fragment thereof, contained within the pharmaceutical formulations of the present invention may vary depending on the specific properties desired of the formulations, as well as the particular circumstances and purposes for which the formulations are intended to be used. In certain embodiments, the pharmaceutical formulations are liquid formulations that may contain 5±0.75 mg/mL to 250±37.5 mg/mL of antibody; 10±1.5 mg/mL to 240±36 mg/mL of antibody; 20±3.0 mg/mL to 230±34.5 mg/mL of antibody; 25±3.75 mg/mL to 240±36 mg/mL of antibody; 50±7.5 mg/mL to 230±34.5 mg/mL of antibody; 60±9 mg/mL to 240±36 mg/mL of antibody; 70±10.5 mg/mL to 230±34.5 mg/mL of antibody; 80±12 mg/mL to 220±33 mg/mL of antibody; 90±13.5 mg/mL to 210±31.5 mg/mL of antibody; 100±15 mg/mL to 200±30 mg/mL of antibody; 110±16.5 mg/mL to 190±28.5 mg/mL of antibody; 120±18 mg/mL to 180±27 mg/mL of antibody; 130±19.5 mg/mL to 170±25.5 mg/mL of antibody; 140±21 mg/mL to 160±24 mg/mL of antibody; 150±22.5 mg/mL of antibody; or 175±26.25 mg/ml. For example, the formulations of the present invention may comprise about 5 mg/mL; about 10 mg/mL; about 15 mg/mL; about 20 mg/mL; about 25 mg/mL; about 30 mg/mL; about 35 mg/mL; about 40 mg/mL; about 45 mg/mL; about 50 mg/mL; about 55 mg/mL; about 60 mg/mL; about 65 mg/mL; about 70 mg/mL; about 75 mg/mL; about 80 mg/mL; about 85 mg/mL; about 90 mg/mL; about 95 mg/mL; about 100 mg/mL; about 105 mg/mL; about 110 mg/mL; about 115 mg/mL; about 120 mg/mL; about 125 mg/mL; about 130 mg/mL; about 135 mg/mL; about 140 mg/mL; about 145 mg/mL; about 150 mg/mL; about 155 mg/mL; about 160 mg/mL; about 165 mg/mL; about 170 mg/mL; about 175 mg/mL; about 180 mg/mL; about 185 mg/mL; about 190 mg/mL; about 195 mg/mL; about 200 mg/mL; about 205 mg/mL; about 210 mg/mL; about 215 mg/mL; about 220 mg/mL; about 225 mg/mL; about 230 mg/mL; about 235 mg/mL; about 240 mg/mL; about 245 mg/mL; or about 250 mg/mL of an antibody or an antigen-binding fragment thereof, that binds specifically to human PD-1.

Excipients and pH

The pharmaceutical formulations of the present invention comprise one or more excipients. The term "excipient", as used herein, means any non-therapeutic agent added to the formulation to provide a desired consistency, viscosity or stabilizing effect.

In certain embodiments, the pharmaceutical formulation of the invention comprises at least one organic cosolvent in a type and in an amount that stabilizes the human PD-1 antibody under conditions of rough handling or agitation, such as, e.g., vortexing. In some embodiments, what is meant by "stabilizes" is the prevention of the formation of more than 3% aggregated antibody of the total amount of antibody (on a molar basis) over the course of rough handling. In some embodiments, rough handling is vortexing a solution containing the antibody and the organic cosolvent for about 60 minutes or about 120 minutes.

In certain embodiments, the organic cosolvent is a non-ionic surfactant, such as an alkyl poly(ethylene oxide). Specific non-ionic surfactants that can be included in the formulations of the present invention include, e.g., polysorbates such as polysorbate 20, polysorbate 28, polysorbate 40, polysorbate 60, polysorbate 65, polysorbate 80, polysorbate 81, and polysorbate 85; poloxamers such as poloxamer 181, poloxamer 188, poloxamer 407; or polyethylene glycol (PEG). Polysorbate 20 is also known as TWEEN 20, sorbitan monolaurate and polyoxyethylenesorbitan monolaurate. Poloxamer 188 is also known as PLURONIC F68.

The amount of non-ionic surfactant contained within the pharmaceutical formulations of the present invention may vary depending on the specific properties desired of the formulations, as well as the particular circumstances and purposes for which the formulations are intended to be used. In certain embodiments, the formulations may contain 0.01%±0.005% to 0.5%±0.25% surfactant. For example, the formulations of the present invention may comprise about 0.005%; about 0.01%; about 0.02%; about 0.03%; about 0.04%; about 0.05%; about 0.06%; about 0.07%; about 0.08%; about 0.09%; about 0.1%; about 0.11%; about 0.12%; about 0.13%; about 0.14%; about 0.15%; about 0.16%; about 0.17%; about 0.18%; about 0.19%; about 0.20%; about 0.21%; about 0.22%; about 0.23%; about 0.24%; about 0.25%; about 0.26%; about 0.27%; about 0.28%; about 0.29%; about 0.30%; about 0.35%; about 0.40%; about 0.45%; about 0.46%; about 0.47%; about 0.48%; about 0.49%; about 0.50%; about 0.55%; or about 0.575% polysorbate 20 or polysorbate 80.

The pharmaceutical formulations of the present invention may also comprise one or more stabilizers in a type and in an amount that stabilizes the human PD-1 antibody under conditions of thermal stress. In some embodiments, what is meant by "stabilizes" is maintaining greater than about 91% of the antibody in a native conformation when the solution containing the antibody and the thermal stabilizer is kept at about 45° C. for up to about 28 days. In some embodiments, what is meant by "stabilizes" is wherein less than about 6% of the antibody is aggregated when the solution containing the antibody and the thermal stabilizer is kept at about 45° C. for up to about 28 days. As used herein, "native" means the major form of the antibody by size exclusion, which is generally an intact monomer of the antibody. The term "native" also refers to non-aggregated and non-degraded form of the antibody.

In certain embodiments, the thermal stabilizer is a sugar such as sucrose, the amount of which contained within the formulation can vary depending on the specific circumstances and intended purposes for which the formulation is used. In certain embodiments, the formulations may contain about 1% to about 15% sugar; about 2% to about 14% sugar; about 3% to about 13% sugar; about 4% to about 12% sugar; about 5% to about 12% sugar; about 6% to about 11% sugar; about 7% to about 10% sugar; about 8% to about 11% sugar; or about 9% to about 11% sugar. For example, the pharmaceutical formulations of the present invention may comprise 4%±0.8%; 5%±1%; 6%±1.2%; 7%±1.4%; 8%±1.6%; 9%±1.8%; 10%±2%; 11%±2.2%; 12%±2.4%; 13%±2.6%; or about 14%±2.8% sugar (e.g., sucrose).

The pharmaceutical formulations of the present invention may also comprise a buffer or buffer system, which serves to maintain a stable pH and to help stabilize the human PD-1 antibody. The term "buffer" as used herein denotes a pharmaceutically acceptable buffer which maintains a stable pH or resists changes in pH of the solution. In preferred embodiments, the buffer comprises histidine. In the context of this disclosure, "histidine buffer" or "buffer comprising histidine" is a buffer comprising the amino acid histidine. Examples of histidine buffers include histidine chloride, histidine acetate, histidine phosphate, and histidine sulfate. In a preferred embodiment, the histidine buffer is prepared by dissolving L-histidine and L-histidine hydrochloride (e.g. as monohydrate) in a defined amount and ratio. In one embodiment, the histidine buffer is prepared by titrating L-histidine (free base, solid) with diluted hydrochloric acid. The term "histidine" is used interchangeably with "histidine buffer" throughout this disclosure. In some embodiments, what is meant by "stabilizes" is wherein less than 4.5%±0.5% of the antibody is aggregated when the solution containing the antibody and the buffer is kept at about 45° C. for up to about 28 days. In some embodiments, what is meant by "stabilizes" is wherein less than 3%±0.5% or less than 2.5%±0.5% of the antibody is aggregated when the solution containing the antibody and the buffer is kept at about 37° C. for up to about 28 days. In some embodiments, what is meant by "stabilizes" is wherein at least 93%±0.5% or at least 94%±0.5% of the antibody is in its native conformation as determined by size exclusion chromatography when the solution containing the antibody and the buffer is kept at about 45° C. for up to about 28 days. In some embodiments, what is meant by "stabilizes" is wherein at least 94%±0.5% or at least 95%±0.5% of the antibody is in its native conformation as determined by size exclusion chromatography when the solution containing the antibody and the buffer is kept at about 37° C. for up to about 28 days. By "native" or "native conformation", what is meant is the antibody fraction that is not aggregated or degraded. This is generally determined by an assay that measures the relative size of the antibody entity, such as a size exclusion chromatographic assay. The non-aggregated and non-degraded antibody elutes at a fraction that equates to the native antibody, and is generally the main elution fraction. Aggregated antibody elutes at a fraction that indicates a size greater than the native antibody. Degraded antibody elutes at a fraction that indicates a size less than the native antibody.

In some embodiments, what is meant by "stabilizes" is wherein at least 35%±0.5% of the antibody is in its main charge form as determined by cation exchange chromatography when the solution containing the antibody and the buffer is kept at about 45° C. for up to about 28 days. In some embodiments, what is meant by "stabilizes" is wherein at least 46%±0.5% or at least 39%±0.5% of the antibody is in its main charge form as determined by cation exchange chromatography when the solution containing the antibody and the buffer is kept at about 37° C. for up to about 28 days. By "main charge" or "main charge form", what is meant is the fraction of antibody that elutes from an ion exchange resin in the main peak, which is generally flanked by more "basic" peaks on one side and more "acidic" peaks on the other side.

The pharmaceutical formulations of the present invention may have a pH of from about 5.2 to about 6.4. For example, the formulations of the present invention may have a pH of about 5.5; about 5.6; about 5.7; about 5.8; about 5.9; about 6.0; about 6.1; about 6.2; about 6.3; about 6.4; or about 6.5. In some embodiments, the pH is 6.0±0.4; 6.0±0.3; 6.0±0.2; 6.0±0.1; about 6.0; or 6.0.

In some embodiments, the buffer or buffer system comprises at least one buffer that has a buffering range that overlaps fully or in part the range of pH 5.5-7.4. In certain embodiments, the buffer comprises a histidine buffer. In certain embodiments, the histidine buffer is present at a concentration of 5 mM±1 mM to 15 mM±3 mM; 6 mM±1.2 mM to 14 mM±2.8 mM; 7 mM±1.4 mM to 13 mM±2.6 mM; 8 mM±1.6 mM to 12 mM±2.4 mM; 9 mM±1.8 mM to 11 mM±2.2 mM; 10 mM±2 mM; or about 10 mM. In certain embodiments, the buffer system comprises histidine at 10 mM±2 mM, at a pH of 6.0±0.3. In preferred embodiments, the histidine buffer comprises L-histidine and L-histidine monohydrochloride monohydrate. In one embodiment, the histidine buffer comprises L-histidine at a concentration of 4.8 mM±0.96 mM. In one embodiment, the histidine buffer comprises L-histidine monohydrochloride monohydrate at a concentration of 5.2 mM±1.04 mM. In one embodiment, the histidine buffer comprises L-histidine at a concentration of 4.8 mM±0.96 mM and L-histidine monohydrochloride monohydrate at a concentration of 5.2 mM±1.04 mM.

The pharmaceutical formulations of the present invention may also comprise one or more excipients that serve to maintain a reduced viscosity or to lower the viscosity of formulations containing a high concentration of anti-PD-1 antibody drug substance (e.g., generally z 150 mg/ml of antibody). In certain embodiments, the viscosity modifier is an amino acid. In one embodiment, the amino acid is proline. In one embodiment, the pharmaceutical formulation of the present invention contains proline, preferably as L-proline, at a concentration of 1%, 1.5%, 2%, 2.5%, 3%, 3.5%, 4%, 4.5% or 5%. The term "proline" is used interchangeably with "L-proline" throughout this disclosure. In some embodiments, the formulation comprises proline in an amount sufficient to maintain the viscosity of the liquid formulation at less than 20±3 cPoise, less than 15±2.25 cPoise, or less than 11±1.65 cPoise. In some embodiments, the formulation comprises proline in an amount sufficient to maintain the viscosity at or below 15±2.25 cPoise. In certain embodiments, formulations may contain about 1% to about 5% proline; about 2% to about 4% proline; or about 3% proline. For example, the pharmaceutical formulations of the present invention may comprise 1%±0.2%; 1.5%±0.3%; 2%±0.4%; 2.5%±0.5%; 3%±0.6%; 3.5%±0.7%; 4%±0.8%; 4.5%±0.9%; or about 5%±1% proline.

During the antibody purification process it may be desired or necessary to exchange one buffer for another to achieve appropriate excipient concentrations, antibody concentration, pH, etc. Buffer exchange can be accomplished, e.g., by ultrafiltration/diafiltration (UF/DF) using, e.g., a semi-permeable tangential flow filtration membrane. Use of such techniques, however, has the potential to cause the Gibbs-Donnan effect [Bolton et al., 2011, Biotechnol. Prog. 27(1): 140-152]. The buildup of positive charge on the product side of the membrane during protein concentration is counterbalanced electrically by the preferential movement of positive ions to the opposite side of the membrane. The potential consequence of this phenomenon is that the final concentrations of certain components (e.g., histidine, L-proline, etc.) may be lower than the intended target concentrations of these components due to the electrostatic repulsion of positively charged diafiltration buffer excipients to the positively charged antibody protein during the UF/DF step. Thus, the present invention includes formulations in which the concentration of, e.g., histidine and/or L-proline vary from the recited amounts or ranges herein due to the Gibbs-Donnan effect.

Volume exclusion describes the behavior of highly concentrated samples in which a significant portion of the total volume of the solution is taken up by the solute, especially large molecules such as proteins, excluding the solvent from this space. This then decreases the total volume of solvent available for other solutes to be dissolved in, which may result in unequal partition across the ultrafiltration membrane. Thus, the present invention includes formulations in which the concentration of, e.g., histidine and/or L-proline may vary from the recited amounts or ranges herein due to the volume exclusion effect.

During the manufacture of the formulations of the present invention, variations in the composition of the formulation may occur. These variations may include the concentration of the active ingredient, the concentration of the excipients, and/or the pH of the formulation. Because changes in any of these parameters could potentially impact the stability or potency of the drug product, proven acceptable range (PAR) studies were conducted to assess whether variations in the composition, within the defined ranges, would impact the stability or potency of the antibody. Accordingly, the present invention includes formulations comprising anti-PD-1 antibodies which are stable and retain potency with up to 50% variation in the excipient concentration. For example, included herein are anti-PD-1 antibody formulations, wherein stability and potency of said formulations is unaffected by ±10%, ±20%, ±30%, ±40% or ±50% variation in the concentration of antibody, sucrose, histidine buffer and/or polysorbate.

Stability and Viscosity of the Pharmaceutical Formulations

The pharmaceutical formulations of the present invention typically exhibit high levels of stability. The term "stable", as used herein in reference to the pharmaceutical formulations, means that the antibodies within the pharmaceutical formulations retain an acceptable degree of chemical structure or biological function after storage under defined conditions. A formulation may be stable even though the antibody contained therein does not maintain 100% of its chemical structure or biological function after storage for a defined amount of time. Under certain circumstances, maintenance of about 90%, about 95%, about 96%, about 97%, about 98% or about 99% of an antibody's structure or function after storage for a defined amount of time may be regarded as "stable".

Stability can be measured, inter alia, by determining the percentage of native antibody that remains in the formulation after storage for a defined amount of time at a defined temperature. The percentage of native antibody can be determined by, inter alia, size exclusion chromatography (e.g., size exclusion ultra performance liquid chromatography [SE-UPLC]), such that native means non-aggregated and non-degraded. An "acceptable degree of stability", as that phrase is used herein, means that at least 90% of the native form of the antibody can be detected in the formulation after storage for a defined amount of time at a given temperature. In certain embodiments, at least about 90%, 91%, 92%, 93%, 94%, 95%, 96%, 97%, 98%, 99% or 100% of the native form of the antibody can be detected in the formulation after storage for a defined amount of time at a defined temperature. The defined amount of time after which stability is measured can be at least 14 days, at least 28 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, or more. The defined temperature at which the pharmaceutical formulation may be stored when assessing stability can be any temperature from about −80° C. to about 45° C., e.g., storage at about −80° C., about −30° C., about −20° C., about 0° C., about 4°-8° C., about 5° C., about 25° C., about 35° C., about 37° C., or about 45° C. For example, a pharmaceutical formulation may be deemed stable if after 6 months of storage at 5° C., greater than about 95%, 96%, 97% or 98% of native antibody is detected by SE-UPLC. A pharmaceutical formulation may also be deemed stable if after 6 months of storage at 25° C., greater than about 95%, 96%, 97% or 98% of native antibody is detected by SE-UPLC. A pharmaceutical formulation may also be deemed stable if after 28 days of storage at 45° C., greater than about 89%, 90%, 91%, 92%, 93%, 94%, 95% or 96% of native antibody is detected by SE-UPLC. A pharmaceutical formulation may also be deemed stable if after 12 months of storage at −20° C., greater than about 96%, 97%, or 98% of native antibody is detected by SE-UPLC. A pharmaceutical formulation may also be deemed stable if after 12 months of storage at −30° C., greater than about 96%, 97% or 98% of native antibody is detected by SE-UPLC. A pharmaceutical formulation may also be deemed stable if after 12 months of storage at −80° C., greater than about 96%, 97% or 98% of native antibody is detected by SE-UPLC.

Stability can be measured, inter alia, by determining the percentage of antibody that forms in an aggregate within the formulation after storage for a defined amount of time at a defined temperature, wherein stability is inversely proportional to the percent aggregate that is formed. The percentage of aggregated antibody can be determined by, inter alia, size exclusion chromatography (e.g., size exclusion ultra performance liquid chromatography [SE-UPLC]). An "acceptable degree of stability", as that phrase is used herein, means that at most 5% of the antibody is in an aggregated form (also denoted as the high molecular weight—HMW—form) detected in the formulation after storage for a defined amount of time at a given temperature. In certain embodiments an acceptable degree of stability means that at most about 5%, 4%, 3%, 2%, 1%, 0.5%, or 0.1% of the antibody can be detected in an aggregate in the formulation after storage for a defined amount of time at a given temperature. The defined amount of time after which stability is measured can be at least 2 weeks, at least 28 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, or more. The temperature at which the pharmaceutical formulation may be stored when assessing stability can be any temperature from about −80° C. to about 45° C., e.g., storage at about −80° C., about −30° C., about −20° C., about 0° C., about 4°-8° C., about 5° C., about 25° C., about 35° C., about 37° C. or about 45° C. For example, a pharmaceutical formulation may be deemed stable if after 12 months of storage at 5° C., less than about 2%, 1%, 0.5%, or 0.1% of the antibody is detected in an aggregated form. A pharmaceutical formulation may also be deemed stable if after three months of storage at 25° C., less than about 4%, 3%, 2%, 1%, 0.5%, or 0.1% of the antibody is detected in an aggregated form. A pharmaceutical formulation may also be deemed stable if after 28 days of storage at 45° C., less than about 10%, 9%, 8%, 7%, 6%, 5%, 4%, 3%, 2%, 1%, or 0.5%, of the antibody is detected in an aggregated form. A pharmaceutical formulation may also be deemed stable if after three months of storage at −20° C., −30° C., or −80° C. less than about 3%, 2%, 1%, 0.5%, or 0.1% of the antibody is detected in an aggregated form.

Stability can be measured, inter alia, by determining the percentage of antibody that migrates in a more acidic fraction during ion exchange ("acidic form") than in the main fraction of antibody ("main charge form"), wherein stability is inversely proportional to the fraction of antibody in the acidic form. While not wishing to be bound by theory, deamidation of the antibody may cause the antibody to become more negatively charged and thus more acidic relative to the non-deamidated antibody (see, e.g., Robinson, N., Protein Deamidation, PNAS, Apr. 16, 2002, 99(8):5283-5288). The percentage of "acidified" antibody can be determined by, inter alia, ion exchange chromatography (e.g., cation exchange ultra performance liquid chromatography [CEX-UPLC]). An "acceptable degree of stability", as that phrase is used herein, means that at most 45% of the antibody is in a more acidic form detected in the formulation after storage for a defined amount of time at a defined temperature. In certain embodiments an acceptable degree of stability means that at most about 40%, 35%, 30%, 25%, 20%, 15%, 10%, 5%, 4%, 3%, 2%, 1%, 0.5%, or 0.1% of the antibody can be detected in an acidic form in the formulation after storage for a defined amount of time at a given temperature. In one embodiment, an acceptable degree of stability means that less than 30%, 25%, 20%, 15%, 10%, 5%, 4%, 3%, 2%, 1%, 0.5%, or 0.1% of the antibody can be detected in an acidic form in the formulation after storage for a defined amount of time at a given temperature. The defined amount of time after which stability is measured can be at least 2 weeks, at least 28 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, or more. The temperature at which the pharmaceutical formulation may be stored when assessing stability can be any temperature from about −80° C. to about 45° C., e.g., storage at about −80° C., about −30° C., about −20° C., about 0° C., about 4°–8° C., about 5° C., about 25° C., or about 45° C. For example, a pharmaceutical formulation may be deemed stable if after three months of storage at −80° C., −30° C., or −20° C. less than about 30%, 29%, 28%, 27%, 26%, 25%, 24%, 23%, 22%, 21%, 20%, 19%, 18%, 17%, 16%, 15%, 14%, 13%, 12%, 10%, 9%, 8%, 7%, 6%, 5%, 4%, 3%, 2%, 1%, 0.5% or 0.1% of the antibody is in a more acidic form. A pharmaceutical formulation may also be deemed stable if after six months of storage at 5° C., less than about 32%, 31%, 30%, 29%, 28%, 27%, 26%, 25%, 24%, 23%, 22%, 21%, 20%, 19%, 18%, 17%, 16%, 15%, 14%, 13%, 12%, 10%, 9%, 8%, 7%, 6%, 5%, 4%, 3%, 2%, 1%, 0.5% or 0.1% of the antibody is in a more acidic form. A pharmaceutical formulation may also be deemed stable if after six months of storage at 25° C., less than about 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 10%, 9%, 8%, 7%, 6%, 5%, 4%, 3%, 2%, 1%, 0.5% or 0.1% of the antibody is in a more acidic form. A pharmaceutical formulation may also be deemed stable if after 28 days of storage at 45° C., less than about 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 10%, 9%, 8%, 7%, 6%, 5%, 4%, 3%, 2%, 1%, 0.5% or 0.1% of the antibody can be detected in a more acidic form.

Other methods may be used to assess the stability of the formulations of the present invention such as, e.g., differential scanning calorimetry (DSC) to determine thermal stability, controlled agitation to determine mechanical stability, and absorbance at about 350 nm or about 405 nm to determine solution turbidities. For example, a formulation of the present invention may be considered stable if, after 6 or more months of storage at about 5° C. to about 25° C., the change in $OD_{405}$ of the formulation is less than about 0.05 (e.g., 0.04, 0.03, 0.02, 0.01, or less) from the $OD_{405}$ of the formulation at time zero.

Measuring the biological activity or binding affinity of the antibody to its target may also be used to assess stability. For example, a formulation of the present invention may be regarded as stable if, after storage at e.g., 5° C., 25° C., 45° C., etc. for a defined amount of time (e.g., 1 to 12 months), the anti-PD-1 antibody contained within the formulation binds to PD-1 with an affinity that is at least 90%, 95%, or more of the binding affinity of the antibody prior to said storage. Binding affinity may be determined by e.g., ELISA or surface plasmon resonance. Biological activity may be determined by a PD-1 activity assay, such as e.g., contacting a cell that expresses PD-1 with the formulation comprising the anti PD-1 antibody. The binding of the antibody to such a cell may be measured directly, such as e.g., via FACS analysis. Alternatively, the downstream activity of the PD-1 system may be measured in the presence of the antibody, and compared to the activity of the PD-1 system in the absence of antibody. In some embodiments, the PD-1 may be endogenous to the cell. In other embodiments, the PD-1 may be ectopically expressed in the cell.

Additional methods for assessing the stability of an antibody in formulation are demonstrated in the Examples presented below.

The liquid pharmaceutical formulations of the present invention may, in certain embodiments, exhibit low to moderate levels of viscosity. "Viscosity" as used herein may be "kinematic viscosity" or "absolute viscosity". "Kinematic viscosity" is a measure of the resistive flow of a fluid under the influence of gravity. When two fluids of equal volume are placed in identical capillary viscometers and allowed to flow by gravity, a viscous fluid takes longer than a less viscous fluid to flow through the capillary. For example, if one fluid takes 200 seconds to complete its flow and another fluid takes 400 seconds, the second fluid is twice as viscous as the first on a kinematic viscosity scale. "Absolute viscosity", sometimes called dynamic or simple viscosity, is the product of kinematic viscosity and fluid density (Absolute Viscosity=Kinematic Viscosity×Density). The dimension of kinematic viscosity is $L^2/T$ where L is a length and T is a time. Commonly, kinematic viscosity is expressed in centistokes (cSt). The SI unit of kinematic viscosity is $mm^2/s$, which is 1 cSt. Absolute viscosity is expressed in units of centipoise (cP). The SI unit of absolute viscosity is the milliPascal-second (mPa-s), where 1 cP=1 mPa-s.

As used herein, a low level of viscosity, in reference to a fluid formulation of the present invention, will exhibit an absolute viscosity of less than about 20 cPoise (cP). For example, a fluid formulation of the invention will be deemed to have "low viscosity", if, when measured using standard viscosity measurement techniques, the formulation exhibits an absolute viscosity of about 20 cP, about 19 cP, about 18 cP, about 15 cP, about 12 cP, about 10 cP, about 9 cP, about 8 cP, or less. As used herein, a moderate level of viscosity, in reference to a fluid formulation of the present invention, will exhibit an absolute viscosity of between about 35 cP and about 20 cP. For example, a fluid formulation of the invention will be deemed to have "moderate viscosity", if when measured using standard viscosity measurement techniques, the formulation exhibits an absolute viscosity of about 34 cP, about 33 cP, about 32 cP, about 31 cP, about 30 cP, about 29 cP, about 28 cP, about 27 cP, about 26 cP, about 25 cP, about 24 cP, about 23 cP, about 22 cP, about 21 cP, about 20 cP, about 19 cP, 18 cP, about 17 cP, about 16 cP, or about 15.1 cP.

As illustrated in the examples below, the present inventors have made the surprising discovery that low viscosity liquid formulations comprising high concentrations of an anti-human PD-1 antibody (e.g., from about 50 mg/ml up to 250 mg/mL) can be obtained by formulating the antibody with proline from about 1% to about 5% and sucrose at about 5%. Such formulations are stable to stress during handling and to storage at temperatures ranging from 45° C. to −80° C. (shown herein) and have low viscosity (have viscosity ranging from 7 to 15 cP).

Exemplary Formulations

According to one aspect of the present invention, the pharmaceutical formulation is a stable, low viscosity, generally physiologically isotonic liquid formulation, which comprises: (i) a human antibody that specifically binds to human PD-1 (e.g., H4H7798N), at a concentration of up to 250 mg/mL±45 mg/mL; (ii) a histidine buffer system that provides sufficient buffering at about pH 6.0±0.3; (iii) an organic cosolvent, which protects the structural integrity of the antibody; (iv) a thermal stabilizer that is a sugar; and (iv) a viscosity modifier that is an amino acid, which serves to keep the viscosity manageable for injection in a convenient volume for subcutaneous administration.

According to one embodiment, the stable, low-viscosity pharmaceutical formulation comprises: (i) a human IgG4 antibody that specifically binds to human PD-1, and which comprises an HCDR1 of SEQ ID NO: 3, an HCDR2 of SEQ ID NO: 4, an HCDR3 of SEQ ID NO: 5, an LCDR1 of SEQ ID NO: 6, an LCDR2 of SEQ ID NO: 7, and an LCDR3 of SEQ ID NO: 8, at a concentration of up to 200 mg/ml±30 mg/mL; (ii) histidine buffer at 10 mM±2 mM, which buffers at pH 6.0±0.3; (iii) polysorbate 80 at 0.2% w/v±0.1% w/v; (iv) sucrose at 5%±1% w/v; and (v) L-proline at 1.5% (w/v)±0.3%.

According to one embodiment, the stable low-viscosity pharmaceutical formulation comprises: (i) a human IgG4 antibody that specifically binds to human PD-1, and which comprises an HCDR1 of SEQ ID NO: 3, an HCDR2 of SEQ ID NO: 4, an HCDR3 of SEQ ID NO: 5, an LCDR1 of SEQ ID NO: 6, an LCDR2 of SEQ ID NO: 7, and an LCDR3 of SEQ ID NO: 8, at a concentration of 175 mg/ml±26.25 mg/mL; (ii) histidine buffer at 10 mM±2 mM, which buffers at pH 6.0±0.3; (iii) polysorbate 80 at 0.2% w/v±0.1% w/v; (iv) sucrose at 5%±1% w/v; and (v) L-proline at 1.5% (w/v)±0.3%.

According to one embodiment, the stable low-viscosity pharmaceutical formulation comprises: (i) a human IgG4 antibody that specifically binds to human PD-1, and which comprises an HCDR1 of SEQ ID NO: 3, an HCDR2 of SEQ ID NO: 4, an HCDR3 of SEQ ID NO: 5, an LCDR1 of SEQ ID NO: 6, an LCDR2 of SEQ ID NO: 7, and an LCDR3 of SEQ ID NO: 8, at a concentration of 150 mg/ml±22.5 mg/mL; (ii) histidine buffer at 10 mM±2 mM, which buffers at pH 6.0±0.3; (iii) polysorbate 80 at 0.2% w/v±0.1% w/v; (iv) sucrose at 5%±1% w/v; and (v) L-proline at 1.5% (w/v)±0.3%.

According to one embodiment, the stable low-viscosity pharmaceutical formulation comprises: (i) a human IgG4 antibody that specifically binds to human PD-1, and which comprises an HCDR1 of SEQ ID NO: 3, an HCDR2 of SEQ ID NO: 4, an HCDR3 of SEQ ID NO: 5, an LCDR1 of SEQ ID NO: 6, an LCDR2 of SEQ ID NO: 7, and an LCDR3 of SEQ ID NO: 8, at a concentration of 100 mg/mL±15 mg/mL; (ii) histidine buffer at 10 mM±2 mM, which buffers at pH 6.0±0.3; (iii) sucrose at 5% w/v±1% w/v; (iv) polysorbate 80 at 0.2% w/v±0.1%; and L-proline at 1.5% (w/v) ±0.3%.

According to one embodiment, the stable low-viscosity pharmaceutical formulation comprises: (i) a human IgG4 antibody that specifically binds to human PD-1, and which comprises an HCDR1 of SEQ ID NO: 3, an HCDR2 of SEQ ID NO: 4, an HCDR3 of SEQ ID NO: 5, an LCDR1 of SEQ ID NO: 6, an LCDR2 of SEQ ID NO: 7, and an LCDR3 of SEQ ID NO: 8, at a concentration of 50 mg/mL±7.5 mg/mL; (ii) histidine buffer at 10 mM±2 mM, which buffers at pH 6.0±0.3; (iii) sucrose at 5% w/v±1% w/v; (iv) polysorbate 80 at 0.2% w/v±0.1%; and L-proline at 1.5% (w/v)±0.3%.

According to one embodiment, the stable low-viscosity pharmaceutical formulation comprises: (i) a human IgG4 antibody that specifically binds to human PD-1, and which comprises an HCDR1 of SEQ ID NO: 3, an HCDR2 of SEQ ID NO: 4, an HCDR3 of SEQ ID NO: 5, an LCDR1 of SEQ ID NO: 6, an LCDR2 of SEQ ID NO: 7, and an LCDR3 of SEQ ID NO: 8, at a concentration of 25 mg/mL±3.75 mg/mL; (ii) histidine buffer at 10 mM±2 mM, which buffers at pH 6.0±0.3; (iii) sucrose at 5% w/v±1% w/v; (iv) polysorbate 80 at 0.2% w/v±0.1%; and L-proline at 1.5% (w/v) ±0.3%.

Additional non-limiting examples of pharmaceutical formulations encompassed by the present invention are set forth elsewhere herein, including the working Examples presented below.

Containers and Methods of Administration

The pharmaceutical formulations of the present invention may be contained within any container suitable for storage of medicines and other therapeutic compositions. For example, the pharmaceutical formulations may be contained within a sealed and sterilized plastic or glass container having a defined volume such as a vial, ampule, syringe, cartridge, or bottle. Different types of vials can be used to contain the formulations of the present invention including, e.g., clear and opaque (e.g., amber) glass or plastic vials. Likewise, any type of syringe can be used to contain or administer the pharmaceutical formulations of the present invention.

The pharmaceutical formulations of the present invention may be contained within "normal tungsten" syringes or "low tungsten" syringes. As will be appreciated by persons of ordinary skill in the art, the process of making glass syringes generally involves the use of a hot tungsten rod which functions to pierce the glass thereby creating a hole from which liquids can be drawn and expelled from the syringe. This process results in the deposition of trace amounts of tungsten on the interior surface of the syringe. Subsequent washing and other processing steps can be used to reduce the amount of tungsten in the syringe. As used herein, the term "normal tungsten" means that the syringe contains greater than or equal to 500 parts per billion (ppb) of tungsten. The term "low tungsten" means that the syringe contains less than 500 ppb of tungsten. For example, a low tungsten syringe, according to the present invention, can contain less than about 490, 480, 470, 460, 450, 440, 430, 420, 410, 390, 350, 300, 250, 200, 150, 100, 90, 80, 70, 60, 50, 40, 30, 20, 10 or fewer ppb of tungsten.

The rubber plungers used in syringes, and the rubber stoppers used to close the openings of vials, may be coated to prevent contamination of the medicinal contents of the syringe or vial, or to preserve their stability. Thus, pharmaceutical formulations of the present invention, according to certain embodiments, may be contained within a syringe that comprises a coated plunger, or within a vial that is sealed with a coated rubber stopper. For example, the plunger or stopper may be coated with a fluorocarbon film. Examples of coated stoppers or plungers suitable for use with vials and syringes containing the pharmaceutical formulations of the present invention are mentioned in, e.g., U.S. Pat. Nos. 4,997,423; 5,908,686; 6,286,699; 6,645,635; and 7,226,554, the contents of which are incorporated by reference herein in their entireties. Particular exemplary coated rubber stoppers and plungers that can be used in the context of the present invention are commercially available under the tradename "FluroTec®", available from West Pharmaceutical Services, Inc. (Lionville, Pa.). FluroTec® is an example of a fluorocarbon coating used to minimize or prevent drug product from adhering to the rubber surfaces.

According to certain embodiments of the present invention, the pharmaceutical formulations may be contained within a low tungsten syringe that comprises a fluorocarbon-coated plunger.

The pharmaceutical formulations can be administered to a patient by parenteral routes such as injection (e.g., subcutaneous, intravenous, intramuscular, intraperitoneal, etc.) or percutaneous, mucosal, nasal, pulmonary or oral administration. Numerous reusable pen or autoinjector delivery devices can be used to subcutaneously deliver the pharmaceutical formulations of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany). Examples of disposable pen or autoinjector delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUMIRA™ Pen (Abbott Labs, Abbott Park, Ill.).

The use of a microinfusor to deliver the pharmaceutical formulations of the present invention is also contemplated herein. As used herein, the term "microinfusor" means a subcutaneous delivery device designed to slowly administer large volumes (e.g., up to about 2.5 mL or more) of a therapeutic formulation over a prolonged period of time (e.g., about 10, 15, 20, 25, 30 or more minutes). See, e.g., U.S. Pat. Nos. 6,629,949; 6,659,982; and Meehan et al., *J. Controlled Release* 46:107-116 (1996). Microinfusors are particularly useful for the delivery of large doses of therapeutic proteins contained within high concentration (e.g., about 100, 125, 150, 175, 200 or more mg/mL) or viscous solutions.

In certain embodiments, the stable liquid pharmaceutical formulation of any of the preceding aspects is contained in a sterile glass vial and is administered as an IV infusion.

In one embodiment, the container is a 20 mL type 1 clear borosilicate glass vial. In certain embodiments, the container is a 2 mL, 5 mL or 10 mL type 1 borosilicate glass vial with a chlorobutyl stopper, with a FluroTec® coating.

In one embodiment, the liquid pharmaceutical formulation of the present invention comprising about 25 mg/mL or 50 mg/mL of mAb1 is administered intravenously and may be contained in a glass vial.

In certain embodiments, the present invention provides an autoinjector comprising any of the liquid formulations described herein. In some embodiments, the present invention provides an autoinjector comprising a stable liquid formulation comprising about 50 mg/mL, about 100 mg/mL, about 150 mg/mL or about 175 mg/mL of mAb1, about 10 mM of histidine, at pH of about 6.0, about 5% sucrose, about 1.5% proline and about 0.2% polysorbate 80.

In certain embodiments, the present invention provides a prefilled syringe comprising any of the liquid formulations described herein. In some embodiments, the present invention provides a prefilled syringe comprising a stable liquid formulation comprising about 50 mg/mL, about 100 mg/mL, about 150 mg/mL or about 175 mg/mL of mAb1, about 10 mM of histidine, at pH of about 6.0, about 5% sucrose, about 1.5% proline and about 0.2% polysorbate 80. In certain embodiments, the syringe is a 1 mL or 2.25 mL long glass syringe filled with a 27-gauge thin wall needle, a fluorocarbon coated rubber plunger and a rubber needle shield.

In one embodiment, the liquid pharmaceutical formulation containing about 175 mg/mL±26.25 mg/mL mAb1 is administered in a volume of approximately up to 2 mL in a prefilled syringe. In certain embodiments, the syringe is a 1 mL or 2.25 mL long glass syringe filled with a 27-gauge thin wall needle, a fluorocarbon coated rubber plunger and a rubber needle shield. In one embodiment, the syringe is an OMPI 1 mL long glass syringe fitted with a 27-gauge needle, a FM27 rubber needle shield, and a FLUROTEC® coated 4023/50 rubber plunger.

In one embodiment, the liquid pharmaceutical formulation containing about 150 mg/mL±22.5 mg/mL anti-PD-1 antibody is administered in a volume of approximately up to 2 mL in a prefilled syringe. In one embodiment, the syringe is a 1 mL or 2.25 mL long glass syringe filled with a 27-gauge thin wall needle, a fluorocarbon coated rubber plunger and a rubber needle shield. In one embodiment, the syringe is an OMPI 1 mL long glass syringe fitted with a 27-gauge needle, a FM27 rubber needle shield, and a FLUROTEC® coated 4023/50 rubber plunger.

Therapeutic Uses of the Pharmaceutical Formulations

The pharmaceutical formulations of the present invention are useful, inter alia, for the treatment, prevention or amelioration of any disease or disorder associated with PD-1 activity, including diseases or disorders mediated by PD-1. Exemplary, non-limiting diseases and disorders that can be treated or prevented by the administration of the pharmaceutical formulations of the present invention include viral infections, autoimmune diseases and various cancers such as, e.g., brain cancer, lung cancer, prostate cancer, colorectal cancer, head and neck cancer, skin cancer, various blood cancers, and endometrial cancers.

EXAMPLES

The following examples are presented so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by mole, molecular weight is average molecular weight, temperature is in degrees Centigrade, and pressure is at or near atmospheric pressure.

Example 1: Development of an Anti-PD-1 Antibody Formulation

The goals of the formulation activities were to develop a formulation with the following attributes:
  A liquid formulation with a concentration of the anti-PD-1 antibody sufficient to deliver a dose of 250 mg or more by intravenous infusion;
  A near iso-osmolar formulation that is stable upon dilution with commonly used diluents, e.g., 0.9% sodium chloride injection or 5% dextrose injection, for intravenous infusion;
  A formulation that is compatible with and stable in Type 1 clear glass vial and standard serum stopper as packaging; and
  A sterile drug product (DP) solution that supports long-term stability;
    A formulation that minimizes antibody high molecular weight (HMW) species when subjected to handling and thermal stresses;
    A formulation that minimizes changes in the relative distribution of antibody charged species when subjected to thermal stress; and
    A formulation that maintains biological activity when subjected to handling and thermal stress.

Throughout formulation development, three primary protein stress conditions (representing extreme handling conditions beyond which the antibody drug product would not be subjected during handling, manufacturing, shipping, storing, and labeling) were employed to develop and optimize the antibody formulations and to evaluate the effects of potential real-world stresses on the stability of the drug product. These stress conditions included:

Agitation (vortexing) of the protein solution at room temperature. Vortexing in glass vials exceeds the agitation that occurs during the handling and manufacturing of the protein.

Incubating the protein solution at elevated temperature (37° C., 40° C. or 45° C.) relative to the proposed DP storage condition (2° C.–8° C.).

Subjecting the protein to multiple freeze thaw cycles. Since the protein will undergo at least one freeze thaw cycle during the manufacture of DP, multiple freeze thaw cycles simulate and exceed the actual stress the protein is expected to experience.

There were four main goals of the initial formulation development work:

1. Selection of buffer and pH: The choice of buffer and pH can have a large effect on the stability of proteins, hence deciding on the optimal buffer species and pH is an important process. Studies are presented in these sections that demonstrate the rationale for choice of the optimal buffer and pH for antibody.
2. Selection of surfactant or organic cosolvent: A surfactant or organic cosolvent, such as polysorbate, is typically required to prevent precipitation or aggregation of proteins when agitated. Soluble protein may be subjected to agitation when handled, filtered, mixed, manufactured, shipped, and administered. The antibody drug substance in a simple buffered solution can become visibly cloudy with excess agitation. Therefore, it was determined that stabilizing the protein to handling and agitation was important.
3. Identification/selection of stabilizing/tonicifying excipients: The addition of sugars, salts, and amino acids were examined for their ability to improve the stability of antibody to thermal stress and to increase the shelf life of the DP. The rationale for inclusion of these thermal stabilizers, as well as studies identifying the optimal concentrations in the final formulation are presented herein.
4. Selection of antibody concentration: The effect of antibody concentration on the stability of the drug product with the selected excipients was examined.

Initial formulation development activities were conducted using 5-50 mg/mL of the anti-PD-1 antibody and involved screening organic cosolvents, thermal stabilizers, and buffers in liquid formulations of anti-PD-1 antibodies to identify excipients that are compatible with the protein and enhance its stability, while maintaining near physiologic osmolality and low viscosity for intravenous and subcutaneous injection. Buffer conditions were also examined to determine the optimal pH for maximum protein stability (described in Examples 4, 6 and 7 herein).

Results from this initial formulation development work were used to develop an initial formulation that was suitable for Phase 1 clinical studies. The phase 1 formulation also provided a reference to optimize late phase clinical and commercial formulations.

With the knowledge gained from the initial formulation development, the late stage formulation development activities involved optimizing pH, surfactant concentration, and stabilizers to identify excipients that enhance protein stability at both low and high protein concentrations (up to 175 mg/mL mAb1) (described in Examples 5, 8, 9, and 10).

Throughout formulation development, the formulations were assessed for stress and storage stability. The methods used to assess stability in the formulation development studies are described in Example 3 herein. Examples 11 and 12 describe the storage and stress stability of the formulations.

Example 13 describes the stability of formulations when the excipients were varied within specific ranges.

Results generated from these studies were used to develop stable liquid formulations suitable for clinical use, for either intravenous (IV) or subcutaneous administration (SC). Example 14 describes containers used for the formulations herein. Examples 15, 16 and 17 describe the compatibility and stability of the formulations in glass vials, prefilled syringes and intravenous delivery devices. Such formulations met the objectives defined for formulation development:

The developed formulations are suitable for the developed doses;

A tonicity that is iso-osmolar to physiologic conditions; The osmolality of the 50 mg/mL formulation is approximately 318 mOsm/kg;

Sterile DP solution that supports long-term stability in liquid state;

Minimal formation of antibody HMW species occurs upon long-term storage at 2-8° C.;

Little to no change in the relative distribution of antibody charged species occurs upon long-term storage at 2-8° C.; and Minimal formation of subvisible particles was observed in antibody DP under accelerated storage and stress conditions, and upon storage at 5° C. for 12 months.

Other attributes of the formulations will be apparent from the description herein.

Anti-PD-1 Antibodies:

Anti-PD-1 antibodies are described in US20150203579, incorporated herein in its entirety. The exemplary antibody used in the Examples below is a fully human anti-PD-1 antibody H4H7798N (as disclosed in US20150203579, known as "REGN2810" or "cemiplimab") comprising a heavy chain comprising the amino acid sequence of SEQ ID NO: 9 and a light chain comprising the amino acid sequence of SEQ ID NO: 10; an HCVR/LCVR amino acid sequence pair comprising SEQ ID NOs: 1/2; and heavy and light chain CDR sequences comprising SEQ ID NOs: 3-8; and herein referred to as "mAb1".

Example 2: Exemplary Formulations

In certain embodiments, mAb1 is formulated as an aqueous buffered formulation containing from 5 mg/ml±0.75 mg/ml to 250 mg/ml±45.0 mg/ml mAb1, 10 mM±2 mM histidine buffer, 0.2%±0.1% w/v polysorbate, 1%±0.2% to 10%±2% w/v sucrose, and 1%±0.02% to 5%±1% w/v proline, at pH 6.0±0.3.

Exemplary formulations include:

A stable low-viscosity pharmaceutical formulation comprising: 25 mg/ml±3.75 mg/mL mAb1, 10±2 mM histidine buffer, 0.2%±0.1% w/v polysorbate 80, 5%±1% w/v sucrose, and 1.5%±0.3% w/v L-proline, at pH 6.0±0.3.

A stable low-viscosity pharmaceutical formulation comprising: 50 mg/ml±7.5 mg/mL mAb1, 10±2 mM histidine buffer, 0.2%±0.1% w/v polysorbate 80, 5%±1% w/v sucrose, and 1.5%±0.3% w/v L-proline, at pH 6.0±0.3.

A stable low-viscosity pharmaceutical formulation comprising: 150±23 mg/mL mAb1, 10±2 mM histidine buffer, 0.2%±0.1% w/v polysorbate 80, 5%±1% w/v sucrose, and 1.5%±0.3% w/v L-proline, at pH 6.0±0.3.

A stable low-viscosity pharmaceutical formulation comprising: 175±27 mg/mL mAb1, 10±2 mM histidine buffer, 0.2%±0.1% w/v polysorbate 80, 5%±1% w/v sucrose, and 1.5%±0.3% w/v L-proline, at pH 6.0±0.3.

Example 3: Methods Used to Assess Formulation Stability

The following assays were applied to assess formulation stability:

Color and appearance by visual inspection
pH
Turbidity measured by increase in OD at 405 nm, or by nephelometry
Particulate matter analysis performed by microflow imaging (MFI) (reported as particle counts obtained as is), and light obscuration (HIAC)
Protein concentration by reverse phase-ultra performance liquid chromatography (RP-UPLC)
Purity by size exclusion-ultra performance liquid chromatography (SE-UPLC), or by reduced and non-reduced microchip capillary electrophoresis sodium dodecyl sulfate (MCE-SDS) PAGE
Charge variant analysis by cation exchange chromatography-ultra performance liquid chromatography (CEX-UPLC), or by imaged capillary isoelectric focusing (iCIEF)
Potency by bioassay: The relative potency of each sample is determined using a bioassay and is defined as: ($IC_{50}$ reference sample/$IC_{50}$ sample)*100%. The measured potency of storage stability samples must be within 50% to 150% of the measured potency of the reference standard.

The physical stability of a formulation refers to properties such as color, appearance, pH, turbidity, and protein concentration. The presence of visible particulates in solution can be detected by visual inspection. A solution passes visual inspection if it is clear to slightly opalescent, essentially free from visible particulates, and colorless to pale yellow. In addition, turbidity, measured by OD at 405 nm, can also be used to detect particulates in solution. An increase in OD at 405 nm may indicate the presence of particulates, an increase in opalescence, or color change of the test articles. MFI is used to measure subvisible particulates that are ≥2 μm in size. The protein concentration of mAb1 is measured by a RP-UPLC assay and reported as percent protein recovery relative to the starting material. In the RP-UPLC assay, mAb1 is eluted from the RP column as a single peak. The protein concentration is determined from the mAb1 total peak area by comparing it with a calibration curve generated using mAb1 standards. Percent of recovery is calculated based on the measured protein concentration relative to the starting protein concentration.

Chemical stability refers to the formation of covalently modified forms (e.g. covalent aggregates, cleavage products, or charge variant forms) and non-covalently modified forms (e.g. non-covalent aggregates) of protein. Higher and lower molecular weight degradation products can be separated from native mAb1 by SE-UPLC and MCE-SDS methods. The percentage of degraded mAb1 in the SE-UPLC and MCE-SDS methods is calculated from the ratio of the area of all non-native peaks to the total area of all mAb1 peaks. Charge variant forms of mAb1 are resolved using CEX-UPLC and iCIEF. In the CEX-UPLC method, peaks with retention times earlier than that of the main peak are labeled as "acidic" peaks; the peaks with retention times later than that of the main peak are labeled as "basic" peaks. In the iCIEF method, peaks that are focused to a pI lower than that of the main peak are labeled "acidic" peaks, whereas those focused to a pI higher than that of the main peak are labeled "basic" peaks.

Example 4: Effect of Different Buffers and pH

The effect of buffer and pH on the thermal stability of mAb1 was examined in liquid formulations by incubating 5 mg/mL mAb1 at 45° C. for 28 days in a series of buffer systems at varying pH ranges. The following pH and buffer systems were studied: acetate (pH 4.5, 5.0, 5.5), histidine (pH 5.5, 6.0, 6.5), and phosphate (pH 6.0, 6.5, 7.0). Based on results from SE-UPLC analysis, maximum protein stability was observed when mAb1 was formulated between pH 6.0 and 6.5 in histidine buffer (Table 1).

TABLE 1

Effect of Buffer and pH on the Stability of 5 mg/mL mAb1 Incubated at 45° C. for 28 Days

| Formulation | 5 mg/mL mAb1, 10 mM Buffer |
| Fill Volume | 0.4 mL |
| Container | 2 mL Type 1 borosilicate glass vial with a FluroTec ® coated 4432/50 butyl rubber stopper |

| pH/Buffer | Color and Appearance | Turbidity (Increase in OD at 405 nm) | % Protein Recoverd by RP-UPLC | Change in Purity by SE-UPLC[a] | | | Change in Charge Variants by CEX-UPLC[a] | | |
|---|---|---|---|---|---|---|---|---|---|
| | | | | % HMW | % Native | % LMW | % Acidic | % Main | % Basic |
| pH 4.5, Acetate | Pass | 0.00 | 87 | 5.2 | −7.2 | 2.0 | 11.1 | −15.4 | 4.3 |
| pH 5.0, Acetate | Pass | 0.00 | 82 | 5.0 | −5.9 | 0.9 | 7.5 | −10.9 | 3.4 |
| pH 5.5, Acetate | Pass | 0.00 | 90 | 4.7 | −5.4 | 0.7 | 12.8 | −13.7 | 0.9 |
| pH 5.5, Histidine | Pass | 0.00 | 97 | 5.6 | −6.4 | 0.8 | 10.8 | −12.4 | 1.6 |
| pH 6.0, Histidine | Pass | 0.00 | 86 | 1.9 | −2.4 | 0.6 | 13.4 | −12.6 | −0.7 |
| pH 6.5, Histidine | Pass | 0.00 | 84 | 1.2 | −1.8 | 0.7 | 25.4 | −21.3 | −4.1 |

TABLE 1-continued

Effect of Buffer and pH on the Stability of 5 mg/mL mAb1 Incubated at 45° C. for 28 Days

| pH 6.0, Phosphate | Pass | 0.01 | 92 | 3.7 | −4.3 | 0.6 | 24.8 | −21.8 | −3.0 |
| pH 6.5, Phosphate | Pass | 0.03 | 91 | 4.9 | −5.8 | 0.9 | 49.6 | −40.3 | −9.3 |
| pH 7.0, Phosphate | Pass | 0.03 | 95 | 10.4 | −11.6 | 1.2 | 56.5 | −42.2 | −14.3 |

[a]Reported as a relative change in purity relative to the starting material. The starting material (no incubation) contains ≥97.2% native peak by SE-UPLC and ≥49.0% main peak by CEX-UPLC in all formulations.
CEX = Cation exchange;
DS = Drug substance;
HMW = High molecular weight;
LMW = Low molecular weight;
OD = Optical density;
RP = Reverse phase;
SE = Size exclusion;
UPLC = Ultra-performance liquid chromatography Based on results from CEX-UPLC analysis, maximum protein stability was observed when mAb1 was formulated between pH 5.5 and 6.0 in histidine buffer or between pH 5.0 and 5.5 in acetate buffer. These analyses also revealed that aggregation (i.e. formation of HMW species), fragmentation (i.e. formation of LMW species), and formation of charge variants were the main degradation pathways. Histidine buffer was selected as the formulation buffer because it provided the best overall level of protein stabilization with respect to formation of HMW and LMW species and formation of charge variants. A pH of 6.0 was chosen for the formulation because formation of HMW species and charge variants, which are the major degradation pathways, were minimized at this pH. Based on these results, 10 mM histidine buffer at pH 6.0 was chosen for the mAb1 formulation.

Example 5: pH Screening in Histidine Buffers

The effect of buffer and pH on the thermal stability of mAb1 was examined in high concentration liquid formulations. 150 mg/mL mAb1 was incubated at 45° C. for 28 days in a series of histidine buffers ranged at pH 5.3, 5.5, 5.8, 6.0 and 6.3 with and without thermal stabilizers. With 9% sucrose, based on results from SE-UPLC analysis, maximum protein stability was observed when mAb1 was formulated between pH 5.8 and 6.3 in histidine buffer (FIG. 1). Based on results from CEX-UPLC analysis, maximum protein stability was observed when mAb1 was formulated between pH 5.3 and 6.0 in histidine buffer (Table 2).

TABLE 2

Effect of pH on the Stability of 150 mg/mL mAb1 Incubated at 45° C. for 28 Days

| Formulation | 150 mg/mL mAb1, 10 mM histidine |
| Fill Volume | 0.4 mL |
| Container/Closure | 2 mL Type 1 borosilicate glass vial with a FluroTec ®-coated 4432/50 butyl rubber stopper |

| pH/Stabilizer | Color and Appearance | Turbidity (Increase in OD at 405 nm) | % Protein Recovered by RP-UPLC | Change in Purity by SE-UPLC[a] | | | Change in Charge Variants by CEX-UPLC[a] | | |
| --- | --- | --- | --- | --- | --- | --- | --- | --- | --- |
| | | | | % HMW | % Native | % LMW | % Acidic | % Main | % Basic |
| pH 5.3/none | Fail[b] | NA | NA | NA | NA | NA | NA | NA | NA |
| pH 5.5/none | Fail[b] | NA | NA | NA | NA | NA | NA | NA | NA |
| pH 5.8/none | Fail | 0.40 | 95 | 46.2 | −46.4 | 0.3 | 6.4 | −10.2 | 3.9 |
| pH 6.0/none | Fail | 0.51 | 99 | 41.2 | −41.5 | 0.3 | 10.6 | −7.3 | −3.3 |
| pH 6.3/none | Fail | 0.65 | 98 | 35.0 | −35.4 | 0.4 | 19.6 | −14.3 | −5.3 |
| pH 5.3/9% (w/v) Sucrose | Pass | 0.14 | 95 | 41.9 | −42.1 | 0.3 | 7.9 | −11.1 | 3.2 |
| pH 5.5/9% (w/v) Sucrose | Pass | 0.16 | 99 | 30.8 | −31.2 | 0.4 | 9.5 | −12.5 | 2.9 |
| pH 5.8/9% (w/v) Sucrose | Pass | 0.13 | 100 | 22.8 | −23.3 | 0.5 | 9.7 | −11.8 | 2.1 |
| pH 6.0/9% (w/v) Sucrose | Pass | 0.14 | 99 | 19.4 | −19.9 | 0.5 | 13.5 | −14.5 | 1.0 |
| pH 6.3/9% (w/v) Sucrose | Pass | 0.15 | 98 | 16.9 | −17.4 | 0.5 | 22.4 | −22.1 | −0.4 |

[a]Reported as a relative change in purity relative to the starting material. The starting material (no incubation) contains ≥94.0% native peak by SE-UPLC and ≥48.7% main peak by CEX-UPLC in all formulations
[b]Sample gelled. No father analysis was performed.
NA = Not applicable
CEX, cation exchange;
HMW, high molecular weight;
LMW, low molecular weight;
OD, optical density;
RP, reverse phase;
SE, size exclusion;
UPLC, ultra performance liquid chromatography These analyses also revealed that aggregation (i.e. formation of HMW species), and formation of charge variants were the main degradation pathways. A pH of 6.0 was chosen for the DP formulation because formation of HMW species and charge variants, which are the major degradation pathways, were minimized at this pH. Based on these results, 10 mM histidine buffer at pH 6.0 was chosen for the mAb1 high concentration DP formulation.

Example 6: Selection of Protectants Against Agitation Stress

Stabilizers such as surfactants and organic co-solvents are often added to the antibody formulations to protect the protein from agitation-induced aggregation. The effect of organic co-solvents and surfactants on the agitation stress stability and thermal stability of 5 mg/mL mAb1 was examined in liquid formulations. The following co-solvent and surfactants were evaluated: 0.1% polysorbate 20, 0.1% polysorbate 80, and 1.0% PEG3350. The results of agitation stress stability studies are summarized in Table 3.

min of vortexing. In the presence of 1% PEG3350, the solution became cloudy, and exhibited an increase in turbidity (Table 3). In contrast, 0.1% polysorbate 20 and 0.1% polysorbate 80 both protected mAb1 from agitation-induced instability to the same extent (Table 3).

However, the formulation containing 0.1% polysorbate 80 exhibited a decreased amount of aggregates compared to the formulation containing 0.1% polysorbate 20 when incubated at 45° C. (Table 4). 0.1% polysorbate 80 was chosen as the surfactant for the mAb1 DP formulation because it stabilized the protein to agitation stress, had less negative effect on protein thermal stability than polysorbate 20 (as determined by both SE-UPLC and CEX-UPLC analyses), and has a safe history of use in monoclonal antibody formulations.

TABLE 3

Effect of Organic Co-solvents and Surfactants on the Stability of 5 mg/mL mAb1 After Agitation (120 Min of Vortexing)

| Formulation | 5 mg/mL mAb1, 10 mM histidine, pH 6.0 |
| Fill Volume | 0.4 mL |
| Container | 2 mL Type 1 borosilicate glass vial with a FluorTec ® coated 4432/50 butyl rubber stopper |

| Co-solvent/Surfactant | Color and Appearance | Turbidity (Increase in OD at 405 nm) | PH | % Protein Recovered by RP-UPLC | Change in Purity by SE-UPLC[a] | | | Change in Charge Variants by CEX-UPLC[a] | | |
|---|---|---|---|---|---|---|---|---|---|---|
| | | | | | % HMW | % Native | % LMW | % Acidic | % Main | % Basic |
| No co-solvent/surfactant | Fail | 1.69 | 6.0 | 76 | 15.3 | −23.7 | −8.4 | −2.3 | −1.7 | 3.9 |
| 5% (w/v) sucrose | Fail | 1.75 | 6.0 | 64 | 9.4 | −12.8 | 3.4 | −1.7 | −0.1 | 1.8 |
| 0.1% (w/v) polysorbate 20[b] | Pass | 0.00 | 6.0 | 102 | −0.1 | −0.8 | 0.8 | 0.2 | 0.2 | −0.3 |
| 0.1% (w/v) polysorbate 80[b] | Pass | 0.00 | 6.0 | 100 | −0.2 | −0.5 | 0.4 | 0.2 | −0.1 | −0.1 |
| 1% (w/v) PEG3350[b] | Fail | 0.20 | 6.0 | 93 | 0.3 | −0.5 | 0.2 | −0.2 | −0.3 | 0.4 |

[a]Reported as a relative change in purity relative to the starting material. The starting material (no incubation) contains ≥98.2% native peak by SE-UPLC and ≥49.1% main peak by CEX-UPLC in all 5 formulations.
[b]The formulation also contains 5% sucrose.
CEX = Cation exchange;
HMW = High molecular weight;
LMW = Low molecular weight;
OD = Optical density;
RP = Reverse phase;
SE = Size exclusion;
UPLC = Ultra-performance liquid chromatography mAb1 was unstable when agitated by vortexing for 120 min in the absence of an organic co-solvent or surfactant. After agitation by vortexing in the absence of co-solvent or surfactant, the solution became cloudy, exhibited a substantial increase in turbidity, and had a 15.3% increase in aggregates as determined by SE-UPLC, as well as 24% loss in protein recovery by RP-UPLC (Table 3). 1% PEG3350 did not provide sufficient stabilization of mAb1 after 120

Example 7: Selection of Protectants Against Thermal Stress

Stabilizers such as sucrose are often added to antibody formulations to increase the thermal stability of the protein in liquid formulations. Five (5) mg/mL mAb1 in a liquid formulation exhibited improved stability when formulated with 5% sucrose and incubated under accelerated conditions (Table 4).

TABLE 4

Effect of Organic Co-solvents and Surfactants on the Stability of 5 mg/mL mAb1
Incubated at 45° C. for 29 Days Formulation      5 mg/mL mAb1, 10 mM histidine, pH 6.0
Fill Volume      0.4 mL
Container/Closure 2 mL Type 1 borosilicate glass vial with a FluorTec ® coated 4432/50 butyl rubber stopper

| Co-solvent/Surfactant | Color and Appearance | Turbidity (Increase in OD at 405 nm) | pH | % Protein Recovered by RP-UPLC | Change in Purity by SE-UPLC[a] | | | Change in Charge Variants by CEX-UPLC[a] | | |
|---|---|---|---|---|---|---|---|---|---|---|
| | | | | | % HMW | % Native | % LMW | % Acidic | % Main | % Basic |
| No co-solvent/surfactant | Pass | 0.00 | 6.1 | 96 | 2.8 | −3.2 | 0.5 | 10.8 | −10.7 | −0.2 |
| 5% (w/v) Sucrose | Pass | 0.01 | 6.1 | 99 | 1.6 | −2.0 | 0.3 | 12.6 | −11.7 | −0.9 |
| 0.1% (w/v) polysorbate 20[b] | Pass | 0.00 | 6.0 | 92 | 27.6 | −28.4 | 0.7 | 0.1 | −24.0 | 23.9 |
| 0.1% (w/v) polysorbate 80 | Pass | 0.00 | 6.1 | 96 | 12.8 | −14.1 | 0.9 | 4.4 | −20.4 | 15.9 |
| 1% (w/v) PEG3350 | Pass | 0.00 | 6.1 | 90 | 8.4 | −8.0 | −0.4 | 0.4 | −25.0 | 24.5 |

[a]Reported as a relative change in purity relative to the starting material. The starting material (no incubation) contains ≥98.2% native peak by SE-UPLC and ≥49.1% main peak by CEX-UPLC in all 5 formulations
[b]The formulation also contains 5% sucrose
CEX = Cation exchange;
HMW = High molecular weight;
LMW = Low molecular weight;
OD = Optical density;
RP = Reverse phase;
SE = Size exclusion;
UPLC = Ultra-performance liquid chromatography After incubation at 45° C. for 29 days, the relative amount of HMW species increased by 1.7% in the formulation containing 5% sucrose compared to a 2.8% increase in the control formulation without sucrose. For this reason, sucrose was chosen as the thermal stabilizer. To make the formulation isotonic and to maximize the thermal stability, the sucrose concentration was increased to 10% for the mAb1 formulation.

Example 8: Optimization of Stabilizers

The goal of optimizing the thermal stabilizers was to identify the stabilizing components that could be used to develop a DP formulation supporting an antibody concentration of up to 200 mg/mL. 10% sucrose was selected in the initial formulation. It was found that with 10% sucrose, the viscosity of mAb1 was about 20 cP at 20° C. and was considered too high for a robust late stage and commercial product. Therefore, a modified mAb1 formulation was needed that exhibited both favorable stability and lower viscosity.

Sucrose was chosen as the thermal stabilizer for mAb1 during the low concentration formulation development. For the high concentration formulation development, different concentrations of sucrose and L-proline were evaluated on the stability and viscosity of the mAb1 at 150 and 175 mg/mL concentrations at 25° C. (Table 5) and at 40° C. for 1 month. The formation of HMW species decreased with increasing sucrose concentrations when the formulations were incubated at 40° C. for 28 days. 3% L-proline provided similar stabilization to 5% sucrose, and the maximum stabilization was observed with 9% of sucrose.

Although 9% sucrose provided slightly better stabilization comparing with 3% L-proline, it also increased the formulation viscosity. At 175 mg/mL, mAb1 formulation with 9% of sucrose has a viscosity of 27 centipoise, which pose manufacturing and administration challenges. The 175 mg/mL mAb1 formulation with 3% of proline has a viscosity of approximately 20 centipoise, which is manageable with the current manufacturing process.

TABLE 5

Accelerated Stability of high concentration mAb1 with thermal stabilizers at 25° C.
for 1 month Formulation      210 mg/mL mAb1, 10 mM Histidine pH 6.0
Fill Volume      0.8 mL
Container/Closure 5 mL polycarbonate vial with silicone lined polypropylene screw cap

| Excipients | Color and Appearance | Turbidity (Increase in OD at 405 nm) | pH | % mAb1 Recovered by RP-UPLC | Purity by SE-UPLC | | | Charged Variants by CEX-UPLC | | |
|---|---|---|---|---|---|---|---|---|---|---|
| | | | | | % HMW | % Native | % LMW | % Acidic | % Main | % Basic |
| Starting Material[a] | Pass | 0.00 | 6.0 | 100 | 2.9 | 96.6 | 0.5 | 25.3 | 47.4 | 27.3 |

TABLE 5-continued

| | | | | | | | | | |
|---|---|---|---|---|---|---|---|---|---|
| 3% Proline | Pass | 0.01 | 6.0 | 106 | 4.1 | 95.3 | 0.6 | 25.2 | 47.1 | 27.8 |
| 3% Sucrose | Pass | 0.00 | 6.0 | 107 | 4.7 | 94.8 | 0.6 | 25.2 | 46.5 | 28.3 |
| 5% Sucrose | Pass | 0.00 | 6.0 | 104 | 4.7 | 94.8 | 0.6 | 25.1 | 46.1 | 28.8 |
| Formulation | FDS/DP: 150 mg/mL or 175 mg/mL mAb1, 10 mM Histidine pH 6.0, 0.1% PS 80 |
| Fill Volume | 0.4 mL |
| Container/Closure | 2 mL Type 1 borosilicate glass vial with a FluroTec ® coated 4432/50 butyl rubber stopper |
| Starting Material[a] | Pass | 0.00 | 6.1 | 100 | 2.3 | 97.4 | 0.4 | 24.9 | 50.2 | 24.9 |
| 9% Sucrose, 0.1% PS 80 | Pass | 0.00 | 6.1 | 101 | 3.7 | 95.7 | 0.7 | 28.4 | 47.7 | 23.9 |
| 3% Proline 0.1% PS 80 | Pass | 0.00 | 6.1 | 101 | 3.7 | 95.7 | 0.7 | 26.5 | 47.7 | 25.8 |

Figure 2B:
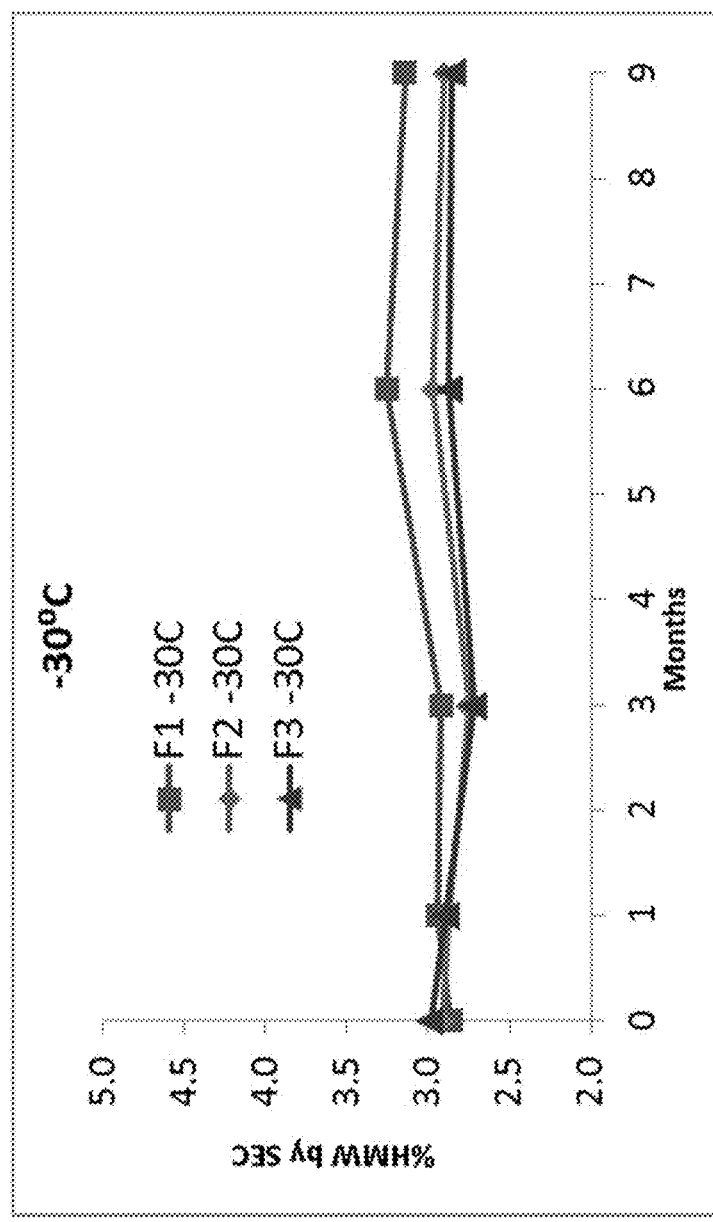
Figure 2C:
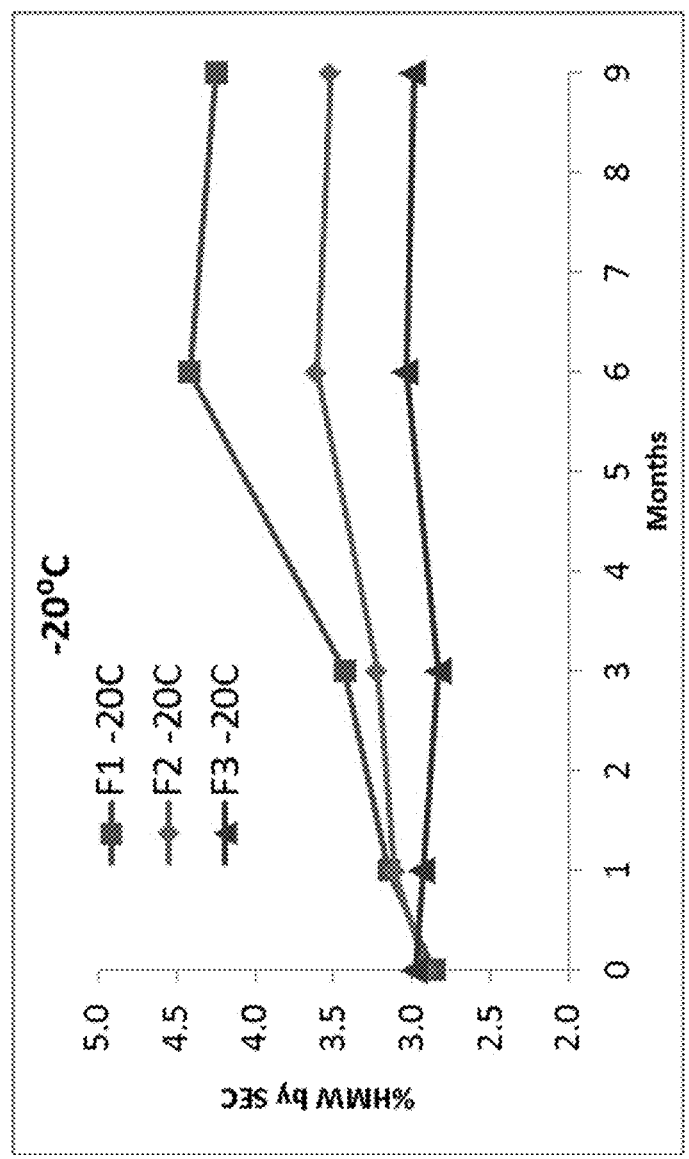

[a]pH, SE-UPLC and CEX-UPLC 'Starting Material' results are the average values of the starting formulations However, based on storage stability at −20° C., −30° C. and −80° C., it was found that the formulation with 3% proline was not as stable as the formulations with sucrose (FIGS. 2A, 2B, and 2C). As shown in FIGS. 2A, 2B, and 2C, formulation F3 (with 5% sucrose) was stable at −20° C., −30° C. and −80° C. with 3% HMW species.

The effect of L-proline in stabilizing mAb1 was examined with the 50 mg/mL formulation. After incubation at 45° C. for 28 days, the formulation with L-proline showed lower levels of HMW species relative to the formulation without L-proline, showing that L-proline stabilizes the antibody at a concentration of 50 mg/mL (Table 6). In addition, the impact of L-proline on antibody protein structure was examined by biophysical techniques (Fourier transform infrared spectroscopy, CD spectroscopy, fluorescence emission spectroscopy, and differential scanning calorimetry). The results showed that L-proline did not perturb the secondary and tertiary structure of the antibody.

TABLE 6

Effect of stabilizers on the stability of 50 mg/ml mAb1 after incubation at 45° C. for 28 days

| Formulation | 50 mg/mL mAb1, 10 mM L-histidine, 5% sucrose, pH 6.0, 0.2% polysorbate 80 |
| Fill Volume | 0.6 mL |
| Container/Closure | 2 mL Type 1 glass vial with a FluorTec ®-coated 4432/50 chlorobutyl stopper |

| Stabilizer (% w/v) | Color and Appearance | Turbidity (Increase in OD at 405 nm) | pH | % Protein Recovered by RP-UPLC | Change Purity by SE-UPLC[a] | | | Change in Charge Variants by CEX-UPLC[a] | | |
|---|---|---|---|---|---|---|---|---|---|---|
| | | | | | % HMW | % Monomer | % LMW | % Acidic | % Main | % Basic |
| — | Pass | 0.02 | 6.0 | 96 | 12.1 | −12.7 | 0.6 | 10.8 | −11.9 | 1.0 |
| 1.5% L-proline | Pass | 0.02 | 6.1 | 96 | 11.3 | −11.9 | 0.6 | 11.0 | −11.8 | 0.8 |
| 3.0% L-proline | Pass | 0.01 | 6.0 | 96 | 10.9 | −11.5 | 0.6 | 12.8 | −12.9 | 0.1 |

[a]Reported as a change in purity relative to the starting material. The starting material (no incubation) contains ≥98.5% Monomer peak by SE-UPLC and ≥52.8% main peak by CEX-UPLC in all three formulations.

CEX, cation exchange;

DS, drug substance;

HMW, high molecular weight;

LMW, low molecular weight;

OD, optical density;

RP, reverse phase;

SE, size exclusion;

UPLC, ultra performance liquid chromatography

The effect of different stabilizers on the thermal stability of high concentrations (150 and 175 mg/mL) mAb1 was further examined in liquid formulations. The stabilizers evaluated were 9% (w/v) sucrose, 3% (w/v) L-proline, and 5% (w/v) sucrose with 1.5% (w/v) L-proline. The results of the accelerated stability study are summarized in Table 7.

Example 9: Selection of Viscosity Modifiers

The viscosity of protein formulations increases exponentially as the protein concentration increases. When the viscosity begins to exceed about 10 to 15 cP at 20° C., viscosity of the formulation must be taken into account

TABLE 7

Effect of Stabilizers on the Stability of mAb1 after Incubation at 25° C. and 40° C.

Formulation: 150 or 175 mg/mL mAb1, 10 mM histidine, pH 6.0, 0.1% polysorbate 80
Fill Volume: 0.5 mL
Container/Closure: 2 mL Type 1 borosilicate glass vial with a FluorTec ®-coated 4432/50 butyl rubber stopper
Incubation: 25° C. for 3 months

| Stabilizer (% w/v) | mAb1 Conc. (mg/mL) | Color and Appearance | Turbidity (Increase in OD at 405 nm) | pH | % Protein Recovered by RP-UPLC | Change Purity by SE-UPLC$^a$ | | | Change in Charge Variants by CEX-UPLC$^a$ | | |
|---|---|---|---|---|---|---|---|---|---|---|---|
| | | | | | | % HMW | % Native | % LMW | % Acidic | % Main | % Basic |
| 9% Sucrose | 150 | Pass | 0.02 | 6.2 | 110 | 2.6 | −2.8 | 0.2 | 6.0 | −4.2 | −1.9 |
| 3% L-proline | 175 | Pass | 0.00 | 6.2 | 112 | 2.4 | −2.5 | 0.2 | 6.5 | −4.1 | −2.4 |
| 5% Sucrose, 1.5% L-proline | 175 | Pass | 0.00 | 6.2 | 110 | 2.3 | −2.6 | 0.2 | 6.0 | −3.7 | −2.4 |

40° C. for 28 days

| Incubation Stabilizer (% w/v) | mAb1 Conc. (mg/mL) | Color and Appearance | Turbidity (Increase in OD at 405 nm) | pH | % Protein Recovered by RP-UPLC | Change Purity by SE-UPLC$^a$ | | | Change in Charge Variants by CEX-UPLC$^a$ | | |
|---|---|---|---|---|---|---|---|---|---|---|---|
| | | | | | | % HMW | % Native | % LMW | % Acidic | % Main | % Basic |
| 9% Sucrose | 150 | Pass | 0.04 | 6.1 | 102 | 6.9 | −7.5 | 0.5 | 9.4 | −9.7 | 0.3 |
| 3% L-proline | 175 | Pass | 0.03 | 6.2 | 103 | 11.7 | −12.3 | 0.6 | 12.1 | −10.7 | −1.4 |
| 5% Sucrose, 1.5% L-proline | 175 | Pass | 0.03 | 6.1 | 103 | 8.8 | −9.4 | 0.7 | 11.4 | −10.2 | −1.2 |

Figure 3A:
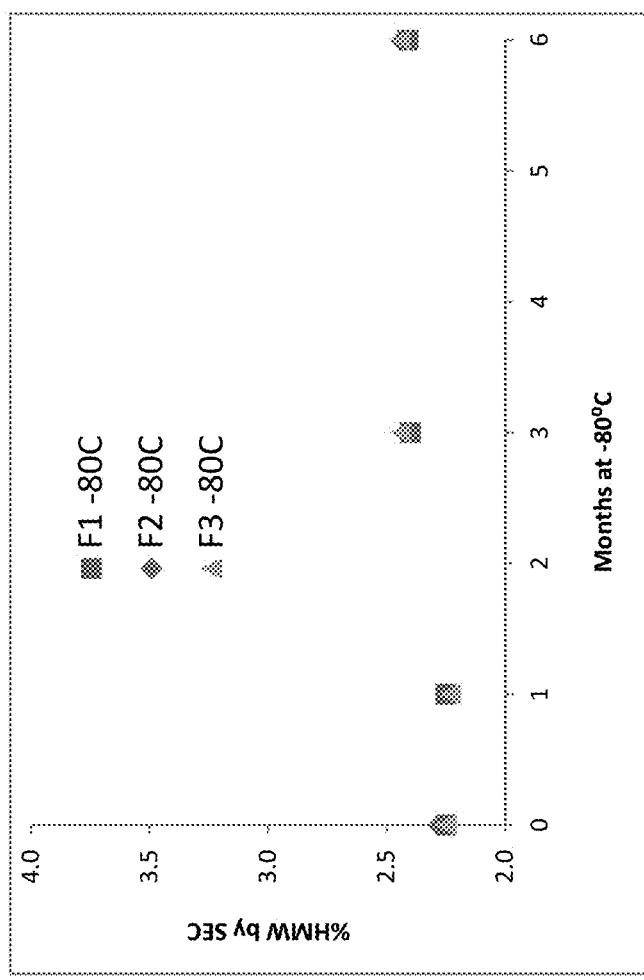
FIGS. 3A, 3B, and 3C show storage stability of three formulations F1, F2 and F3, wherein F1 comprises 150 mg/mL mAb1, 10 mM histidine, 9% sucrose and 0.2% polysorbate 80 (PS80), at pH 6.0; F2 comprises 175 mg/mL mAb1, 10 mM histidine, 3% proline and 0.2% PS80, at pH 6.0; and F3 comprises 175 mg/mL mAb1, 10 mM histidine, 5% sucrose, 1.5% proline and 0.2% PS80, at pH 6.0. Storage stability is measured by % high molecular weight species (HMW) generated upon storage at −80° C.
Figure 3B:
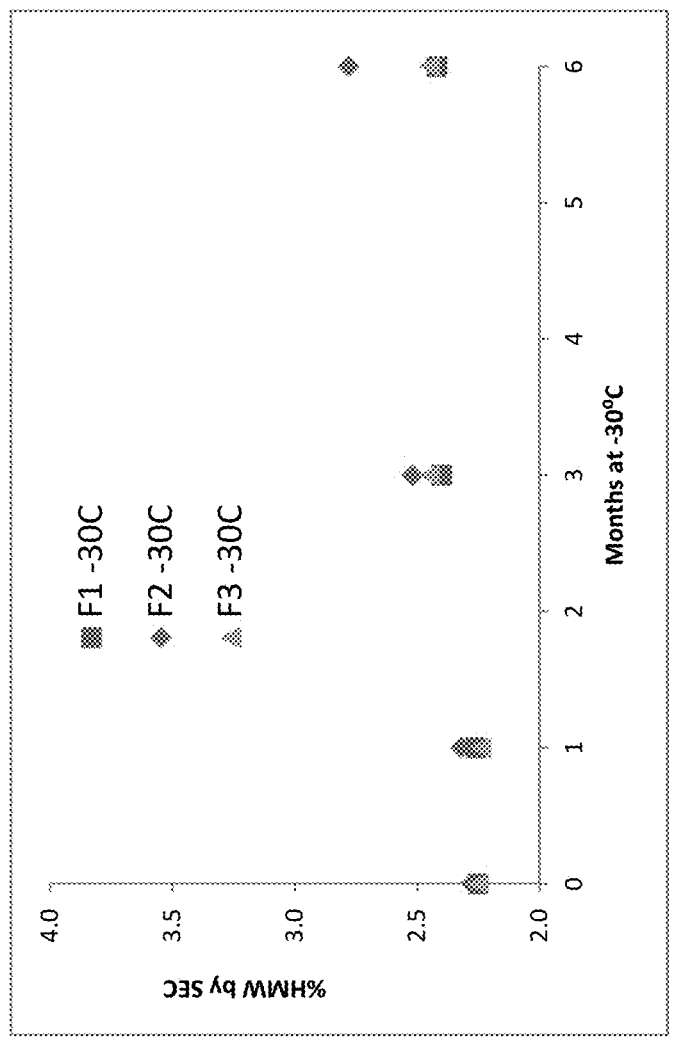
Figure 3C:
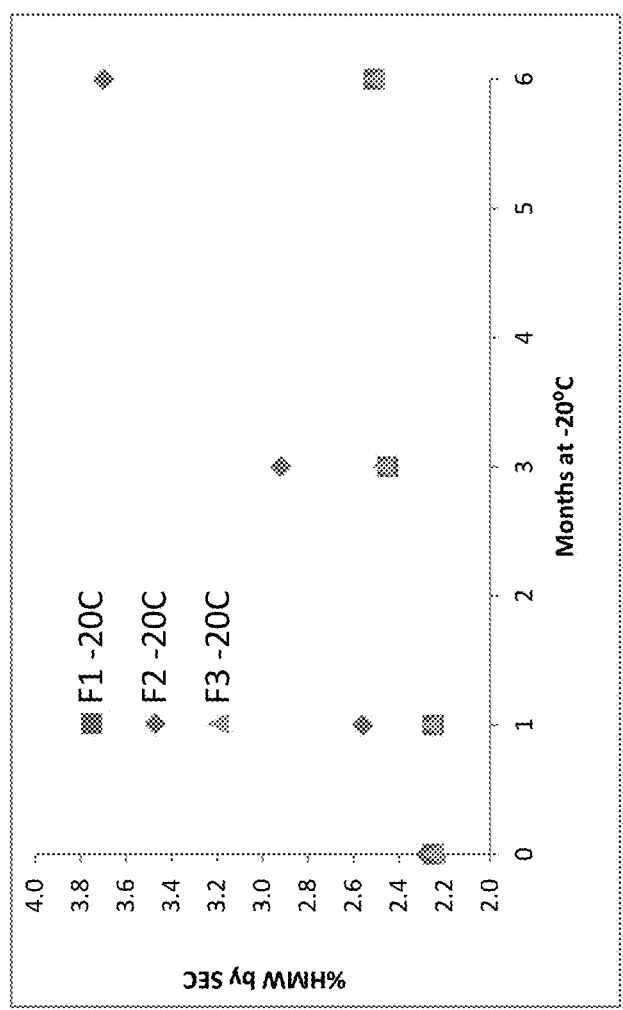

$^a$Reported as a change in purity relative to the starting material. The starting material (no incubation) contains ≥97.3% native peak by SE-UPLC and ≥49.6% main peak by CEX-UPLC in all three formulations.
CEX, cation exchange;
HMW, high molecular weight;
LMW, low molecular weight;
OD, optical density;
RP, reverse phase;
SE, size exclusion;
UPLC, ultra performance liquid chromatography After incubation at 40° C. for 28 days, 9% sucrose provided the best stabilization and had the highest viscosity among the high concentration formulations. The 5% sucrose/1.5% L-proline formulation ranked second for stability after 28 days at 40° C. After incubation at 25° C. for three months, the stability of mAb1 was nearly the same in all of the formulations examined; however, the formulation with 5% sucrose/1.5% L-proline was slightly better than the other two formulations. However, upon incubation at −20° C., −30° C. and −80° C., sucrose at 5% and at 9% provided better stability than 3% proline (FIGS. 3A, 3B, and 3C). The viscosity of 175 mg/mL mAb1 with 5% sucrose/1.5% L-proline has a viscosity of 14 cP at 20° C. To provide a formulation that yields an isotonic solution and achieves the best balance between stability and viscosity, 5% sucrose/1.5% L-proline was selected for development of an antibody late phase DP formulation.

when developing a formulation: this is simply because viscosity correlates with the ease of injection through a prefilled syringe (PFS) or other needle-based delivery device; more importantly maintaining a reasonably low viscosity is critical for the development of a delivery device, such as autoinjector. The effect of excipients on formulation viscosity was examined in liquid formulation with the following potential viscosity modifiers, proline, arginineHCl, histidineHCl, magnesium acetate and NaCl. FIG. 4 summarizes the viscosity of 150 mg/mL mAb1 with the viscosity modifiers. ArginineHCl, histidineHCl, magnesium acetate and NaCl at 25-100 mM lower the viscosity of 150 mg/mL mAb1 formulations.

Impact of the viscosity modifiers on stability of mAb1 formulation was also examined. 150 mg/mL mAb1 formulations with viscosity modifiers such as arginineHCl, histidineHCl, magnesium acetate and NaCl were prepared and incubated at 45° C. for 28 days. The results are shown in FIG. 5. It was found that maximum protein stability was observed when mAb1 was formulated without the viscosity modifiers; all these viscosity modifying salts negatively impact the mAb1 stability. Therefore salts were not included in the final formulation.

L-proline, as a stabilizer, minimized solution viscosity for antibody concentrations at or above 50 mg/mL. The results of the accelerated stability studies for high concentration antibody with varying amounts of L-proline, with and without sucrose, are summarized in Table 7. After incubation at 25° C. for three months, the formulation with 5% sucrose/1.5% L-proline provided slightly improved stability relative to the other two formulations with respect to formation of HMW species. After incubation at 40° C. for 28 days, the formulation containing 9% sucrose provided the best stabilization, and the formulation with 5% sucrose/1.5% L-proline formulation ranked second. The formulation with 9% sucrose has a viscosity of 20 cP at 175 mg/mL antibody, while the viscosity of 175 mg/mL formulation with 5% sucrose/1.5% L-proline has a viscosity of 14 cP at 20° C. Adding L-proline to the formulation was important for lowering the viscosity at elevated protein concentrations as well as stabilizing the antibody.

In summary, 5% sucrose/1.5% L-proline was selected for both 50 mg/mL and high concentration antibody formulations. This combination of excipients achieved an isotonic formulation with acceptable stability and viscosity at all antibody concentrations tested (up to 175 mg/mL).

Example 10: Optimization of Polysorbate (PS) Concentration

During formulation development, higher order molecular weight species formation and an increase in turbidity was observed when the mAb1 formulation was agitated without surfactant. The protein was stabilized to agitation by addition of polysorbate 80 (PS 80). During high concentration mAb1 liquid formulation development, instability to agitation was observed as an increase in higher order molecular weight species. A study was carried out to determine the minimum amount of polysorbate 80 needed to protect up to 175 mg/mL mAb1 from agitation-induced instability. The formulations in this study contained 5% sucrose and 1.5% L-proline so that the effect of polysorbate 80 could be studied with a formulation composition that was more representative of the final formulation. The nominal polysorbate 80 concentrations included in the study were 0%, 0.02%, 0.04%, 0.06%, 0.08%, 0.1%, 0.15%, and 0.2% (w/v). In the absence of polysorbate 80, the solution became cloudy and exhibited a substantial increase in turbidity after agitation by vortexing. A polysorbate 80 concentration-dependent reduction in the amount of % HMW after 120 minutes of agitation was observed. A concentration of 0.15-0.2% polysorbate 80 was found to be sufficient to stabilize 150 mg/mL and 175 mg/mL mAb1 to agitation induced aggregation (Table 8). The addition of 0.2% (w/v) (nominal value) polysorbate 80 completely prevented formation of the HMW species after agitation for 120 minutes.

TABLE 8

Stability of 150 mg/mL and 175 mg/mL mAb1 with PS 80 after 120 min of agitation

| Fill Volume | 0.4 mL |
| Container/Closure | 2 mL Type 1 borosilicate glass vial with a FluroTec ® coated 4432/50 butyl rubber stopper |

| Formulation | [PS 80] | Color and Appearance | Turbidity (Increase in OD at 405 nm) | pH | % mAb1 Recovered by RP-UPLC | Increase in % HMW by SE-UPLC |
| --- | --- | --- | --- | --- | --- | --- |
| 150 mg/mL | 0.00 | Fail | 0.38 | 6.0 | Not Applicable | |
| mAb1 | 0.02 | Pass | 0.00 | 6.0 | 97 | 4.7 |
| 10 mM | 0.04 | Pass | 0.00 | 6.0 | 100 | 0.3 |
| histidine, pH | 0.06 | Pass | 0.00 | 6.0 | 102 | 0.3 |
| 6.0 | 0.08 | Pass | 0.04 | 6.0 | 99 | 0.0 |
| 9% sucrose | 0.10 | Pass | 0.01 | 6.0 | 101 | 0.1 |
| | 0.15 | Pass | 0.00 | 6.0 | 98 | 0.1 |
| | 0.20 | Pass | 0.00 | 6.0 | 106 | 0.1 |
| 175 mg/mL | 0.00 | Fail | 0.38 | 6.0 | Not Applicable | |
| mAb1 | 0.02 | Pass | 0.06 | 6.1 | 100 | 7.0 |
| 10 mM | 0.04 | Pass | 0.00 | 6.0 | 97 | 2.4 |
| histidine, pH | 0.06 | Pass | 0.01 | 6.1 | 700 | 2.3 |
| 6.0, | 0.08 | Pass | 0.03 | 6.1 | 98 | 0.9 |
| 3% proline | 0.10 | Pass | 0.00 | 6.1 | 102 | 0.4 |
| | 0.15 | Pass | 0.00 | 6.1 | 102 | 0.1 |
| | 0.20 | Pass | 0.00 | 6.1 | 101 | 0.1 |
| 175 mg/mL | 0.00 | Fail | 0.36 | 6.1 | Not Applicable | |
| mAb1 | 0.02 | Pass | 0.01 | 6.1 | 97 | 3.5 |
| 10 mM | 0.04 | Pass | 0.01 | 6.1 | 98 | 2.0 |
| histidine, pH | 0.06 | Pass | 0.01 | 6.1 | 100 | 1.3 |
| 6.0, | 0.08 | Pass | 0.01 | 6.1 | 99 | 1.0 |
| 5% sucrose, | 0.10 | Pass | 0.01 | 6.0 | 102 | 0.3 |
| 1.5% proline | 0.15 | Pass | 0.00 | 6.1 | 101 | 0.2 |
| | 0.20 | Pass | 0.00 | 6.1 | 98 | 0.0 |

Table 9 details the effect of polysorbate 80 concentration on the stability of 175 mg/mL mAb1 after agitation (120 minutes of vortexing).

TABLE 9

Effect of Polysorbate 80 Concentration on the Stability of 175 mg/mL mAb1 after Agitation (120 minutes of Vortexing)

Formulation: 175 mg/mL mAb1, 10 mM histidine, pH 6.0, 5% (w/v) sucrose, 1.5% (w/v) L-proline
Fill Volume: 0.4 mL
Container/Closure: 2 mL Type 1 borosilicate glass vial with a FluorTec ®-coated 4432/50 butyl rubber stopper

| Nominal PS 80 Conc. (% w/v) | Color and Appearance | Turbidity (Increase in OD at 405 nm) | pH | % Protein Recovered by RP-UPLC | Change in Purity by SE-UPLC[a] | | | Change in Charge Variants by CEX-UPLC[a] | | |
|---|---|---|---|---|---|---|---|---|---|---|
| | | | | | % HMW | % Native | % LMW | % Acidic | % Main | % Basic |
| 0.00% | Fail | 0.36 | 6.0 | NA | NA | NA | NA | NA | NA | NA |
| 0.02% | Pass | 0.01 | 6.0 | 97 | 3.5 | −3.5 | 0.0 | −0.6 | 0.8 | −0.1 |
| 0.04% | Pass | 0.01 | 6.0 | 98 | 2.0 | −2.0 | 0.0 | 0.1 | −0.2 | −0.2 |
| 0.06% | Pass | 0.01 | 6.0 | 100 | 1.3 | −1.3 | 0.0 | −0.2 | 0.3 | −0.1 |
| 0.08% | Pass | 0.01 | 6.0 | 99 | 1.0 | −1.0 | 0.0 | −0.2 | 0.0 | 0.0 |
| 0.10% | Pass | 0.02 | 6.0 | 102 | 0.3 | −0.3 | 0.0 | 0.2 | 0.0 | 0.0 |
| 0.15% | Pass | 0.00 | 6.1 | 101 | 0.2 | −0.2 | 0.0 | 0.2 | −0.3 | 0.1 |
| 0.20% | Pass | 0.00 | 6.1 | 98 | 0.0 | 0.0 | 0.0 | 0.0 | −0.1 | 0.2 |

[a]Reported as a relative change in purity relative to the starting material. The starting material (no incubation) contains ≥97.4% native peak by SE-UPLC and ≥48.2% main peak by CEX UPLC in all formulations.
CEX, cation exchange;
HMW, high molecular weight;
LMW, low molecular weight;
NA, not available;
OD, optical density;
RP, reverse phase;
SE, size exclusion;
UPLC, ultra-performance liquid chromatography The ability of 0.2% (w/v) polysorbate 80 to protect mAb1 from agitation-induced instability was confirmed by another study with the final formulation at 50 mg/mL (Table 10).

TABLE 10

Effect of PS80 Concentration on the Stability of 50 mg/mL mAb1 after Agitation (120 minutes of Vortexing)

Formulation: 50 mg/mL mAb1, 10 mM L-histidine, pH 6.0, 5% (w/v) sucrose, 1.5% (w/v) L-proline
Fill Volume: 0.6 mL
Container/Closure: 2 mL Type 1 glass vial with a FluorTec ®-coated 4432/50 chlorobutyl stopper

| Polysorbate 80 Conc. (% w/v) | Color and Appearance | Turbidity (Increase in OD at 405 nm) | pH | % Protein Recovered by RP-UPLC | Change in Purity by SE-UPLC[a] | | | Change in Charge Variants by CEX-UPLC[a] | | |
|---|---|---|---|---|---|---|---|---|---|---|
| | | | | | % HMW | % Monomer | % LMW | % Acidic | % Main | % Basic |
| 0.0% | Pass | 0.01 | 6.1 | 99 | 8.0 | −8.0 | 0.0 | 1.7 | −1.8 | −0.3 |
| 0.2% | Pass | 0.00 | 6.1 | 99 | 0.0 | 0.1 | −0.1 | −0.2 | 0.1 | −0.2 |

[a]Reported as a relative change in purity relative to the starting material. The starting material (no incubation) contains ≥98.5% Monomer peak by SE-UPLC and ≥52.8% main peak by CEX UPLC in all five formulations.
CEX, cation exchange;
DS, drug substance;
HMW, high molecular weight;
LMW, low molecular weight;
NA, not available;
OD, optical density;
RP, reverse phase;
SE, size exclusion;
UPLC, ultra performance liquid chromatography Based on these results, 0.2% (w/v) polysorbate 80 was selected as the surfactant because it provided sufficient stabilization to prevent formation of HMW species under agitation stress.

Example 11: Storage and Stress Stability of Exemplary Formulations

The storage stability of 50 mg/mL and 175 mg/mL mAb1 formulations in glass vials are shown in Table 11 and Table 12, and the accelerated and stress stability data from the two formulations are shown in Table 13 and Table 14, respectively. Research stability studies demonstrated that the 50 mg/mL and 175 mg/mL mAb1 formulation in glass vials are stable for at least 24 months when stored at 2° C. to 8° C. In addition, the 50 mg/mL mAb1 formulation also exhibited excellent stability under accelerated and stress conditions. The formulation is stable when stored at 25° C. for at least 3 months and 40° C. for at least 7 days, demonstrating the compatibility of the 50 mg/mL formulation with the primary container closure components. No appreciable changes were observed in color or appearance, turbidity, particulate matter, pH, protein concentration, purity as measured by SE-UPLC or CEX-UPLC and iCIEF, and potency was maintained under these conditions.

TABLE 11

Research stability of 50 mg/mL formulation stored at 2-8° C.

| | |
|---|---|
| Formulation | 50 mg/mL mAb1, 10 mM L-histidine, 5% (w/v) sucrose, 1.5% (w/v) L-proline, and 0.2% (w/v) polysorbate 80, pH 6.0 |
| Fill Volume | 1.2 mL |
| Container/Closure | 3 mL Type 1 glass vials with a 13 mm FluroTec ®-coated coated 4432/50 chlorobutyl stopper |

| | | Length of Storage at 2-8° C. (months) | | | | | | | |
|---|---|---|---|---|---|---|---|---|---|
| Assay | | 0 | 1 | 3 | 6 | 9 | 12 | 18 | 24 | 36 |
| Color and Appearance | | Pass | Pass | Pass | Pass | Pass | Pass | Pass | Pass | |
| Turbidity (increase in OD at 405 nm) | | 0.00 | 0.00 | 0.00 | 0.00 | 0.00 | 0.00 | 0.00 | 0.00 | |
| Turbidity (NTU by nephelometry) | | 7.41 | 6.01 | 6.15 | 6.61 | 6.03 | 6.48 | 6.29 | 5.83 | |
| pH | | 6.0 | 6.0 | 6.0 | 6.1 | 6.0 | 6.0 | 6.0 | 6.0 | |
| Subvisible | ≥10 μm | 2 | NR | 21 | 8 | NR | 11 | 15 | 21 | |
| Particulate Analysis by HIAC (N/mL) | ≥25 μm | 0 | NR | 2 | 0 | NR | 1 | 1 | 1 | |
| Subvisible | 2 to 10 μm | 248 | NR | 887 | 1875 | NR | 607 | 1254 | 776 | |
| Particulate Analysis by MFI (N/mL) | ≥10 μm | 15 | NR | 26 | 44 | NR | 15 | 19 | 8 | |
| | ≥25 μm | 4 | NR | 3 | 17 | NR | 1 | 3 | 1 | |
| % Protein Recovered by RP-UPLC | | 100 | 100 | 98 | 103 | 101 | 105 | 98 | 98 | |
| Purity by MCE-SDS | Non-reduced; % main peak | 99.2 | NR | NR | 98.7 | NR | 98.9 | 99.2 | 99.2 | |
| | Reduced; % heavy + light chain | 100 | NR | NR | 100 | NR | 99.6 | 99.8 | 99.9 | |
| Purity by SE-UPLC | % HMW | 0.5 | 0.3 | 0.4 | 0.4 | 0.4 | 0.5 | 0.5 | 0.5 | |
| | % Monomer | 99.2 | 99.1 | 99.2 | 99.2 | 99.1 | 99.2 | 99.2 | 99.1 | |
| | % LMW | 0.4 | 0.5 | 0.4 | 0.4 | 0.5 | 0.3 | 0.4 | 0.4 | |
| Charge Variant Analysis by CEX-UPLC | % Acidic | 18.9 | 19.0 | 18.7 | 19.1 | 19.4 | 19.1 | 20.7 | 20.5 | |
| | % Main | 53.9 | 53.5 | 54.5 | 53.7 | 53.6 | 55.8 | 53.8 | 53.4 | |
| | % Basic | 27.3 | 27.6 | 26.8 | 27.2 | 27.1 | 25.1 | 25.5 | 26.0 | |
| Charge Variant Analysis by iCIEF | % Acidic | 31.9 | NR | NR | 32.3 | NR | 33.9 | 33.1 | 34.0 | |
| | % Main | 54.7 | NR | NR | 54.2 | NR | 54.0 | 54.0 | 53.9 | |
| | % Basic | 13.5 | NR | NR | 13.5 | NR | 12.1 | 12.9 | 12.1 | |
| % Relative Potency (bioassay) | | 126 | NR | NR | 127 | NR | 125 | 110 | 104 | |

CEX, Cation exchange; DS, Drug substance; HMW, High molecular weight; iCIEF, imaged capillary isoelectric-focusing, LMW, Low molecular weight; MFI, Microflow-imaging; Monomer, intact antibody; NR, Not required; OD, Optical density; RP, Reverse phase; SE, Size exclusion; UPLC, Ultra-performance liquid chromatography

TABLE 12

Research stability of 175 mg/mL formulation stored at 2-8° C.

| | |
|---|---|
| Formulation | 175 mg/mL mAb1, 10 mM L-histidine, 5% (w/v) sucrose, 1.5% (w/v) L-proline, and 0.2% (w/v) polysorbate 80, pH 6.0 |
| Fill Volume | 1.2 mL |
| Container/Closure | 3 mL Type 1 glass vials with a 13 mm FluroTec ®-coated coated 4432/50 chlorobutyl stopper |

| | | Length of Storage at 5° C. (months) | | | | | | | |
|---|---|---|---|---|---|---|---|---|---|
| Assay | | 0 | 1 | 3 | 6 | 9 | 12 | 18 | 24 | 36 |
| Color and Appearance | | Pass | Pass | Pass | Pass | Pass | Pass | Pass | Pass | |
| Turbidity (increase in OD at 405 nm) | | 0.00 | 0.01 | 0.00 | 0.00 | 0.00 | 0.00 | 0.00 | 0.00 | |
| Turbidity (NTU by nephelometry) | | 6.72 | 6.95 | 6.57 | 6.54 | 6.62 | 7.01 | 6.67 | 6.87 | |
| pH | | 6.0 | 6.0 | 6.0 | 6.0 | 6.0 | 6.0 | 6.0 | 6.1 | |
| Subvisible | ≥10 μm | 10 | NR | 28 | 131 | NR | 30 | 35 | 55 | |

TABLE 12-continued

Research stability of 175 mg/mL formulation stored at 2-8° C.

| | | | | | | | | | |
|---|---|---|---|---|---|---|---|---|---|
| Particulate Analysis by HIAC (N/mL) | ≥25 μm | 0 | NR | 11 | 56 | NR | 1 | 2 | 3 |
| Subvisible Particulate Analysis by MFI (N/mL) | 2 to 10 μm | 144 | NR | 441 | 244 | NR | 265 | 319 | 117 |
| | ≥10 μm | 22 | NR | 36 | 22 | NR | 29 | 28 | 8 |
| | ≥25 μm | 1 | NR | 11 | 7 | NR | 3 | 10 | 1 |
| % Protein Recovered by RP-UPLC | | 100 | 95 | 97 | 98 | 97 | 99 | 104 | 101 |
| Purity by MCE-SDS | Non-reduced; % main peak | 97.9 | NR | 98.1 | 98.0 | NR | 97.9 | 98.0 | 97.9 |
| | Reduced; % heavy + light chain | 100 | NR | 99.6 | 100 | NR | 99.8 | 99.8 | 99.8 |
| Purity by SE-UPLC | % HMW | 0.6 | 0.6 | 0.7 | 0.7 | 0.8 | 0.9 | 1.0 | 1.0 |
| | % Monomer | 99.1 | 98.9 | 99.1 | 98.7 | 98.7 | 98.7 | 98.6 | 98.6 |
| | % LMW | 0.4 | 0.5 | 0.3 | 0.5 | 0.5 | 0.5 | 0.4 | 0.4 |
| Charge Variant Analysis by CEX-UPLC | % Acidic | 18.7 | 18.3 | 18.1 | 18.7 | 19.1 | 19.0 | 19.0 | 20.3 |
| | % Main | 53.6 | 55.0 | 54.6 | 53.3 | 53.6 | 55.5 | 54.3 | 53.8 |
| | % Basic | 27.8 | 26.7 | 27.4 | 28.1 | 27.3 | 25.5 | 26.8 | 25.9 |
| Charge Variant Analysis by iCIEF | % Acidic | 31.8 | NR | 32.4 | 31.9 | NR | 33.9 | 32.3 | 32.0 |
| | % Main | 54.6 | NR | 54.6 | 54.9 | NR | 54.8 | 54.6 | 54.3 |
| | % Basic | 13.6 | NR | 13.1 | 13.2 | NR | 11.3 | 13.1 | 13.7 |
| % Relative Potency (bioassay) | | 102 | NR | NR | 118 | NR | 110 | 91 | 107 |

CEX, Cation exchange; DS, Drug substance; HMW, High molecular weight; iCIEF, imaged capillary isoelectric-focusing, LMW, Low molecular weight; MFI, Microflow-imaging; Monomer, intact antibody; NR, Not required; OD, Optical density; RP, Reverse phase; SE, Size exclusion; UPLC, Ultra-performance liquid chromatography

TABLE 13

Research stability of 50 mg/mL formulation stored at accelerated and stress conditions

| | |
|---|---|
| Formulation | 50 mg/mL mAb1, 10 mM L-histidine, 5% (w/v) sucrose, 1.5% (w/v) L-proline, 0.2% (w/v) polysorbate 80, pH 6.0 |
| Fill Volume | 1.2 mL |
| Container/Closure | 3 mL Type 1 glass vials with a 13 mm FluroTec ® coated 4432/50 chlorobutyl stopper |

| | | 25° C./60% RH Storage (months) | | | | 40° C. Storage (days) | | |
|---|---|---|---|---|---|---|---|---|
| Assay | | 0 | 1 | 3 | 6 | 7 | 14 | 28 |
| Color and appearance | | Pass | Pass | Pass | Pass | Pass | Pass | Pass |
| Turbidity (Increase in OD at 405 nm) | | 0.00 | 0.00 | 0.00 | 0.00 | 0.00 | 0.00 | 0.00 |
| Turbidity (NTU by Nephelometry) | | 7.41 | 6.05 | 6.54 | 6.90 | 6.10 | 6.60 | 6.93 |
| pH | | 6.0 | 6.0 | 6.0 | 6.1 | 6.0 | 6.0 | 6.0 |
| Subvisible particulate analysis by HIAC (#/mL) | ≥10 μm | 2 | NR | 17 | 21 | NR | NR | 18 |
| | ≥25 μm | 0 | NR | 0 | 1 | NR | NR | 1 |
| Subvisible particulate analysis by MFI (#/mL) | 2-10 μm | 248 | NR | 1618 | 1531 | NR | NR | 1543 |
| | ≥10 μm | 15 | NR | 29 | 47 | NR | NR | 41 |
| | ≥25 μm | 4 | NR | 2 | 15 | NR | NR | 15 |
| % Protein recovered by RP-UPLC | | 100 | 100 | 100 | 103 | 103 | 102 | 98 |
| Purity by MCE-SDS | Non-reduced; % main peak | 99.2 | NR | 99.1 | 98.8 | NR | NR | 98.9 |
| | Reduced; % heavy + light | 100 | NR | 99.5 | 100 | NR | NR | 99.5 |
| Purity by SE-UPLC | % HMW | 0.5 | 0.4 | 0.6 | 0.7 | 0.7 | 0.9 | 1.4 |
| | % Monomer | 99.2 | 99.0 | 99.1 | 98.8 | 98.9 | 98.5 | 97.9 |
| | % LMW | 0.4 | 0.5 | 0.3 | 0.5 | 0.5 | 0.6 | 0.7 |
| Charge variant analysis by CEX-UPLC | % Acidic | 18.9 | 19.3 | 21.8 | 27.0 | 19.9 | 22.5 | 27.2 |
| | % main | 53.9 | 53.4 | 52.1 | 48.3 | 52.3 | 50.1 | 46.8 |
| | % Basic | 27.3 | 27.4 | 26.1 | 24.8 | 27.8 | 27.4 | 26.0 |
| Charge variant | % Acidic | 31.9 | NR | 38.1 | 43.7 | NR | NR | 45.4 |

TABLE 13-continued

| | | | | | | | | |
|---|---|---|---|---|---|---|---|---|
| analysis by | % Main | 54.7 | NR | 48.6 | 44.3 | NR | NR | 42.1 |
| iCIEF | % Basic | 13.5 | NR | 13.3 | 12.0 | NR | NR | 12.5 |
| % Relative potency by bioassay | | 126 | NR | NR | 120 | NR | NR | 99 |

CEX, Cation exchange;
DS, Drug substance;
BMW, High molecular weight;
iCIEF, imaged capillary isoelectric-focusing,
LMW, Low molecular weight;
MFI, Microflow-imaging;
Monomer, intact antibody;
NR, Not required;
OD, Optical density;
RP, Reverse phase;
SE, Size exclusion;
UPLC, Ultra-performance liquid chromatography

TABLE 14

Research stability of 175 mg/mL formulation stored at accelerated and stress conditions

| Formulation | 175 mg/mL mAb1, 10 mM L-histidine, 5% (w/v) sucrose, 1.5% (w/v) L-proline, 0.2% (w/v) polysorbate 80, pH 6.0 |
|---|---|
| Fill Volume | 1.2 mL |
| Container/Closure | 3 mL Type 1 glass vials with a 13 mm FluroTec ® coated 4432/50 chlorobutyl stopper |

| | | 25° C./60%RH Storage (months) | | | | 40° C. Storage (days) | | |
|---|---|---|---|---|---|---|---|---|
| Assay | | 0 | 1 | 3 | 6 | 7 | 14 | 28 |
| Color and appearance | | Pass | Pass | Pass | Pass | Pass | Pass | Pass |
| Turbidity (Increase in OD at 405 nm) | | 0.00 | 0.00 | 0.00 | 0.00 | 0.00 | 0.00 | 0.01 |
| Turbidity (NTU by Nephelometry) | | 6.72 | 6.77 | 6.82 | 6.99 | 6.90 | 7.30 | 7.56 |
| pH | | 6.0 | 6.0 | 6.0 | 6.1 | 6.0 | 5.9 | 6.0 |
| Subvisible | ≥10 μm | 10 | NR | 28 | 58 | NR | NR | 97 |
| particulate | ≥25 μm | 0 | NR | 13 | 16 | NR | NR | 44 |
| analysis by HIAC (#/mL) | | | | | | | | |
| Subvisible | 2-10 μm | 144 | NR | 623 | 277 | NR | NR | 1131 |
| particulate | ≥10 μm | 22 | NR | 25 | 8 | NR | NR | 531 |
| analysis by MFI (#/mL) | ≥25 μm | 1 | NR | 3 | 2 | NR | NR | 3 |
| % Protein recovered by RP-UPLC | | 100 | 95 | 97 | 99 | 98 | 99 | 95 |
| Purity by MCE-SDS | Non-reduced; % main peak | 97.9 | NR | NR | 97.4 | NR | NR | 97.5 |
| | Reduced; % heavy + light | 100 | NR | NR | 99.7 | NR | NR | 99.4 |
| Purity by SE-UPLC | % HMW | 0.6 | 0.9 | 1.2 | 1.5 | 1.7 | 2.6 | 3.9 |
| | % Monomer | 99.1 | 98.6 | 98.5 | 98.0 | 97.7 | 96.8 | 95.5 |
| | % LMW | 0.4 | 0.5 | 0.3 | 0.6 | 0.6 | 0.7 | 0.6 |
| Charge variant analysis by CEX-UPLC | % Acidic | 18.7 | 18.9 | 21.3 | 26.2 | 19.7 | 22.0 | 23.9 |
| | % main | 53.6 | 54.4 | 52.3 | 48.3 | 51.7 | 50.1 | 49.4 |
| | % Basic | 27.8 | 26.7 | 26.4 | 25.5 | 28.6 | 27.9 | 26.7 |
| Charge variant analysis by iCIEF | % Acidic | 31.8 | NR | 37.0 | 45.0 | NR | NR | 47.3 |
| | % Main | 54.6 | NR | 50.3 | 43.3 | NR | NR | 39.2 |
| | % Basic | 13.6 | NR | 12.7 | 11.7 | NR | NR | 13.5 |
| % Relative potency by bioassay | | 102 | NR | NR | 123 | NR | NR | 86 |

CEX, Cation exchange;
DS, Drug substance;
BMW, High molecular weight;
iCIEF, imaged capillary isoelectric-focusing,
LMW, Low molecular weight;
MFI, Microflow-imaging;
Monomer, intact antibody;
NR, Not required;
OD, Optical density;
RP, Reverse phase;
SE, Size exclusion;
UPLC, Ultra-performance liquid chromatography Example 12: Stability of mAb1 Formulations Comprising Histidine Buffer, Sucrose and Polysorbate Tables 15-24 summarize the storage stability of exemplary mAb1 formulations that comprise 10 mM histidine buffer, at pH 6.0, sucrose and polysorbate.

TABLE 15

Research Stability of mAb1 formulation Stored at −80° C.

| | |
|---|---|
| Formulation | 72.2 mg/mL mAb1, 10 mM histidine, pH 6.0, 5% (w/v) sucrose |
| Fill Volume | 1.0 mL |
| Container/Closure | 5 mL polycarbonate vial with silicone lined polypropylene screw cap |

| Assay | | Length of Storage at −80° C. (months) | | | | | |
|---|---|---|---|---|---|---|---|
| | | 0 | 1 | 3 | 6 | 9 | 12 |
| Color and appearance | | Pass | Pass | Pass | Pass | Pass | Pass |
| Turbidity (Increase in OD at 405 nm) | | 0.00 | 0.00 | 0.00 | 0.00 | 0.00 | 0.00 |
| pH | | 6.2 | 6.3 | 6.2 | 6.1 | 6.2 | 6.1 |
| % Protein recovered by RP-UPLC | | 100 | 94 | 95 | 98 | 95 | 94 |
| Purity by MCE-SDS | Non-reduced; % Main peak | 99.5 | NR | NR | 99.5 | NR | 99.2 |
| | Reduced; % Heavy + light chain | 100 | NR | NR | 100 | NR | 99.8 |
| Purity by SE-UPLC | % HMW | 0.7 | 0.7 | 0.6 | 0.6 | 0.7 | 0.6 |
| | % Native | 98.7 | 98.8 | 98.9 | 98.7 | 98.9 | 98.8 |
| | % LMW | 0.6 | 0.6 | 0.5 | 0.6 | 0.4 | 0.6 |
| Charge variant analysis by CEX-UPLC | % Acidic | 22.2 | 22.2 | 22.6 | 23.2 | 24.1 | 23.5 |
| | % Main | 49.7 | 49.8 | 48.9 | 46.8 | 45.2 | 44.1 |
| | % Basic | 28.1 | 28.0 | 28.5 | 30.0 | 30.7 | 32.4 |
| Charge variant analysis by iCIEF | % Acidic | 38.9 | NR | NR | 39.1 | NR | 37.5 |
| | % Main | 56.5 | NR | NR | 56.2 | NR | 57.2 |
| | % Basic | 4.6 | NR | NR | 4.7 | NR | 5.3 |
| % Relative potency (Bioassay) | | 95 | NR | NR | 81 | NR | 120 |

CEX = Cation exchange;
HMW = High molecular weight;
iCIEF = Imaged capillary isoelectric focusing;
LMW = Low molecular weight;
MCE-SDS = Microchip capillary electrophoresis-sodium dodecyl sulfate;
MFI = Microflow imaging;
NR = Not required;
OD = Optical density;
RH = Relative humidity;
RP = Reverse phase;
SE = Size exclusion;
UPLC = Ultra-performance liquid chromatography

TABLE 16

Research Stability of mAb1 formulation Stored at −30° C.

| | |
|---|---|
| Formulation | 72.2 mg/mL mAb1, 10 mM histidine, pH 6.0, 5% (w/v) sucrose |
| Fill Volume | 1.0 mL |
| Container/Closure | 5 mL polycarbonate vial with silicone lined polypropylene screw cap |

| Assay | Length of Storage at −30° C. (months) | | | | | |
|---|---|---|---|---|---|---|
| | 0 | 1 | 3 | 6 | 9 | 12 |
| Color and appearance | Pass | Pass | Pass | Pass | Pass | Pass |
| Turbidity (Increase in OD at 405 nm) | 0.00 | 0.00 | 0.00 | 0.00 | 0.00 | 0.01 |
| pH | 6.2 | 6.3 | 6.2 | 6.1 | 6.2 | 6.1 |
| % Protein recovered by RP-UPLC | 100 | 93 | 95 | 100 | 96 | 96 |

TABLE 16-continued

| | | | | | | | |
|---|---|---|---|---|---|---|---|
| Purity by MCE-SDS | Non-reduced; % Main peak | 99.5 | NR | NR | 99.1 | NR | 99.2 |
| | Reduced; % Heavy + light chain | 100 | NR | NR | 100 | NR | 99.8 |
| Purity by SE-UPLC | % HMW | 0.7 | 0.7 | 0.6 | 0.7 | 0.7 | 0.6 |
| | % Native | 98.7 | 98.8 | 99.0 | 98.7 | 98.9 | 98.8 |
| | % LMW | 0.6 | 0.5 | 0.4 | 0.6 | 0.4 | 0.6 |
| Charge variant analysis by CEX-UPLC | % Acidic | 22.2 | 22.5 | 22.5 | 23.4 | 24.2 | 23.4 |
| | % Main | 49.7 | 49.6 | 48.9 | 46.6 | 45.6 | 44.1 |
| | % Basic | 28.1 | 28.0 | 28.6 | 30.0 | 30.2 | 32.5 |
| Charge variant analysis by iCIEF | % Acidic | 38.9 | NR | NR | 38.2 | NR | 37.8 |
| | % Main | 56.5 | NR | NR | 56.3 | NR | 56.6 |
| | % Basic | 4.6 | NR | NR | 5.5 | NR | 5.7 |

TABLE 17

Research Stability of mAb1 formulation Stored at −20° C.

| | |
|---|---|
| Formulation | 72.2 mg/mL mAb1, 10 mM histidine, pH 6.0, 5% (w/v) sucrose |
| Fill Volume | 1.0 mL |
| Container/Closure | 5 mL polycarbonate vial with silicone lined polypropylene screw cap |

| | | Length of Storage at −20° C. (months) | | | | | |
|---|---|---|---|---|---|---|---|
| Assay | | 0 | 1 | 3 | 6 | 9 | 12 |
| Color and appearance | | Pass | Pass | Pass | Pass | Pass | Pass |
| Turbidity (Increase in OD at 405 nm) | | 0.00 | 0.00 | 0.01 | 0.01 | 0.00 | 0.01 |
| pH | | 6.2 | 6.3 | 6.2 | 6.1 | 6.1 | 6.2 |
| % Protein recovered by RP-UPLC | | 100 | 95 | 97 | 101 | 98 | 98 |
| Purity by MCE-SDS | Non-reduced; % Main peak | 99.5 | NR | NR | 99.5 | NR | 99.3 |
| | Reduced; % Heavy + light chain | 100 | NR | NR | 100 | NR | 99.9 |
| Purity by SE-UPLC | % HMW | 0.7 | 0.7 | 0.7 | 0.7 | 0.8 | 0.7 |
| | % Native | 98.7 | 98.8 | 98.9 | 98.6 | 98.8 | 98.8 |
| | % LMW | 0.6 | 0.5 | 0.5 | 0.7 | 0.4 | 0.6 |
| Charge variant analysis by CEX-UPLC | % Acidic | 22.2 | 22.4 | 22.3 | 22.4 | 24.6 | 23.4 |
| | % Main | 49.7 | 49.7 | 49.2 | 47.6 | 45.5 | 44.2 |
| | % Basic | 28.1 | 27.9 | 28.5 | 30.0 | 30.0 | 32.5 |
| Charge variant analysis by iCIEF | % Acidic | 38.9 | NR | NR | 38.6 | NR | 38.6 |
| | % Main | 56.5 | NR | NR | 56.8 | NR | 56.2 |
| | % Basic | 4.6 | NR | NR | 4.6 | NR | 5.3 |
| % Relative potency (Bioassay) | | 95 | NR | NR | 96 | NR | 111 |

TABLE 18

Research Stability of mAb1 formulation-Effect of Accelerated Conditions

| | |
|---|---|
| Formulation | 72.2 mg/mL mAb1, 10 mM histidine, pH 6.0, 5% (w/v) sucrose |
| Fill Volume | 1.0 mL |
| Container/Closure | 5 mL polycarbonate vial with silicone lined polypropylene screw cap |

| | | 5° C. Storage (days) | | 25° C./60% RH Storage (days) | | 40° C./75% RH Storage (days) | |
|---|---|---|---|---|---|---|---|
| Assay | T = 0 | 28 | 56 | 14 | 28 | 14 | 28 |
| Color and appearance | Pass | Pass | Pass | Pass | Pass | Pass | Pass |
| Turbidity (Increase in OD at 405 nm) | 0.00 | 0.01 | 0.01 | 0.02 | 0.01 | 0.03 | 0.05 |
| pH | 6.2 | 6.2 | 6.1 | 6.2 | 6.2 | 6.2 | 6.1 |
| % Protein recovered by RP-UPLC | 100 | 96 | 100 | 97 | 100 | 105 | 113 |

TABLE 18-continued

| | | | | | | | | |
|---|---|---|---|---|---|---|---|---|
| Purity by MCE-SDS | Non-reduced; % Main peak | 99.5 | NR | 99.1 | NR | 99.5 | NR | 99.1 |
| | Reduced; % Heavy + light chain | 100 | NR | 100 | NR | 99.2 | NR | 98.7 |
| Purity by SE-UPLC | % HMW | 0.7 | 0.9 | 1.1 | 1.4 | 1.7 | 3.1 | 4.6 |
| | % Native | 98.7 | 98.5 | 98.4 | 98.0 | 97.7 | 96.1 | 94.6 |
| | % LMW | 0.6 | 0.6 | 0.6 | 0.7 | 0.7 | 0.8 | 0.9 |
| Charge variant analysis by CEX-UPLC | % Acidic | 22.2 | 22.2 | 22.3 | 22.0 | 22.6 | 25.6 | 30.8 |
| | % Main | 49.7 | 49.8 | 48.9 | 49.6 | 49.1 | 46.0 | 41.7 |
| | % Basic | 28.1 | 28.1 | 28.8 | 28.4 | 28.3 | 28.3 | 27.5 |
| Charge variant analysis by iCIEF | % Acidic | 38.9 | NR | 39.0 | NR | 41.1 | NR | 58.2 |
| | % Main | 56.5 | NR | 56.8 | NR | 53.8 | NR | 36.3 |
| | % Basic | 4.6 | NR | 4.2 | NR | 5.1 | NR | 5.5 |
| % Relative potency (Bioassay) | | 95 | NR | 95 | NR | 84 | NR | 87 |

TABLE 19

Research Stability of mAb1 Formulation Stored at −80° C.

| Formulation | 25 mg/mL mAb1, 10 mM histidine, pH 6.0, 10% (w/v) sucrose, 0.1% polysorbate 80 |
|---|---|
| Fill Volume | 1.0 mL |
| Container/Closure | 5 mL polycarbonate vial with silicone lined polypropylene screw cap |

| | | Length of Storage at −80° C. (months) | | | | | |
|---|---|---|---|---|---|---|---|
| Assay | | 0 | 1 | 3 | 6 | 9 | 12 |
| Color and appearance | | Pass | Pass | Pass | Pass | Pass | Pass |
| Turbidity (Increase in OD at 405 nm) | | 0.00 | 0.00 | 0.00 | 0.00 | 0.01 | 0.01 |
| pH | | 6.1 | 6.1 | 6.1 | 6.0 | 6.0 | 6.0 |
| % Protein recovered by RP-UPLC | | 100 | 100 | 97 | 95 | 100 | 99 |
| Purity by MCE-SDS | Non-reduced; % Main peak | 99.5 | NR | NR | 99.4 | NR | 99.5 |
| | Reduced; % Heavy + light chain | 100 | NR | NR | 100 | NR | 100 |
| Purity by SE-UPLC | % HMW | 0.8 | 0.8 | 0.8 | 0.8 | 0.8 | 0.8 |
| | % Native | 98.6 | 98.7 | 98.6 | 98.6 | 98.8 | 98.7 |
| | % LMW | 0.6 | 0.5 | 0.6 | 0.6 | 0.5 | 0.5 |
| Charge variant analysis by CEX-UPLC | % Acidic | 22.8 | 23.0 | 23.3 | 23.5 | 23.9 | 25.4 |
| | % Main | 47.3 | 47.3 | 46.2 | 45.3 | 44.2 | 44.2 |
| | % Basic | 30.0 | 29.8 | 30.6 | 31.2 | 31.9 | 30.4 |
| Charge variant analysis by iCIEF | % Acidic | 40.1 | NR | NR | 38.1 | NR | 41.3 |
| | % Main | 56.1 | NR | NR | 57.4 | NR | 54.1 |
| | % Basic | 3.8 | NR | NR | 4.6 | NR | 4.6 |
| % Relative potency (Bioassay) | | 112 | NR | NR | 130 | NR | 107 |

TABLE 20

Research Stability of mAb1 Formulation Stored at −30° C.

| Formulation | 25 mg/mL mAb1, 10 mM histidine, pH 6.0, 10% (w/v) sucrose, 0.1% polysorbate 80 |
|---|---|
| Fill Volume | 1.0 mL |
| Container/Closure | 5 mL polycarbonate vial with silicone lined polypropylene screw cap |

TABLE 20-continued

Research Stability of mAb1 Formulation Stored at −30° C.

| Assay | | Length of Storage at −30° C. (months) | | | | | |
|---|---|---|---|---|---|---|---|
| | | 0 | 1 | 3 | 6 | 9 | 12 |
| Color and appearance | | Pass | Pass | Pass | Pass | Pass | Pass |
| Turbidity (Increase in OD at 405 nm) | | 0.00 | 0.00 | 0.00 | 0.00 | 0.01 | 0.01 |
| pH | | 6.1 | 6.1 | 6.1 | 6.0 | 6.1 | 6.0 |
| % Protein recovered by RP-UPLC | | 100 | 100 | 102 | 97 | 100 | 102 |
| Purity by MCE-SDS | Non-reduced; % Main peak | 99.5 | NR | NR | 99.1 | NR | 99.5 |
| | Reduced; % Heavy + light chain | 100 | NR | NR | 100 | NR | 100 |
| Purity by SE-UPLC | % HMW | 0.8 | 0.8 | 0.8 | 0.8 | 0.8 | 0.8 |
| | % Native | 98.6 | 98.7 | 98.6 | 98.7 | 98.8 | 98.7 |
| | % LMW | 0.6 | 0.5 | 0.6 | 0.6 | 0.4 | 0.6 |
| Charge variant analysis by CEX-UPLC | % Acidic | 22.8 | 23.1 | 22.9 | 23.5 | 23.7 | 25.1 |
| | % Main | 47.3 | 47.1 | 46.5 | 45.3 | 44.4 | 44.4 |
| | % Basic | 30.0 | 29.8 | 30.6 | 31.2 | 31.9 | 30.5 |
| Charge variant analysis by iCIEF | % Acidic | 40.1 | NR | NR | 38.0 | NR | 41.3 |
| | % Main | 56.1 | NR | NR | 57.3 | NR | 53.3 |
| | % Basic | 3.8 | NR | NR | 4.7 | NR | 5.4 |

TABLE 21

Research Stability of mAb1 Formulation Stored at −20° C.

| Formulation | 25 mg/mL mAb1, 10 mM histidine, pH 6.0, 10% (w/v) sucrose, 0.1% polysorbate 80 |
|---|---|
| Fill Volume | 1.0 mL |
| Container/Closure | 5 mL polycarbonate vial with silicone lined polypropylene screw cap |

| Assay | | Length of Storage at −20° C. (months) | | | | | |
|---|---|---|---|---|---|---|---|
| | | 0 | 1 | 3 | 6 | 9 | 12 |
| Color and appearance | | Pass | Pass | Pass | Pass | Pass | Pass |
| Turbidity (Increase in OD at 405 nm) | | 0.00 | 0.00 | 0.00 | 0.00 | 0.01 | 0.00 |
| pH | | 6.1 | 6.1 | 6.1 | 6.0 | 6.1 | 6.0 |
| % Protein recovered by RP-UPLC | | 100 | 99 | 102 | 97 | 106 | 102 |
| Purity by MCE-SDS | Non-reduced; % Main peak | 99.5 | NR | NR | 99.4 | NR | 99.4 |
| | Reduced; % Heavy + light chain | 100 | NR | NR | 100 | NR | 99.0 |
| Purity by SE-UPLC | % HMW | 0.8 | 0.8 | 0.8 | 0.8 | 0.7 | 0.8 |
| | % Native | 98.6 | 98.7 | 98.6 | 98.7 | 98.8 | 98.7 |
| | % LMW | 0.6 | 0.5 | 0.6 | 0.6 | 0.4 | 0.6 |
| Charge variant analysis by CEX-UPLC | % Acidic | 22.8 | 22.9 | 23.5 | 23.6 | 24.3 | 25.2 |
| | % Main | 47.3 | 47.3 | 46.0 | 45.2 | 43.8 | 43.9 |
| | % Basic | 30.0 | 29.8 | 30.6 | 31.2 | 31.9 | 30.8 |
| Charge variant analysis by iCIEF | % Acidic | 40.1 | NR | NR | 38.4 | NR | 41.6 |
| | % Main | 56.1 | NR | NR | 57.9 | NR | 53.3 |
| | % Basic | 3.8 | NR | NR | 3.7 | NR | 5.1 |
| % Relative potency (Bioassay) | | 112 | NR | NR | 120 | NR | 131 |

TABLE 22

Research Stability of mAb1 Formulation - Effect of Accelerated Conditions

| Formulation | 25 mg/mL mAb1, 10 mM histidine, pH 6.0, 10% (w/v) sucrose, 0.1% polysorbate 80 |
|---|---|
| Fill Volume | 1.0 mL |
| Container/Closure | 5 mL polycarbonate vial with silicone lined polypropylene screw cap |

TABLE 22-continued

Research Stability of mAb1 Formulation - Effect of Accelerated Conditions

| Assay | | No Storage T = 0 | 5° C. Storage (days) 28 | 5° C. Storage (days) 56 | 25° C./60% RH Storage (days) 14 | 25° C./60% RH Storage (days) 28 | 40° C./75% RH Storage (days) 14 | 40° C./75% RH Storage (days) 28 |
|---|---|---|---|---|---|---|---|---|
| Color and appearance | | Pass | Pass | Pass | Pass | Pass | Pass | Pass |
| Turbidity (Increase in OD at 405 nm) | | 0.00 | 0.00 | 0.00 | 0.00 | 0.00 | 0.01 | 0.03 |
| pH | | 6.1 | 6.1 | 6.0 | 6.1 | 6.1 | 6.0 | 6.0 |
| % Protein recovered by RP-UPLC | | 100 | 101 | 102 | 106 | 107 | 113 | 114 |
| Purity by MCE-SDS | Non-reduced; % Main peak | 99.5 | NR | 99.1 | NR | 99.5 | NR | 99.3 |
| | Reduced; % Heavy + light chain | 100 | NR | 100 | NR | 100 | NR | 99.1 |
| Purity by SE-UPLC | % HMW | 0.8 | 0.7 | 0.7 | 0.9 | 0.9 | 3.4 | 5.0 |
| | % Native | 98.6 | 98.8 | 98.7 | 98.6 | 98.6 | 95.7 | 93.7 |
| | % LMW | 0.6 | 0.5 | 0.6 | 0.5 | 0.6 | 0.9 | 1.3 |
| Charge variant analysis by CEX-UPLC | % Acidic | 22.8 | 22.8 | 23.3 | 22.6 | 22.8 | 29.6 | 32.5 |
| | % Main | 47.3 | 47.3 | 46.1 | 47.2 | 47.0 | 39.5 | 36.4 |
| | % Basic | 30.0 | 29.9 | 30.6 | 30.2 | 30.2 | 30.9 | 31.1 |
| Charge variant analysis by iCIEF | % Acidic | 40.1 | NR | 39.8 | NR | 40.2 | NR | 53.7 |
| | % Main | 56.1 | NR | 57.0 | NR | 55.9 | NR | 42.2 |
| | % Basic | 3.8 | NR | 3.2 | NR | 3.9 | NR | 4.0 |
| % Relative potency (Bioassay) | | 112 | NR | 103 | NR | 91 | NR | 79 |

TABLE 23

Research Stability of mAb1 formulation Stored at 5° C.

| Formulation | 25 mg/mL mAb1, 10 mM histidine, 10% (w/v) sucrose, 0.1% (w/v) polysorbate 80, pH 6.0 |
|---|---|
| Fill Volume | 1.0 mL |
| Container/Closure | 2 mL Type 1 borosilicate glass vials with a 13 mm FluroTec ® coated West S2-451 4432/50 GRY B2-40 stoppers |

| Assay | | Length of Storage at 5° C. (months) 0 | 1 | 3 | 6 | 9 | 12 |
|---|---|---|---|---|---|---|---|
| Color and appearance | | Pass | Pass | Pass | Pass | Pass | Pass |
| Turbidity (Increase in OD at 405 nm) | | 0.00 | 0.00 | 0.00 | 0.01 | 0.01 | 0.00 |
| pH | | 6.2 | 6.1 | 6.1 | 6.1 | 6.0 | 6.1 |
| Particulate analysis by MFI (particles/mL) | 2 to 10 μm | 823 | NR | NR | 2169 | NR | 29331 |
| | ≥10 μm | 15 | NR | NR | 10 | NR | 56 |
| | ≥25 μm | 0 | NR | NR | 3 | NR | 5 |
| % Protein recovered by RP-UPLC | | 100 | 100 | 98 | 101 | 102 | 90 |
| Purity by MCE-SDS | Non-reduced; % main peak | 99.4 | NR | NR | 99.5 | NR | 99.2 |
| | Reduced; % heavy + light chain | 100 | NR | NR | 100 | NR | 100 |
| Purity by SE-UPLC | % HMW | 0.7 | 0.7 | 0.7 | 0.8 | 0.9 | 0.9 |
| | % Native | 98.7 | 98.8 | 98.7 | 98.6 | 98.6 | 98.5 |
| | % LMW | 0.6 | 0.5 | 0.6 | 0.6 | 0.5 | 0.6 |
| Charge variant analysis by CEX-UPLC | % Acidic | 23.0 | 22.8 | 23.5 | 22.4 | 24.1 | 22.4 |
| | % Main | 48.5 | 48.6 | 46.2 | 47.2 | 44.4 | 45.5 |
| | % Basic | 28.6 | 28.6 | 30.4 | 30.4 | 31.5 | 32.1 |
| Charge variant analysis by iCIEF | % Acidic | 39.8 | NR | NR | 39.2 | NR | 40.1 |
| | % Main | 56.7 | NR | NR | 56.5 | NR | 55.7 |
| | % Basic | 3.4 | NR | NR | 4.3 | NR | 4.1 |
| % Relative potency (bioassay) | | 111 | NR | NR | 132 | NR | 124 |

TABLE 24

Research Stability of mAb1 formulation Stored at Accelerated Conditions

| | |
|---|---|
| Formulation | 25 mg/mL mAb1, 10 mM histidine, 10% (w/v) sucrose, 0.1% (w/v) polysorbate 80, pH 6.0 |
| Fill Volume | 1.0 mL |
| Container/Closure | 2 mL Type 1 borosilicate glass vials with a 13 mm FluroTec ® coated West S2-451 4432/50 GRY B2-40 stoppers |

| Assay | | | 25° C./60% RH Storage (months) | | | 45° C. Storage (days) | | |
|---|---|---|---|---|---|---|---|---|
| | | 0 | 0.5 | 1 | 3 | 7 | 14 | 28 |
| Color and appearance | | Pass | Pass | Pass | Pass | Pass | Pass | Pass |
| Turbidity (Increase in OD at 405 nm) | | 0.00 | 0.01 | 0.01 | 0.00 | 0.01 | 0.00 | 0.02 |
| pH | | 6.2 | 6.1 | 6.1 | 6.1 | 6.2 | 6.1 | 6.1 |
| Particulate | 2 to 10 μm | 823 | NR | NR | 1056 | NR | NR | 521 |
| analysis by MFI | ≥10 μm | 15 | NR | NR | 23 | NR | NR | 83 |
| (particles/mL) | ≥25 μm | 0 | NR | NR | 3 | NR | NR | 4 |
| % Protein recovered by RP-UPLC | | 100 | 99 | 100 | 99 | 99 | 100 | 99 |
| Purity by MCE-SDS | Non-reduced; % main peak | 99.4 | NR | NR | 99.4 | NR | NR | 99.2 |
| | Reduced; % heavy + light chain | 100 | NR | NR | 100 | NR | NR | 98.6 |
| Purity by SE-UPLC | % HMW | 0.7 | 0.8 | 0.9 | 1.1 | 1.6 | 3.2 | 8.5 |
| | % Native | 98.7 | 98.6 | 98.5 | 98.1 | 97.6 | 95.9 | 89.7 |
| | % LMW | 0.6 | 0.6 | 0.6 | 0.8 | 0.8 | 1.0 | 1.8 |
| Charge variant analysis by CEX-UPLC | % Acidic | 23.0 | 22.6 | 23.1 | 25.8 | 24.7 | 27.3 | 34.0 |
| | % Main | 48.5 | 48.7 | 48.1 | 44.5 | 46.2 | 44.1 | 35.9 |
| | % Basic | 28.6 | 28.8 | 28.9 | 29.8 | 29.1 | 28.6 | 30.2 |
| Charge variant analysis by iCIEF | % Acidic | 39.8 | NR | NR | 47.1 | NR | NR | 66.9 |
| | % Main | 56.7 | NR | NR | 49.5 | NR | NR | 30.2 |
| | % Basic | 3.4 | NR | NR | 3.5 | NR | NR | 3.0 |
| % Relative potency by bioassay | | 111 | NR | NR | 94 | NR | NR | 63 |

Tables 25-27 summarize the stress stability of exemplary formulations.

TABLE 25

Research Stability of mAb1 formulation - Effect of Stress Conditions

| | |
|---|---|
| Formulation | 72.2 mg/mL mAb1, 10 mM histidine, pH 6.0, 5% (w/v) sucrose |
| Fill Volume | 1.0 mL |
| Container/Closure | 5 mL polycarbonate vial with silicone lined polypropylene screw cap |

| Assay | | T = 0 | Agitation (min) | | Freeze/Thaw (cycles) | |
|---|---|---|---|---|---|---|
| | | | 10 | 15 | 4 | 8 |
| Color and appearance | | Pass | Pass | Pass | Pass | Pass |
| Turbidity (Increase in OD at 405 nm) | | 0.00 | 0.00 | 0.09 | 0.01 | 0.00 |
| pH | | 6.2 | 6.2 | 6.2 | 6.3 | 6.3 |
| % Protein Recovered by RP-UPLC | | 100 | 100 | 99 | 95 | 95 |
| Purity by MCE-SDS | Non-reduced; % Main peak | 99.5 | NR | 99.2 | NR | 99.4 |
| | Reduced; % Heavy + light chain | 100 | NR | 100 | NR | 100 |
| Purity by SE-UPLC | % HMW | 0.7 | 0.8 | 4.6 | 0.6 | 0.7 |
| | % Native | 98.7 | 98.7 | 94.9 | 98.9 | 98.8 |
| | % LMW | 0.6 | 0.5 | 0.5 | 0.5 | 0.5 |
| Charge variant analysis by CEX-UPLC | % Acidic | 22.2 | 22.2 | 21.9 | 22.0 | 22.2 |
| | % Main | 49.7 | 49.6 | 49.9 | 49.7 | 49.6 |
| | % Basic | 28.1 | 28.2 | 28.2 | 28.3 | 28.2 |

TABLE 25-continued

Research Stability of mAb1 formulation - Effect of Stress Conditions

| Charge variant analysis by iCIEF | % Acidic | 38.9 | NR | 40.8 | NR | 39.0 |
|---|---|---|---|---|---|---|
| | % Main | 56.5 | NR | 54.7 | NR | 56.5 |
| | % Basic | 4.6 | NR | 4.6 | NR | 4.5 |
| % Relative Potency (Bioassay) | | 95 | NR | 87 | NR | 89 |

TABLE 26

Research Stability of mAb1 Formulation - Effect of Stress Conditions

| | |
|---|---|
| Formulation | 25 mg/mL mAb1, 10 mM histidine, pH 6.0, 10% (w/v) sucrose, 0.1% (w/v) polysorbate 80 |
| Fill Volume | 1.0 mL |
| Container/Closure | 5 mL polycarbonate vial with silicone lined polypropylene screw cap |

| Assay | | No Stress T = 0 | Agitation (minutes) 60 | Agitation (minutes) 120 | Freeze/Thaw (cycles) 4 | Freeze/Thaw (cycles) 8 |
|---|---|---|---|---|---|---|
| Color and appearance | | Pass | Pass | Pass | Pass | Pass |
| Turbidity (Increase in OD at 405 nm) | | 0.00 | 0.00 | 0.00 | 0.00 | 0.00 |
| pH | | 6.1 | 6.1 | 6.1 | 6.1 | 6.1 |
| % Protein recovered by RP-UPLC | | 100 | 101 | 100 | 99 | 100 |
| Purity by MCE-SDS | Non-reduced; % Main peak | 99.5 | NR | 99.5 | NR | 99.6 |
| | Reduced; % Heavy + light chain | 100 | NR | 100 | NR | 100 |
| Purity by SE-UPLC | % HMW | 0.8 | 0.8 | 0.7 | 0.8 | 0.8 |
| | % Native | 98.6 | 98.7 | 98.7 | 98.7 | 98.6 |
| | % LMW | 0.6 | 0.6 | 0.6 | 0.5 | 0.6 |
| Charge variant analysis by CEX-UPLC | % Acidic | 22.8 | 22.8 | 22.8 | 22.9 | 22.7 |
| | % Main | 47.3 | 47.2 | 47.3 | 47.1 | 47.2 |
| | % Basic | 30.0 | 30.0 | 29.2 | 30.1 | 30.1 |
| Charge variant analysis by iCIEF | % Acidic | 40.1 | NR | 39.6 | NR | 40.0 |
| | % Main | 56.1 | NR | 56.9 | NR | 56.3 |
| | % Basic | 3.8 | NR | 3.5 | NR | 3.6 |
| % Relative potency (Bioassay) | | 112 | NR | 106 | NR | 137 |

TABLE 27

Research Stability of mAb1 formulation - Effect of Stress Conditions

| | |
|---|---|
| Formulation | 25 mg/mL mAb1, 10 mM histidine, 10% (w/v) sucrose, 0.1% (w/v) polysorbate 80, pH 6.0 |
| Fill Volume | 1.0 mL |
| Container/Closure | 2 mL Type 1 borosilicate glass vials with a 13 mm FluroTec ® coated West S2-451 4432/50 GRY B2-40 stoppers |

| Assay | | 0 | Agitation (min) 60 | Agitation (min) 120 | Freeze/Thaw (cycles) 4 | Freeze/Thaw (cycles) 8 |
|---|---|---|---|---|---|---|
| Color and appearance | | Pass | Pass | Pass | Pass | Pass |
| Turbidity (Increase in OD at 405 nm) | | 0.00 | 0.00 | 0.00 | 0.00 | 0.00 |
| pH | | 6.2 | 6.2 | 6.2 | 6.2 | 6.2 |
| Particulate analysis by MFI (particles/mL) | 2 to 10 μm | 823 | NR | 1170 | NR | 1404 |
| | ≥10 μm | 15 | NR | 38 | NR | 67 |
| | ≥25 μm | 0 | NR | 0 | NR | 2 |
| % Protein recovered by RP-UPLC | | 100 | 100 | 101 | 101 | 101 |

TABLE 27-continued

Research Stability of mAb1 formulation - Effect of Stress Conditions

| | | | | | | |
|---|---|---|---|---|---|---|
| Purity by MCE-SDS | Non-reduced; % main peak | 99.4 | NR | 99.4 | NR | 99.3 |
| | Reduced; % heavy + light chain | 100 | NR | 100 | NR | 100 |
| Purity by SE-UPLC | % HMW | 0.7 | 0.6 | 0.7 | 0.7 | 0.7 |
| | % Native | 98.7 | 98.8 | 98.7 | 98.7 | 98.6 |
| | % LMW | 0.6 | 0.6 | 0.6 | 0.6 | 0.7 |
| Charge variant analysis by CEX-UPLC | % Acidic | 23.0 | 22.9 | 22.8 | 22.8 | 22.7 |
| | % Main | 48.5 | 48.3 | 48.4 | 48.4 | 48.5 |
| | % Basic | 28.6 | 28.8 | 28.8 | 28.8 | 28.8 |
| Charge variant analysis by iCIEF | % Acidic | 39.8 | NR | 39.6 | NR | 39.6 |
| | % Main | 56.7 | NR | 56.9 | NR | 56.9 |
| | % Basic | 3.4 | NR | 3.4 | NR | 3.6 |
| % Relative potency by bioassay | | 111 | NR | 90 | NR | 129 |

TABLE 28

Accelerated and Stress Stability of 50 mg/mL and 25 mg/mL of mAb1 Formulations

| Formulation | | 50 mg/mL mAb1, 10 mM histidine, 10% (w/v) sucrose, 0.1% (w/v) polysorbate 80, pH 6.0 | | | 25 mg/mL mAb1, 10 mM histidine, 10% (w/v) sucrose, 0.1% (w/v) polysorbate 80, pH 6.0 | | |
|---|---|---|---|---|---|---|---|
| Fill Volume | | 1.0 mL | | | 1.0 mL | | |
| Container/Closure | | 2 mL Type 1 borosilicate glass vials with a 13 mm FluroTec ® coated West S2-451 4432/50 GRY B2-40 stoppers | | | 2 mL Type 1 borosilicate glass vials with a 13 mm FluroTec ® coated West S2-451 4432/50 GRY B2-40 stoppers | | |
| Assay | | T = 0 | 25° C./60% RH 1 month | 45° C. 28 days | T = 0 | 25° C./60% RH 1 month | 45° C. 28 days |
| Color and appearance | | Pass | Pass | Pass | Pass | Pass | Pass |
| Turbidity (Increase in OD at 405 nm) | | 0.00 | 0.01 | 0.02 | 0.00 | 0.01 | 0.02 |
| pH | | 6.0 | 6.0 | 6.1 | 6.2 | 6.1 | 6.1 |
| % Protein recovered by RP-UPLC | | 100 | 103 | 113 | 100 | 100 | 99 |
| Purity by SE-UPLC | % HMW | 1.9 | 4.0 | 10.8 | 0.7 | 0.9 | 8.5 |
| | % Monomer | 97.5 | 95.2 | 88.0 | 98.7 | 98.5 | 89.7 |
| | % LMW | 0.6 | 0.8 | 1.2 | 0.6 | 0.6 | 1.8 |
| Charge variant analysis by CEX-UPLC | % Acidic | 24.6 | 29.0 | 37.1 | 23.0 | 23.1 | 34.0 |
| | % Main | 49.9 | 42.5 | 33.2 | 48.5 | 48.1 | 35.9 |
| | % Basic | 25.6 | 28.5 | 29.7 | 28.6 | 28.9 | 30.2 |

Example 13: Proven Acceptable Range (PAR) Study

During the manufacture of mAb1 drug product (DP), variations in the composition of the DP may occur. These variations may include the concentration of the active ingredient, the concentration of the excipients, and/or the pH of the formulation. Because changes in any of these parameters could potentially impact the stability or potency of the drug product, proven acceptable range (PAR) studies were conducted to assess whether variations in the DP composition, within the defined ranges, would impact the stability or potency of mAb1 DP.

Two Design-Of-Experiment (DOE) studies were used to evaluate the effect of each formulation parameter as well as the interactions on the formulation stability:

A fractional factorial design Pre-PAR study with accelerated and stress stability assessment to identify critical formulation parameters that may impact mAb1 DP stability;

A full factorial design PAR study including critical formulation parameters identified from the Pre-PAR study, with long-term shelf-life stability to demonstrate the acceptable ranges of the formulation parameters.

Pre-PAR Study Design

To assess critical and/or interacting formulation parameters in the DP composition that might be important to product quality, a fractional factorial DOE was applied to examine the accelerated and stress stability of formulations by varying all formulation parameters, including protein concentration (±10%), buffer and stabilizer concentrations (±20%), surfactant concentration (±50%), and pH (±0.3 unit). The tested formulation parameter ranges were defined to be equal or wider than the specification acceptance criteria and manufacturing experience. The study was designed with a statistical software using a $2^{(6-2)}$ resolution IV fractional factorial experiment. Together with four target formulations as the center points, the study included 20 runs, as shown in Table 29.

TABLE 29

Formulations tested in the Pre-PAR study

| Formulation | [mAb1] mg/mL | [histidine] mM | % sucrose (w/v) | % L-proline (w/v) | % polysorbate 80 (w/v) | pH |
|---|---|---|---|---|---|---|
| 1 | 45 | 12 | 4 | 1.2 | 0.3 | 6.3 |
| 2 | 45 | 12 | 4 | 1.8 | 0.3 | 5.7 |
| 3 | 45 | 8 | 6 | 1.8 | 0.3 | 6.3 |
| 4 | 50 | 10 | 5 | 1.5 | 0.2 | 6.0 |
| 5 | 45 | 8 | 4 | 1.8 | 0.1 | 6.3 |
| 6 | 55 | 8 | 6 | 1.2 | 0.1 | 6.3 |
| 7 | 55 | 8 | 4 | 1.2 | 0.3 | 6.3 |
| 8 | 50 | 10 | 5 | 1.5 | 0.2 | 6.0 |
| 9 | 55 | 12 | 6 | 1.8 | 0.3 | 6.3 |
| 10 | 45 | 12 | 6 | 1.2 | 0.1 | 6.3 |
| 11 | 55 | 8 | 4 | 1.8 | 0.3 | 5.7 |
| 12 | 55 | 8 | 6 | 1.8 | 0.1 | 5.7 |
| 13 | 45 | 12 | 6 | 1.8 | 0.1 | 5.7 |
| 14 | 55 | 12 | 6 | 1.2 | 0.3 | 5.7 |
| 15 | 50 | 10 | 5 | 1.5 | 0.2 | 6.0 |
| 16 | 45 | 8 | 6 | 1.2 | 0.3 | 5.7 |
| 17 | 55 | 12 | 4 | 1.8 | 0.1 | 6.3 |
| 18 | 45 | 8 | 4 | 1.2 | 0.1 | 5.7 |
| 19 | 50 | 10 | 5 | 1.5 | 0.2 | 6.0 |
| 20 | 55 | 12 | 4 | 1.2 | 0.1 | 5.7 |

All 20 formulations at the accelerated conditions and the stress conditions (25° C., 37° C., freeze/thaw [F/T] and agitation) were characterized and assessed for physical/chemical properties and stability, including visual inspection, pH, turbidity, osmolality, conductivity, purity, protein concentration and recovery, charge variant analysis, and sub-visible particulate analysis.

Pre-PAR Study Results

All 20 formulations showed no change after agitation or F/T stress. Results from 25° C. and 37° C. incubation were analyzed by a regression model (JMP fit model with standard least square personality and effect leverage emphasis). Statistical analysis of the main and interacting variables of all experimental formulations against the critical quality attributes revealed that pH, protein concentration and sucrose concentration were important to product quality. The two product quality attributes impacted were HMW species and acidic charge variants. Other formulation parameters, including histidine, proline or polysorbate 80 concentrations within the ranges tested, were found to have no statistically significant impact on the product quality. Under accelerated conditions, there was no secondary or higher interactions that impact formulation stability. The pre-PAR study results indicated that pH, mAb1 concentration, and sucrose concentration were critical to the mAb1 formulation stability, and were considered as the critical formulation parameters for the 50 mg/mL mAb1 formulation.

Although pH, mAb1 concentration and sucrose concentration were identified as the critical formulation parameters, the impact of these three factors on the quality attributes was minimal. Based on the statistical analysis, the change in pH range of 5.7-6.3, 45-55 mg/mL of mAb1, and/or 4-6% of sucrose likely had <15% impact on the formation of HMW species and acidic charge variants.

To confirm the impact on the long-term storage stability at the recommended DP storage condition, the following three critical formulation parameters: pH, mAb1 concentration, and sucrose concentration, were further evaluated in a PAR study with long-term storage stability.

PAR Study Design

A full factorial DOE design was applied to examine the long-term shelf-life storage stability of formulations with varying pH (±0.3 unit), protein concentration (±10%), and sucrose concentration (±20%), resulting in eight experimental runs (Table 30); a reference formulation (formulation 3, the target formulation in Table 30) was included as the center point formulation.

TABLE 30

Formulations tested in PAR studies

| Formulation | [mAb1] mg/mL | [histidine] mM | % sucrose (w/v) | % L-proline (w/v) | % polysorbate 80 (w/v) | pH |
|---|---|---|---|---|---|---|
| 1 | 55 | 10 | 6 | 1.5 | 0.2 | 5.7 |
| 2 | 45 | 10 | 6 | 1.5 | 0.2 | 5.7 |
| 3 | 50 | 10 | 5 | 1.5 | 0.2 | 6.0 |
| 4 | 55 | 10 | 6 | 1.5 | 0.2 | 6.3 |
| 5 | 55 | 10 | 4 | 1.5 | 0.2 | 6.3 |
| 6 | 55 | 10 | 4 | 1.5 | 0.2 | 5.7 |
| 7 | 45 | 10 | 4 | 1.5 | 0.2 | 6.3 |
| 8 | 45 | 10 | 4 | 1.5 | 0.2 | 5.7 |
| 9 | 45 | 10 | 6 | 1.5 | 0.2 | 6.3 |

The full factorial study design allows the estimation of all main effect terms as well as the interaction terms. The tested formulation parameter ranges, defined to be equal or wider than the specification acceptance criteria and manufacturing experience, remained the same as in the Pre-PAR study.

The stability of the experimental formulations was compared to the stability of a reference formulation at pH 6.0 containing all formulation components at their nominal concentrations (F3). PAR studies utilized a mAb1 DS lot manufactured with the representative commercial manufacturing process. DP formulations were filled into 10 mL Schott type 1 borosilicate glass vials, with 20 mm Fluro-Tec®-coated West S2-451 4432/50 GRY B2-40 stoppers (commercial DP representation) and assessed for long-term storage stability at 2-8° C. The formulations were studied according to the analysis plan in Table 31.

TABLE 31

Analysis plan for PAR study

| Test | Samples Analyzed | Quality Attributes |
|---|---|---|
| Appearance | All | Color, visible particulates |
| Turbidity (Increase in OD at 405 nm) | All | Color, particulates, clarity |
| Turbidity by Nephelometry | t = 0, 6, 12, 18, 24, and 36 months at 5° C. | Clarity (Solution Precipitation, Particulates, Opalescence) |
| pH | All | pH |
| Total protein content by RP-UPLC | t = 0 | Protein concentration |
| Osmolality | t = 0 | Solute concentration |
| Conductivity | t = 0 | Conductive property |
| Purity by SE-UPLC | All | Molecule weight variants: % HMW, % Monomer, % LWM |
| Charge Variant Analysis by cIEF | t = 0, 6, 12, 18, 24, and 36 months at 5° C. | Charge isoforms: % Acidic, % Main, % Basic |

TABLE 31-continued

Analysis plan for PAR study

| Test | Samples Analyzed | Quality Attributes |
| --- | --- | --- |
| Particulate Matter (Light Obscuration) | t = 0, 6, 12, 18, 24, and 36 months at 5° C. | Subvisible particulates. Acceptance criteria set forth in USP <788> (<6000 particles/container for particles ≥10 μm and <600 particles/container for particles ≥25 μm) |
| Particulate Matter (MicroFlow Imaging, MFI) | t = 0, 6, 12, 18, 24, and 36 months at 5° C. | Subvisible particulates (For information only) |
| Bioassay | t = 0, 6, 12, 18, 24, and 36 months at 5° C. | Potency Acceptance criteria: 50-150% of reference standard |

PAR Study Results

Effect on the HMW Species Formation

There was no meaningful increase in the % HMW as measured by SE-UPLC up to 12 months at 2-8° C. for all 9 formulations. All values were well below the upper specification, and no significant increase in % HMW over time was observed.

The HMW species formation for 50 mg/mL mAb1 DP at 2-8° C. was found to be extremely slow. For up to 12 months, the maximum change of relative amount in % HMW in the 9 formulation was ~0.2%. Since the change in % HMW was minimal, and monomer concentration could be considered as a constant, the aggregation from monomers to HMW species could be simplified as a zero order reaction. Therefore a simplified linear model was used to analyze the % HMW stability data. By linearly fitting the % HMW over time, the HMW species formation rate was derived for each formulation.

The rate was analyzed against the main factors as well as all interaction terms using a regression model (JMP fit model with standard least square personality and effect leverage emphasis). The resulted regression model was statistically significant with an $R^2$ of 0.74. mAb1 concentration, pH, and time were statistically significant, but the effect on the % HMW species formation was statistically insignificant, only contributing up to 0.1%.

Therefore, these factors, pH at 5.7-6.3, mAb1 concentration at 45-55 mg/mL, and sucrose concentration at 4-6%, had no practical relevance to the % HMW stability at 2-8° C.

% HMW in all 9 formulations up to 12-month time-point were well below the defined acceptance criteria limit of 4% and thus within the release and end of shelf-life specifications. In addition, the linear models predicted that after 24 months of shelf-life storage at 2° C.-8° C., the % HMW, ranging from 0.6% to 0.8%, would also be well below the specification limit.

Based on the long-term storage stability data, the variations of the critical formulation parameters within the studied ranges were found to have no significant impact on the mAb1 formulation stability. The 50 mg/mL mAb1 formulation was robust with regards to HMW species formation within the tested formulation composition range.

Effect on the Acidic Charge Variants Formation

There was no meaningful increase in the % acidic charge variants measured up to 12 months at 2-8° C. for all 9 formulations. All values were below upper specification, and no significant increase in % acidic charge variants over time was observed.

The mAb1 formulation was considered to be robust with regard to acidic charge variants formation within the tested formulation composition range.

Effect on General Quality Attributes

The effect of pH, mAb1 concentration, and sucrose, as well as storage time on other DP general quality attributes, including appearance, pH, turbidity, subvisible particulates, protein recovery, % monomer and % LMW by SEC, % main and % basic charge variants by iCIEF, and bioactivity were studied. All values were within specification, and no meaningful change over time or difference between the PAR formulations was observed:

No precipitate or visible particulate was detected by either visual inspection or turbidity measurements (OD at 405 nm and nephelometry);

No statistically significant changes in protein recovery were observed (RP-UPLC);

The pH of the formulations was stable;

No meaningful increases in subvisible particulates, and no meaningful differences were observed in the subvisible particulate counts between PAR study formulations.

For subvisible particulates measured by HIAC, all values were below the acceptable limits set by USP <788>, and no meaningful variation in subvisible particles between formulations was observed.

In additions, the subvisible particles were also measured by MFI. No meaningful variation in subvisible particles between formulations was observed.

The bioassay results were within the specification limit for all formulations during storage.

The results demonstrate that variations of the critical formulation parameters (pH, mAb1 concentration, and sucrose concentration) within the studied ranges have no significant impact on the mAb1 formulation stability. The 50 mg/mL mAb1 formulation is robust with regards to general quality attributes within the tested formulation composition range.

Effect of Freezing and Thawing on the Stability of PAR Formulations

The physical and chemical stability of 50 mg/mL mAb1 formulation, examined following two freezing and thawing cycles, was unaffected by variation in critical formulation parameters, i.e. a ±0.3 pH unit change relative to the reference mAb1, a ±10% variation in mAb1 concentration, and/or a ±20% variation in sucrose.

The following effects were observed:

No precipitate was detected by either visual inspection or turbidity measurements (OD at 405 nm);

No loss of protein was observed (RP-UPLC);

The pH of the formulations remained constant;

No meaningful differences were observed in the subvisible particulate counts, determined by light obscuration (HIAC) or micro flow imaging (MFI) between the study formulations. There was a slight increase in subvisible particles after 2 cycles of F/T, which could be removed by filtering through a 0.22 μm filter prior to filling the DP.

No appreciable changes in purity, as determined by SE-UPLC, were observed in all formulations following two freezing and thawing cycles;

No appreciable change in the distribution of charge variants, as determined by iCIEF, was observed in all formulations following two freezing and thawing cycles.

The bioassay results demonstrated that mAb1 activity was maintained in all formulations subjected to 2 cycles of freezing and thawing.

CONCLUSIONS

Design-Of-experiment (DOE)-based pre-PAR and PAR studies were used to evaluate the effect of formulation parameters as well as the interactions on the formulation stability. The pre-PAR study with accelerated and stress stability identified pH, mAb1 concentration, and sucrose concentration as the critical formulation parameters. A full factorial PAR study with long-term shelf-life stability demonstrated that variation in the critical formulation parameters, within the range studies, did not affect mAb1 DP quality.

Specifically, the stability and potency of 50 mg/mL mAb1 DP stored at 5° C. for 12 months were unaffected by a ±10% variation in protein concentration, a ±20% variation in sucrose, L-proline and/or histidine concentration, and/or ±50% variation in polysorbate 80 concentration, and/or a ±0.3 pH unit variation.

The robustness of mAb1 formulation was demonstrated by the PAR study. Overall, the results from the pre-PAR and PAR study supported that variability in the compositions of the mAb1 formulation within the ranges studied would not adversely impact the stability of the mAb1 DP under the recommended storage conditions (2 to 8° C.).

The 50 mg/mL mAb1 FDS samples were stable after two cycles of freezing and thawing (−30° C. freeze and room temperature thaw). The stability of mAb1 FDS to freeze/thaw stress was unaffected by a ±10% change in mAb1 concentration, a ±20% change in sucrose, and/or a ±0.3 pH unit change relative to the control mAb1 FDS (50 mg/mL). The results from these freeze/thaw studies provide support that 50 mg/mL mAb1 FDS can be frozen and thawed during the manufacture of mAb1 DP without adversely impacting the stability of the FDS.

Example 14: Containers

The mAb1 formulations were developed in glass vials (for delivery by intravenous infusion). The container for mAb1 drug product intended for later clinical development and product commercialization is also a pre-filled syringe, which is presented as either a stand-alone syringe for self-injection or incorporated into an auto injector device for self-administration.

Example 15: Stability of mAb1 Formulation in Glass Vials

Tables 32-35 summarize the stability of exemplary mAb1 formulations in 10 mL glass vials.

TABLE 32

Research stability of mAb1 formulation stored at 2-8° C.

| | |
|---|---|
| Formulation | 50 mg/mL mAb1, 10 mM L-histidine, 5% (w/v) sucrose, 1.5% (w/v) L-proline, and 0.2% (w/v) polysorbate 80, pH 6.0 |
| Fill Volume | 5.5 mL |
| Container/Closure | 10 mL Type 1 glass vials with a 20 mm FluroTec ®-coated coated 4432/50 chlorobutyl stopper |

| | | Length of Storage at 5° C. (months) | | | | | | | |
|---|---|---|---|---|---|---|---|---|---|
| Assay | | 0 | 1 | 3 | 6 | 9 | 12 | 18 | 24 |
| Color and Appearance | | Pass | Pass | Pass | Pass | Pass | Pass | Pass | |
| Turbidity (increase in OD at 405 nm) | | 0.00 | 0.00 | 0.00 | 0.00 | 0.00 | 0.00 | 0.00 | |
| pH | | 6.0 | 6.0 | 6.0 | 6.0 | 6.0 | 6.0 | 6.0 | |
| Subvisible | 2 to 10 μm | 175 | NR | 62 | 772 | NR | 1730 | NR | |
| Particulate | ≥10 μm | 8 | NR | 3 | 144 | NR | 18 | NR | |
| Analysis by MFI (N/mL) | ≥25 μm | 0 | NR | 1 | 19 | NR | 4 | NR | |
| % Protein Recovered by RP-UPLC | | 100 | 102 | 103 | 101 | 105 | 103 | 104 | |
| Purity by MCE-SDS | Non-reduced; % main peak | 99.1 | NR | NR | 99.1 | NR | 99.2 | NR | |
| | Reduced; % heavy + light chain | 100 | NR | NR | 100 | NR | 100 | NR | |
| Purity by SE-UPLC | % HMW | 0.3 | 0.3 | 0.3 | 0.4 | 0.4 | 0.4 | 0.4 | |
| | % Monomer | 99.1 | 99.3 | 99.3 | 99.3 | 99.2 | 99.2 | 99.2 | |
| | % LMW | 0.6 | 0.4 | 0.4 | 0.4 | 0.4 | 0.4 | 0.4 | |
| Charge Variant Analysis by CEX-UPLC | % Acidic | 18.9 | 18.9 | 18.9 | 19.8 | 20.5 | 19.8 | 18.9 | |
| | % Main | 53.5 | 53.3 | 53.4 | 54.7 | 54.3 | 54.0 | 52.9 | |
| | % Basic | 27.5 | 27.8 | 27.7 | 25.6 | 25.2 | 26.2 | 28.2 | |
| Charge Variant Analysis by iCIEF | % Acidic | 33.8 | NR | 34.4 | 34.2 | NR | 34.9 | NR | |
| | % Main | 54.8 | NR | 54.2 | 54.3 | NR | 54.3 | NR | |
| | % Basic | 11.4 | NR | 11.4 | 11.4 | NR | 1.8 | NR | |
| % Relative Potency (bioassay) | | 92 | NR | NR | 122 | NR | 112 | NR | |

CEX, Cation exchange; DS, Drug substance; HMW, High molecular weight; iCIEF, imaged capillary isoelectric-focusing, LMW, Low molecular weight; MFI, Microflow-imaging; NR, Not required; OD, Optical density; RP, Reverse phase; SE, Size exclusion; UPLC, Ultra-performance liquid chromatography

TABLE 33

Research stability of mAb1 formulation at accelerated and stress conditions

| Formulation | 50 mg/mL mAb1, 10 mM L-histidine, 5% (w/v) sucrose, 1.5% (w/v) L-proline, and 0.2% (w/v) polysorbate 80, pH 6.0 |
|---|---|
| Fill Volume | 5.5 mL |
| Container/Closure | 10 mL Type 1 glass vials with a 20 mm FluroTec ®-coated 4432/50 chlorobutyl stopper |

| Assay | | 25° C./60% RH Storage (months) | | | | 40° C. Storage (days) | | |
|---|---|---|---|---|---|---|---|---|
| | | 0 | 1 | 3 | 6 | 7 | 14 | 28 |
| Color and appearance | | Pass | Pass | Pass | Pass | Pass | Pass | Pass |
| Turbidity (Increase in OD at 405 nm) | | 0.00 | 0.00 | 0.00 | 0.00 | 0.00 | 0.00 | 0.00 |
| pH | | 6.0 | 6.0 | 6.0 | 6.0 | 6.0 | 6.0 | 6.0 |
| Subvisible particulate analysis by MFI (#/mL) | 2-10 µm | 175 | NR | 326 | 2083 | NR | NR | 288 |
| | ≥10 µm | 8 | NR | 4 | 109 | NR | NR | 14 |
| | ≥25 µm | 0 | NR | 3 | 3 | NR | NR | 1 |
| % Protein recovered by SE-UPLC | | 100 | 102 | 104 | 101 | 100 | 101 | 102 |
| Purity by MCE-SDS | Non-reduced; % main peak | 99.1 | NR | NR | 98.8 | NR | NR | 98.6 |
| | Reduced; % heavy + light chain | 100 | NR | NR | 99.7 | NR | NR | 99.7 |
| Purity by SE-UPLC | % HMW | 0.3 | 0.4 | 0.5 | 0.6 | 0.5 | 0.8 | 1.2 |
| | % Monomer | 99.1 | 99.1 | 99.1 | 99.0 | 98.7 | 98.5 | 98.1 |
| | % LMW | 0.6 | 0.5 | 0.4 | 0.4 | 0.7 | 0.7 | 0.7 |
| Charge variant analysis by CEX-UPLC | % Acidic | 18.9 | 19.4 | 22.1 | 28.3 | 20.0 | 22.0 | 27.1 |
| | % Main | 53.5 | 52.7 | 51.2 | 48.6 | 51.9 | 50.2 | 46.7 |
| | % Basic | 27.5 | 27.9 | 26.8 | 23.2 | 27.1 | 27.7 | 26.2 |
| Charge variant analysis by iCIEF | % Acidic | 33.8 | NR | NR | 41.9 | NR | NR | 46.4 |
| | % Main | 54.8 | NR | NR | 46.5 | NR | NR | 40.9 |
| | % Basic | 11.4 | NR | NR | 11.6 | NR | NR | 12.7 |
| % Relative potency by bioassay | | 92 | NR | NR | 91 | NR | NR | 83 |

CEX, Cation exchange;
DS, Drug substance;
HMW, High molecular weight;
iCIEF, imaged capillary isoelectric-focusing,
LMW, Low molecular weight;
MFI, Microflow- imaging;
NR, Not required;
OD, Optical density;
RP, Reverse phase;
SE, Size exclusion;
UPLC, Ultra-performance liquid chromatography

TABLE 34

Research stability of mAb1 formulation stored at 2-8° C.

| Formulation | 505 mg/mL mAb1, 10 mM L-histidine, 5% (w/v) sucrose, 1.5% (w/v) L-proline, and 0.2% (w/v) polysorbate 80, pH 6.0 |
|---|---|
| Fill Volume | 7.44 mL |
| Container/Closure | 10 mL Type 1 glass vials with a 20 mm FluroTec ®-coated coated 4432/50 chlorobutyl stopper |

| Assay | | Length of Storage at 2-8° C. (months) | | | | | | |
|---|---|---|---|---|---|---|---|---|
| | | 0 | 1 | 3 | 6 | 9 | 12 | 18 | 24 |
| Color and Appearance | | Pass | Pass | Pass | Pass | Pass | | | |
| Turbidity (increase in OD at 405 nm) | | 0.00 | 0.00 | 0.00 | 0.00 | 0.00 | | | |
| pH | | 6.0 | 6.0 | 6.0 | 6.0 | 6.0 | | | |
| Subvisible Particulate Analysis by HIAC (N/mL) | ≥10 µm | 3 | NR | 2 | 4 | NR | | | |
| | ≥25 µm | 0 | NR | 0 | 1 | NR | | | |
| Subvisible Particulate Analysis by MFI (N/mL) | 2 to 10 µm | 183 | NR | 207 | 1044 | NR | | | |
| | ≥10 µm | 3 | NR | 7 | 19 | NR | | | |
| | ≥25 µm | 1 | NR | 3 | 5 | NR | | | |
| % Protein Recovered by RP-UPLC | | 100 | 99 | 102 | 102 | 94 | | | |

TABLE 34-continued

Research stability of mAb1 formulation stored at 2-8° C.

| | | | | | | |
|---|---|---|---|---|---|---|
| Purity by MCE-SDS | Non-reduced; % main peak | 99.2 | NR | 99.4 | 99.2 | NR |
| | Reduced; % heavy + light chain | 100 | NR | 100 | 100 | NR |
| Purity by SE-UPLC | % HMW | 0.7 | 0.6 | 0.5 | 0.5 | 0.6 |
| | % Monomer | 98.8 | 98.8 | 98.9 | 99.0 | 98.9 |
| | % LMW | 0.6 | 0.6 | 0.5 | 0.4 | 0.5 |
| Charge Variant Analysis by CEX-UPLC | % Acidic | 21.2 | 21.2 | 22.3 | 19.6 | 21.5 |
| | % Main | 52.0 | 52.1 | 52.0 | 51.9 | 52.0 |
| | % Basic | 26.8 | 26.8 | 25.7 | 28.6 | 26.6 |
| Charge Variant Analysis by iCIEF | % Acidic | 34.3 | NR | 34.7 | 34.6 | NR |
| | % Main | 52.1 | NR | 51.9 | 51.9 | NR |
| | % Basic | 13.7 | NR | 13.4 | 13.4 | NR |
| % Relative Potency (bioassay) | | 113 | NR | 105 | 128 | NR |

CEX, Cation exchange; DS, Drug substance; HMW, High molecular weight; iCIEF, imaged capillary isoelectric-focusing, LMW, Low molecular weight; MFI, Microflow-imaging; NR, Not required; OD, Optical density; RP, Reverse phase; SE, Size exclusion; UPLC, Ultra-performance liquid chromatography

TABLE 35

Research stability of mAb1 formulation at accelerated and stress conditions

| | |
|---|---|
| Formulation | 50 mg/mL mAb1, 10 mM L-histidine, 5% (w/v) sucrose, 1.5% (w/v) L-proline, and 0.2% (w/v) polysorbate 80, pH 6.0 |
| Fill Volume | 7.44 mL |
| Container/Closure | 10 mL Type 1 glass vials with a 20 mm FluroTec ®-coated 4432/50 chlorobutyl stopper |

| | | 25° C./60% RH Storage (months) | | | | 40° C. Storage (days) | | |
|---|---|---|---|---|---|---|---|---|
| Assay | | 0 | 1 | 3 | 6 | 7 | 14 | 28 |
| Color and appearance | | Pass | Pass | Pass | Pass | Pass | Pass | Pass |
| Turbidity (Increase in OD at 405 nm) | | 0.00 | 0.00 | 0.00 | 0.00 | 0.00 | 0.00 | 0.00 |
| pH | | 6.0 | 6.0 | 6.0 | 6.0 | 6.0 | 6.0 | 6.0 |
| Subvisible Particulate Analysis by HIAC | ≥10 μm | 3 | NR | 4 | 11 | NR | NR | 5 |
| | ≥25 μm | 0 | NR | 0 | 2 | NR | NR | 0 |
| Subvisible particulate analysis by MFI (#/mL) | 2-10 μm | 183 | NR | 540 | 1439 | NR | NR | 799 |
| | ≥10 μm | 3 | NR | 18 | 16 | NR | NR | 92 |
| | ≥25 μm | 1 | NR | 1 | 1 | NR | NR | 1 |
| % Protein recovered by SE-UPLC | | 100 | 100 | 101 | 101 | 101 | 99 | 100 |
| Purity by MCE-SDS | Non-reduced; % main peak | 99.2 | NR | 99.3 | 98.7 | NR | NR | 98.6 |
| | Reduced; % heavy + light chain | 100 | NR | 100 | 100 | NR | NR | 99.5 |
| Purity by SE-UPLC | % HMW | 0.7 | 0.6 | 0.7 | 0.8 | 0.6 | 0.8 | 1.3 |
| | % Monomer | 98.8 | 98.8 | 98.8 | 98.7 | 98.7 | 98.5 | 97.9 |
| | % LMW | 0.6 | 0.7 | 0.6 | 0.6 | 0.7 | 0.8 | 0.8 |
| Charge variant analysis by CEX-UPLC | % Acidic | 21.2 | 21.7 | 25.3 | 24.4 | 20.5 | 23.2 | 25.8 |
| | % Main | 52.0 | 52.1 | 51.4 | 50.5 | 52.4 | 51.0 | 49.7 |
| | % Basic | 26.8 | 26.2 | 23.3 | 25.1 | 27.0 | 25.9 | 24.6 |
| Charge variant analysis by iCIEF | % Acidic | 34.3 | NR | 40.0 | 45.4 | NR | NR | 46.9 |
| | % Main | 52.1 | NR | 47.1 | 43.7 | NR | NR | 39.7 |
| | % Basic | 13.7 | NR | 12.9 | 11.0 | NR | NR | 13.3 |
| % Relative potency by bioassay | | 113 | NR | 143 | 99 | NR | NR | 88 |

CEX, Cation exchange;
DS, Drug substance;
HMW, High molecular weight;
iCIEF, imaged capillary isoelectric-focusing,
LMW, Low molecular weight;
MFI, Microflow- imaging;
NR, Not required;
OD, Optical density;
RP, Reverse phase;
SE, Size exclusion;
UPLC, Ultra-performance liquid chromatography The two formulations at different fill volumes were found to be stable to stress (40° C./75% RH) (data not shown).

Example 16: Stability of mAb1 Formulation in Pre-Filled Syringes

Tables 36-38 summarize the stability of high concentration mAb1 formulations in pre-filled syringes.

TABLE 36

Research Stability of mAb1 Drug Product in Pre-filled Syringe (PFS) Stored at 5° C.

| | |
|---|---|
| Formulation | 175 mg/mL mAb1, 10 mM histidine, 5% (w/v) sucrose, 1.5% (w/v) L-proline, 0.2% (w/v) polysorbate 80, pH 6.0 |
| Fill Volume | 1.2 mL |
| Container/Closure | Nuova Ompi EZ Fill 2.25 mL glass syringe with a 27G ½ thin wall needle and FM30 needle shield closed with a FluroTec ® coated 4023/50 rubber plunger |

| Assay | | Length of Storage at 5° C. (months) | | | | | |
|---|---|---|---|---|---|---|---|
| | | 0 | 1 | 3 | 6 | 9 | 12 |
| Color and appearance | | Pass | Pass | Pass | Pass | Pass | Pass |
| Turbidity (Increase in OD at 405 nm) | | 0.00 | 0.01 | 0.00 | 0.00 | 0.00 | 0.00 |
| pH | | 6.0 | 6.0 | 6.0 | 6.0 | 6.0 | 6.0 |
| Subvisible | ≥10 μm | 35 | NR | 17 | 59 | NR | 13 |
| particulate | ≥25 μm | 0 | NR | 4 | 1 | NR | 1 |
| analysis by HIAC (#/mL) | | | | | | | |
| Particulate | 2 to 10 μm | 21326 | NR | 8613 | NA | NR | NA |
| analysis by MFI | ≥10 μm | 82 | NR | 303 | NA | NR | NA |
| (particles/mL) | ≥25 μm | 3 | NR | 2 | NA | NR | NA |
| % Protein recovered by RP-UPLC | | 100 | 96 | 97 | 100 | 98 | 100 |
| Purity by MCE-SDS | Non-reduced; % main peak | 97.6 | NR | NR | 97.7 | 97.1 | NA |
| | Reduced; % heavy + light chain | 99.6 | NR | NR | 99.8 | 99.8 | NA |
| Purity by SE-UPLC | % HMW | 0.6 | 0.6 | 0.7 | 0.7 | 0.8 | 0.9 |
| | % Native | 99.1 | 98.9 | 99.1 | 98.7 | 98.7 | 98.6 |
| | % LMW | 0.3 | 0.5 | 0.2 | 0.5 | 0.5 | 0.5 |
| Charge variant analysis by CEX-UPLC | % Acidic | 18.6 | 18.5 | 18.2 | 18.6 | 19.3 | 18.8 |
| | % Main | 53.4 | 54.8 | 54.3 | 53.2 | 53.5 | 55.5 |
| | % Basic | 27.9 | 26.8 | 27.5 | 25.3 | 25.6 | 24.3 |
| Charge variant analysis by iCIEF | % Acidic | 30.2 | NR | 30.2 | 32.9 | NR | NA |
| | % Main | 55.9 | NR | 55.9 | 53.4 | NR | NA |
| | % Basic | 13.9 | NR | 13.9 | 13.7 | NR | NA |
| % Relative potency (bioassay) | | 87 | NR | NR | 141 | NR | NA |

TABLE 37

Research Stability of mAb1 Drug Product in Pre-filled Syringe (PFS) Stored at Accelerated Conditions

| | |
|---|---|
| Formulation | 175 mg/mL mAb1, 10 mM histidine, 5% (w/v) sucrose, 1.5% (w/v) L-proline, 0.2% (w/v) polysorbate 80, pH 6.0 |
| Fill Volume | 1.2 mL |
| Container/Closure | Nuova Ompi EZ Fill 2.25 mL glass syringe with a 27G ½ thin wall needle and FM30 needle shield closed with a FluroTec ® coated 4023/50 rubber plunger |

| Assay | | 25° C./60% RH Storage (months) | | | | 40° C. Storage (days) | | |
|---|---|---|---|---|---|---|---|---|
| | | 0 | 1 | 3 | 6 | 7 | 14 | 28 |
| Color and appearance | | Pass | Pass | Pass | Pass | Pass | Pass | Pass |
| Turbidity (Increase in OD at 405 nm) | | 0.00 | 0.00 | 0.00 | 0.00 | 0.00 | 0.00 | 0.00 |
| pH | | 6.0 | 6.0 | 6.0 | 6.1 | 6.0 | 6.0 | 6.0 |
| Subvisible | ≥10 μm | 3 | NR | 13 | 30 | NR | NR | 14 |
| particulate | ≥25 μm | 1 | NR | 1 | 1 | NR | NR | 3 |
| analysis by HIAC (#/mL) | | | | | | | | |

TABLE 37-continued

Research Stability of mAb1 Drug Product in Pre-filled Syringe (PFS) Stored at Accelerated Conditions

| | | | | | | | | |
|---|---|---|---|---|---|---|---|---|
| Particulate analysis by MFI (particles/mL) | 2-10 μm | 21326 | NR | 4605 | NA | NR | NR | 3717 |
| | ≥10 μm | 82 | NR | 225 | NA | NR | NR | 51 |
| | ≥25 μm | 3 | NR | 2 | NA | NR | NR | 8 |
| % Protein recovered by RP-UPLC | | 100 | 98 | 98 | 100 | 100 | 100 | 98 |
| Purity by MCE-SDS | Non-reduced; % main peak | 97.6 | NR | 97.7 | 96.5 | NR | NR | 96.8 |
| | Reduced; % heavy + light chain | 99.6 | NR | 99.2 | 99.7 | NR | NR | 99.4 |
| Purity by SE-UPLC | % HMW | 0.6 | 0.9 | 1.2 | 1.6 | 1.6 | 2.5 | 3.9 |
| | % Native | 99.1 | 98.6 | 98.5 | 97.7 | 97.8 | 96.9 | 95.5 |
| | % LMW | 0.3 | 0.5 | 0.3 | 0.6 | 0.6 | 0.7 | 0.6 |
| Charge variant analysis by CEX-UPLC | % Acidic | 18.6 | 19.0 | 21.3 | 25.5 | 20.0 | 22.1 | 24.3 |
| | % Main | 53.4 | 54.3 | 52.0 | 46.5 | 51.8 | 49.8 | 48.9 |
| | % Basic | 27.9 | 26.8 | 26.6 | 28.1 | 28.3 | 28.1 | 26.8 |
| Charge variant analysis by iCIEF | % Acidic | 30.2 | NR | 36.8 | 44.9 | NR | NR | 45.6 |
| | % Main | 55.9 | NR | 49.6 | 42.8 | NR | NR | 40.5 |
| | % Basic | 13.9 | NR | 13.6 | 12.3 | NR | NR | 13.9 |
| % Relative potency by bioassay | | 87 | NR | NR | 137 | NR | NR | 83 |

TABLE 38

Research Stability of mAb1 Drug Product in Pre-filled Syringe (PFS)-Effect of Stress Conditions

| | |
|---|---|
| Formulation | 175 mg/mL mAb1, 10 mM histidine, 5% (w/v) sucrose, 1.5% (w/v) L-proline, 0.2% (w/v) polysorbate 80, pH 6.0 |
| Fill Volume | 1.2 mL |
| Container/Closure | Nuova Ompi EZ Fill 2.25 mL glass syringe with a 27 G 1/2 thin wall needle and FM30 needle shield closed with a FluroTec ® coated 4023/50 rubber plunger |

| | | Agitation (min) | | |
|---|---|---|---|---|
| Assay | | 0 | 60 | 120 |
| Color and appearance | | Pass | Pass | Pass |
| Turbidity (Increase in OD at 405 nm) | | 0.00 | 0.00 | 0.00 |
| pH | | 6.0 | 6.0 | 6.0 |
| Subvisible particulate analysis by HIAC (#/mL) | ≥10 μm | 3 | NR | 5 |
| | ≥25 μm | 1 | NR | 5 |
| Particulate analysis by MFI (particles/mL) | 2 to 10 μm | 21326 | NR | 13896 |
| | ≥10 μm | 82 | NR | 55 |
| | ≥25 μm | 3 | NR | 3 |
| % Protein recovered by RP-UPLC | | 100 | 100 | 100 |
| Purity by MCE-SDS | Non-reduced; % main peak | 97.6 | NR | 97.9 |
| | Reduced; % heavy + light chain | 99.6 | NR | 99.5 |
| Purity by SE-UPLC | % HMW | 0.6 | 0.6 | 0.6 |
| | % Native | 99.1 | 98.9 | 98.8 |
| | % LMW | 0.3 | 0.6 | 0.6 |
| Charge variant analysis by CEX-UPLC | % Acidic | 18.6 | 18.8 | 19.0 |
| | % Main | 53.4 | 53.2 | 53.5 |
| | % Basic | 27.9 | 28.1 | 27.5 |
| Charge variant analysis by iCIEF | % Acidic | 30.2 | NR | 30.4 |
| | % Main | 55.9 | NR | 55.5 |
| | % Basic | 13.9 | NR | 14.1 |
| % Relative potency by bioassay | | 87 | NR | 100 |

Example 17: Compatibility of mAb1 Formulations in Intravenous (IV) Delivery Devices For the compatibility assessment, 50 mg/mL mAb1 formulation was added to a 100 mL IV bag, containing either 0.9% Sodium Chloride Injection or 5% Dextrose Injection, to assess whether mAb1 is stable when delivered intravenously. To support the variability in patient weights, two admixture concentrations, 1.0 mg/mL mAb1 and 25 mg/mL mAb1, were examined in this study to reflect the low and high dosing conditions. The following IV admixture components were used during the compatibility studies:

Drug Product
　50 mg/mL mAb1 DP
Diluents
　0.9% Sodium Chloride Injection
　5% Dextrose Injection
IV Bags
　IV bags made of polyvinyl chloride (PVC) with di-(2-ethylhexyl)phthalate (DEHP) prefilled with 0.9% Sodium Chloride Injection
　IV bags made of polyvinyl chloride (PVC) with DEHP prefilled with 5% Dextrose Injection
　IV bags made of polyolefin (PO) prefilled with 0.9% Sodium Chloride Injection
　IV bags made of polyolefin (PO) prefilled with 5% Dextrose Injection
　IV bags made of polypropylene prefilled with 0.9% Sodium Chloride Injection
　IV bottles made of polypropylene prefilled with 0.9% Sodium Chloride Injection
IV Pumps
　Peristaltic pump
　Fluid displacement pump
IV Infusion Sets
　IV set made of PVC with DEHP
　IV set made of PVC with dioctyl terephthalate (DEHT)
　IV set made of PVC with trioctyl trimellitate (TOTM)
　IV set made of polyethylene lined PVC
　IV set made of polyurethane
Filters
　0.2 μm polyethersulfone inline filter
　1.2 μm polyethersulfone inline filter
　5 μm polyethersulfone inline filter
　15 μm polyethersulfone inline filter.

The DPs used in this study were GMP manufactured using a representative DP commercial manufacturing process. The IV bags containing the admixture were initially held for 24 hours at 5° C.; the bags were then incubated for at least 8 hours at 25° C. After these incubations, each of the infusion sets was connected to the IV bag, primed with the admixture and held for 1 hour at ambient room temperature. Each admixture was then pumped through the respective infusion sets at rates of 25 mL/h and 500 mL/h.

Methods Used to Assess Admixture Compatibility:
The compatibility of the mAb1 admixture with materials used in the IV delivery device was assessed using the following assays:
　Color and appearance by visual inspection
　pH
　Turbidity measured by increase in Optical Density (OD) at 405 nm
　Subvisible particulate analysis on admixture by light obscuration (HIAC)
　Protein concentration of mAb1 by reversed-phase ultra performance liquid chromatography (RP-UPLC)
　Purity by SE-UPLC
　Charge variant analysis by CEX-UPLC
　Potency, by bioassay: The relative potency of each sample is determined using the bioassay and is defined as: ($IC_{50}$ Reference Sample/$IC_{50}$ Sample)*100%. The measured potency of storage stability samples must be within 50-150% of the measured potency of the reference standard.

Results and Conclusions:
The 50 mg/mL mAb1 formulation, diluted in either 0.9% Sodium Chloride Injection or 5% Dextrose Injection to concentrations of either 1.0 mg/mL or 25 mg/mL was physically and chemically stable under all conditions tested within the proposed dose ranges and administration conditions. These data support the following conclusions pertaining to dose preparation and IV administration of mAb1 DP:

0.9% Sodium Chloride Injection and 5% Dextrose Injection IV bags made of PVC with DEHP, PO, and polypropylene are compatible with mAb1 IV administration.
　mAb1 DP can be diluted to concentrations as low as 1.0 mg/mL in PVC, PO or polypropylene IV bags containing either 0.9% Sodium Chloride or 5% Dextrose for IV administration.
　mAb1 DP can be diluted to concentrations as high as 25.0 mg/mL in PVC, PO or polypropylene IV bags containing either 0.9% Sodium Chloride or 5% Dextrose for IV administration.
　mAb1 admixture in either 0.9% Sodium Chloride or 5% Dextrose was stable after incubation in a PVC, PO or polypropylene IV bag for periods of up to 24 hours at 5° C. and 8 hours at 25° C. The diluted mAb1 DP may be administered within 6 hours of preparation.
　Diluted mAb1 can be administered using a standard infusion pump.
　Diluted mAb1 can be administered with an infusion set composed of either PVC containing DEHP, PVC containing TO™, polyethylene or polyurethane.
　mAb1 is compatible with the use of an inline 0.2 μm-5 μm polyethersulfone filter.
　Diluted mAb1 can be administered at a rate ranging from 25 to 500 mL/hour.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A stable liquid pharmaceutical formulation, comprising:
(a) 5 mg/mL ±0.75 mg/mL to 250 mg/mL ±37.5 mg/mL of an antibody that binds specifically to human programmed death-1 (PD-1), wherein the antibody comprises three heavy chain complementarity determining regions (CDRs) (HCDR1, HCDR2 and HCDR3) contained in a heavy chain variable region (HCVR) comprising the amino acid sequence of SEQ ID NO: 1 and three light chain CDRs (LCDR1, LCDR2 and LCDR3) contained in a light chain variable region (LCVR) comprising the amino acid sequence of SEQ ID NO: 2;
(b) 10 mM ±2 mM histidine buffer,
(c) 0.2% ±0.1% w/v polysorbate,
(d) 5% ±1% w/v sucrose, and
(e) 1.5% ±0.3% w/v proline,
in water at pH 6.0±0.3.

2. The pharmaceutical formulation of claim 1, wherein the antibody concentration is 25 mg/mL ±3.75 mg/mL.

3. The pharmaceutical formulation of claim 1, wherein the antibody concentration is 50 mg/mL ±7.5 mg/mL.

4. The pharmaceutical formulation of claim 1, wherein the antibody concentration is 150 mg/mL ±22.5 mg/mL.

5. The pharmaceutical formulation of claim 1, wherein the antibody concentration is 175 mg/mL ±26.25 mg/mL.

6. The pharmaceutical formulation of claim 1, wherein the histidine buffer is prepared from L-histidine and L-histidine monohydrochloride monohydrate.

7. The pharmaceutical formulation of claim 1, wherein the histidine buffer is prepared from 4.8 mM ±0.96 mM L-histidine and 5.2 mM ±1.04 mM L-histidine monohydrochloride monohydrate.

8. The pharmaceutical formulation of claim 2, wherein the histidine buffer is prepared from 4.8 mM ±0.96 mM L-histidine and 5.2 mM ±1.04 mM L-histidine monohydrochloride monohydrate.

9. The pharmaceutical formulation of claim 3, wherein the histidine buffer is prepared from 4.8 mM ±0.96 mM L-histidine and 5.2 mM ±1.04 mM L-histidine monohydrochloride monohydrate.

10. The pharmaceutical formulation of claim 4, wherein the histidine buffer is prepared from 4.8 mM ±0.96 mM L-histidine and 5.2 mM ±1.04 mM L-histidine monohydrochloride monohydrate.

11. The pharmaceutical formulation of claim 5, wherein the histidine buffer is prepared from 4.8 mM ±0.96 mM L-histidine and 5.2 mM ±1.04 mM L-histidine monohydrochloride monohydrate.

12. The pharmaceutical formulation of claim 1, wherein the polysorbate is polysorbate 80.

13. The pharmaceutical formulation of claim 1, wherein the formulation has a viscosity of less than 20 cP at 25° C.

14. The pharmaceutical formulation of claim 3, wherein the formulation has a viscosity of less than 10 cP at 25° C.

15. The pharmaceutical formulation of claim 1, wherein the antibody comprises a HCVR comprising the amino acid sequence of SEQ ID NO: 1 and a LCVR comprising the amino acid sequence of SEQ ID NO: 2.

16. The pharmaceutical formulation of claim 1, wherein HCDR1 comprises the amino acid sequence of SEQ ID NO: 3, HCDR2 comprises the amino acid sequence of SEQ ID NO: 4, HCDR3 comprises the amino acid sequence of SEQ ID NO: 5, LCDR1 comprises the amino acid sequence of SEQ ID NO: 6, LCDR2 comprises the amino acid sequence of SEQ ID NO: 7, and LCDR3 comprises the amino acid sequence of SEQ ID NO: 8.

17. The pharmaceutical formulation of claim 1, wherein the antibody comprises a heavy chain and a light chain, wherein the heavy chain comprises an amino acid sequence selected from SEQ ID NOs: 9 and 11.

18. The pharmaceutical formulation of claim 1, wherein the antibody comprises a heavy chain and a light chain, wherein the light chain comprises the amino acid sequence of SEQ ID NO: 10.

19. The pharmaceutical formulation of claim 1, wherein the antibody comprises a heavy chain and a light chain, wherein the heavy chain comprises the amino acid sequence of SEQ ID NO: 9, and the light chain comprises the amino acid sequence of SEQ ID NO: 10.

20. The pharmaceutical formulation of claim 1, wherein the antibody comprises a heavy chain and a light chain, wherein the heavy chain comprises the amino acid sequence of SEQ ID NO: 11, and the light chain comprises the amino acid sequence of SEQ ID NO: 10.

21. The pharmaceutical formulation of claim 1, comprising:
(a) 25 mg/mL of the antibody,
(b) 0.74 mg/mL of L-histidine,
(c) 1.1 mg/mL of L-histidine monohydrochloride monohydrate,
(d) 2 mg/mL of polysorbate 80,
(e) 50 mg/mL of sucrose, and
(f) 15 mg/mL of proline.

22. The pharmaceutical formulation of claim 1, comprising:
(a) 50 mg/mL of the antibody,
(b) 0.74 mg/mL of L-histidine,
(c) 1.1 mg/mL of L-histidine monohydrochloride monohydrate,
(d) 2 mg/mL of polysorbate 80,
(e) 50 mg/mL of sucrose, and
(f) 15 mg/mL of proline.

23. The pharmaceutical formulation of claim 1, comprising:
(a) 150 mg/mL of the antibody,
(b) 0.74 mg/mL of L-histidine,
(c) 1.1 mg/mL of L-histidine monohydrochloride monohydrate,
(d) 2 mg/mL of polysorbate 80,
(e) 50 mg/mL of sucrose, and
(f) 15 mg/mL of proline.

24. The pharmaceutical formulation of claim 1, comprising:
(a) 175 mg/mL of the antibody,
(b) 0.74 mg/mL of L-histidine,
(c) 1.1 mg/mL of L-histidine monohydrochloride monohydrate,
(d) 2 mg/mL of polysorbate 80,
(e) 50 mg/mL of sucrose, and
(f) 15 mg/mL of proline.

* * * * *

SEQUENCE LISTING

<160> NUMBER OF SEQ ID NOS: 11

<210> SEQ ID NO 1
<211> LENGTH: 117
<212> TYPE: PRT

```
<213> ORGANISM: Artificial Sequence
<220> FEATURE:
<223> OTHER INFORMATION: synthetic

<400> SEQUENCE: 1

Glu Val Gln Leu Leu Glu Ser Gly Gly Val Leu Val Gln Pro Gly Gly
1               5                   10                  15

Ser Leu Arg Leu Ser Cys Ala Ala Ser Gly Phe Thr Phe Ser Asn Phe
            20                  25                  30

Gly Met Thr Trp Val Arg Gln Ala Pro Gly Lys Gly Leu Glu Trp Val
        35                  40                  45

Ser Gly Ile Ser Gly Gly Arg Asp Thr Tyr Phe Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Gly Glu Asp Thr Ala Val Tyr Tyr Cys
                85                  90                  95

Val Lys Trp Gly Asn Ile Tyr Phe Asp Tyr Trp Gly Gln Gly Thr Leu
            100                 105                 110

Val Thr Val Ser Ser
        115

<210> SEQ ID NO 2
<211> LENGTH: 107
<212> TYPE: PRT
<213> ORGANISM: Artificial Sequence
<220> FEATURE:
<223> OTHER INFORMATION: synthetic

<400> SEQUENCE: 2

Asp Ile Gln Met Thr Gln Ser Pro Ser Ser Leu Ser Ala Ser Val Gly
1               5                   10                  15

Asp Ser Ile Thr Ile Thr Cys Arg Ala Ser Leu Ser Ile Asn Thr Phe
            20                  25                  30

Leu Asn Trp Tyr Gln Gln Lys Pro Gly Lys Ala Pro Asn Leu Leu Ile
        35                  40                  45

Tyr Ala Ala Ser Ser Leu His Gly Gly Val Pro Ser Arg Phe Ser Gly
    50                  55                  60

Ser Gly Ser Gly Thr Asp Phe Thr Leu Thr Ile Arg Thr Leu Gln Pro
65                  70                  75                  80

Glu Asp Phe Ala Thr Tyr Tyr Cys Gln Gln Ser Ser Asn Thr Pro Phe
                85                  90                  95

Thr Phe Gly Pro Gly Thr Val Val Asp Phe Arg
            100                 105

<210> SEQ ID NO 3
<211> LENGTH: 8
<212> TYPE: PRT
<213> ORGANISM: Artificial Sequence
<220> FEATURE:
<223> OTHER INFORMATION: synthetic

<400> SEQUENCE: 3

Gly Phe Thr Phe Ser Asn Phe Gly
1               5

<210> SEQ ID NO 4
<211> LENGTH: 8
<212> TYPE: PRT
<213> ORGANISM: Artificial Sequence
```

-continued

<220> FEATURE:
<223> OTHER INFORMATION: synthetic

<400> SEQUENCE: 4

Ile Ser Gly Gly Gly Arg Asp Thr
1               5

<210> SEQ ID NO 5
<211> LENGTH: 10
<212> TYPE: PRT
<213> ORGANISM: Artificial Sequence
<220> FEATURE:
<223> OTHER INFORMATION: synthetic

<400> SEQUENCE: 5

Val Lys Trp Gly Asn Ile Tyr Phe Asp Tyr
1               5                   10

<210> SEQ ID NO 6
<211> LENGTH: 6
<212> TYPE: PRT
<213> ORGANISM: Artificial Sequence
<220> FEATURE:
<223> OTHER INFORMATION: synthetic

<400> SEQUENCE: 6

Leu Ser Ile Asn Thr Phe
1               5

<210> SEQ ID NO 7
<211> LENGTH: 3
<212> TYPE: PRT
<213> ORGANISM: Artificial Sequence
<220> FEATURE:
<223> OTHER INFORMATION: synthetic

<400> SEQUENCE: 7

Ala Ala Ser
1

<210> SEQ ID NO 8
<211> LENGTH: 9
<212> TYPE: PRT
<213> ORGANISM: Artificial Sequence
<220> FEATURE:
<223> OTHER INFORMATION: synthetic

<400> SEQUENCE: 8

Gln Gln Ser Ser Asn Thr Pro Phe Thr
1               5

<210> SEQ ID NO 9
<211> LENGTH: 444
<212> TYPE: PRT
<213> ORGANISM: Artificial Sequence
<220> FEATURE:
<223> OTHER INFORMATION: aa 1-117: HCVR
      aa 118-444: HC constant

<400> SEQUENCE: 9

Glu Val Gln Leu Leu Glu Ser Gly Gly Val Leu Val Gln Pro Gly Gly
1               5                   10                  15

Ser Leu Arg Leu Ser Cys Ala Ala Ser Gly Phe Thr Phe Ser Asn Phe
                20                  25                  30

Gly Met Thr Trp Val Arg Gln Ala Pro Gly Lys Gly Leu Glu Trp Val
            35                  40                  45

```
Ser Gly Ile Ser Gly Gly Arg Asp Thr Tyr Phe Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Lys Gly Glu Asp Thr Ala Val Tyr Tyr Cys
                 85                  90                  95

Val Lys Trp Gly Asn Ile Tyr Phe Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 10
<211> LENGTH: 214
```

```
<212> TYPE: PRT
<213> ORGANISM: Artificial Sequence
<220> FEATURE:
<223> OTHER INFORMATION: aa 1-107: LCVR
      aa 108-214: LC constant

<400> SEQUENCE: 10

Asp Ile Gln Met Thr Gln Ser Pro Ser Ser Leu Ser Ala Ser Val Gly
1               5                   10                  15

Asp Ser Ile Thr Ile Thr Cys Arg Ala Ser Leu Ser Ile Asn Thr Phe
            20                  25                  30

Leu Asn Trp Tyr Gln Gln Lys Pro Gly Lys Ala Pro Asn Leu Leu Ile
        35                  40                  45

Tyr Ala Ala Ser Ser Leu His Gly Gly Val Pro Ser Arg Phe Ser Gly
50                  55                  60

Ser Gly Ser Gly Thr Asp Phe Thr Leu Thr Ile Arg Thr Leu Gln Pro
65                  70                  75                  80

Glu Asp Phe Ala Thr Tyr Tyr Cys Gln Gln Ser Ser Asn Thr Pro Phe
                85                  90                  95

Thr Phe Gly Pro Gly Thr Val Val Asp Phe Arg Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 11
<211> LENGTH: 443
<212> TYPE: PRT
<213> ORGANISM: Artificial Sequence
<220> FEATURE:
<223> OTHER INFORMATION: HC (minus C-terminal Lysine)

<400> SEQUENCE: 11

Glu Val Gln Leu Leu Glu Ser Gly Gly Val Leu Val Gln Pro Gly Gly
1               5                   10                  15

Ser Leu Arg Leu Ser Cys Ala Ala Ser Gly Phe Thr Phe Ser Asn Phe
            20                  25                  30

Gly Met Thr Trp Val Arg Gln Ala Pro Gly Lys Gly Leu Glu Trp Val
        35                  40                  45

Ser Gly Ile Ser Gly Gly Gly Arg Asp Thr Tyr Phe Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Gly Glu Asp Thr Ala Val Tyr Tyr Cys
                85                  90                  95

Val Lys Trp Gly Asn Ile Tyr Phe Asp Tyr Trp Gly Gln Gly Thr Leu
```

-continued

```
            100                 105                 110
Val Thr Val Ser Ser Ala Ser Thr Lys Gly Pro Ser Val Phe Pro Leu
        115                 120                 125
Ala Pro Cys Ser Arg Ser Thr Ser Glu Ser Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Lys Thr Tyr Thr Cys Asn Val Asp His Lys Pro Ser Asn
        195                 200                 205
Thr Lys Val Asp Lys Arg Val Glu Ser Lys Tyr Gly Pro Pro Cys Pro
    210                 215                 220
Pro Cys Pro Ala Pro Glu Phe Leu Gly Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser Gln Glu Asp Pro Glu Val Gln Phe
            260                 265                 270
Asn Trp Tyr Val Asp Gly Val Glu Val His Asn Ala Lys Thr Lys Pro
        275                 280                 285
Arg Glu Glu Gln Phe Asn Ser Thr Tyr Arg Val Val Ser Val Leu Thr
    290                 295                 300
Val Leu His Gln Asp Trp Leu Asn Gly Lys Glu Tyr Lys Cys Lys Val
305                 310                 315                 320
Ser Asn Lys Gly Leu Pro Ser Ser Ile Glu Lys Thr Ile Ser Lys Ala
                325                 330                 335
Lys Gly Gln Pro Arg Glu Pro Gln Val Tyr Thr Leu Pro Pro Ser Gln
            340                 345                 350
Glu Glu Met Thr Lys Asn Gln Val Ser Leu Thr Cys Leu Val Lys Gly
        355                 360                 365
Phe Tyr Pro Ser Asp Ile Ala Val Glu Trp Glu Ser Asn Gly Gln Pro
    370                 375                 380
Glu Asn Asn Tyr Lys Thr Thr Pro Pro Val Leu Asp Ser Asp Gly Ser
385                 390                 395                 400
Phe Phe Leu Tyr Ser Arg Leu Thr Val Asp Lys Ser Arg Trp Gln Glu
                405                 410                 415
Gly Asn Val Phe Ser Cys Ser Val Met His Glu Ala Leu His Asn His
            420                 425                 430
Tyr Thr Gln Lys Ser Leu Ser Leu Ser Leu Gly
        435                 440
```